US012424319B2

(12) United States Patent
Posnack et al.

(10) Patent No.: US 12,424,319 B2
(45) Date of Patent: Sep. 23, 2025

(54) SYSTEM FOR REMOTE TREATMENT UTILIZING PRIVACY CONTROLS

(71) Applicant: ROM TECHNOLOGIES, INC., Las Vegas, NV (US)

(72) Inventors: Daniel Posnack, Fort Lauderdale, FL (US); Peter Arn, Roxbury, CT (US); S. Adam Hacking, Nashua, NH (US); Micheal Mueller, Oil City, PA (US); Joseph Guaneri, Merrick, NY (US); Jonathan Greene, Denver, CO (US)

(73) Assignee: ROM Technologies, Inc., Brookfield, CT (US)

( * ) Notice: Subject to any disclaimer, the term of this patent is extended or adjusted under 35 U.S.C. 154(b) by 0 days.

(21) Appl. No.: 18/165,756

(22) Filed: Feb. 7, 2023

(65) Prior Publication Data
US 2023/0178235 A1 Jun. 8, 2023

Related U.S. Application Data

(62) Division of application No. 17/075,049, filed on Oct. 20, 2020.

(Continued)

(51) Int. Cl.
G16H 40/67 (2018.01)
G06F 21/62 (2013.01)
(Continued)

(52) U.S. Cl.
CPC ......... G16H 40/67 (2018.01); G06F 21/6254 (2013.01); G16H 15/00 (2018.01); G16H 20/30 (2018.01); G16H 80/00 (2018.01)

(58) Field of Classification Search
CPC ........ G16H 40/67; G16H 15/00; G16H 20/30; G16H 80/00; G06F 21/6254
See application file for complete search history.

(56) References Cited

U.S. PATENT DOCUMENTS 823,712 A 6/1906 Uhlmann
4,499,900 A 2/1985 Petrofsky et al.
(Continued)

FOREIGN PATENT DOCUMENTS

CA 3193419 A1 3/2022
CN 2885238 Y 4/2007
(Continued)

OTHER PUBLICATIONS

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.
(Continued)

Primary Examiner — Sheetal R Paulson
(74) Attorney, Agent, or Firm — Dickinson Wright PLLC; Jonathan H. Harder; Stephen A. Mason

(57) ABSTRACT

A method for displaying clinician user interface generated by a computer is disclosed. The method may include, displaying clinician user interface generated by a computer. The method may also include a profile display presenting information regarding a treatment history of a patient. The method may also include a protocol management display presenting a treatment plan, with the treatment plan comprising a plurality of treatment protocols. The method may also include a plan modification control configured to modify the plurality of treatment protocols of the treatment plan. The method may include a login interface configured to enable a person to access the clinician user interface by providing a credential associated with one of a plurality of user accounts. The method may include wherein each of the plurality of user accounts has a corresponding set of permissions controlling access to patient data on the clinician user interface.

20 Claims, 28 Drawing Sheets

Related U.S. Application Data

(60) Provisional application No. 62/931,278, filed on Nov. 6, 2019.

(51) Int. Cl.
*G16H 15/00* (2018.01)
*G16H 20/30* (2018.01)
*G16H 80/00* (2018.01)

(56) References Cited

U.S. PATENT DOCUMENTS

| | | |
|---|---|---|
| 4,822,032 A | 4/1989 | Whitmore et al. |
| 4,860,763 A | 8/1989 | Schminke |
| 4,869,497 A | 9/1989 | Stewart et al. |
| 4,932,650 A | 6/1990 | Bingham et al. |
| 5,137,501 A | 8/1992 | Mertesdorf |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,318,487 A | 6/1994 | Golen |
| 5,324,241 A | 6/1994 | Artigues et al. |
| 5,336,147 A | 8/1994 | Sweeney, III |
| 5,338,272 A | 8/1994 | Sweeney, III |
| 5,356,356 A | 10/1994 | Hildebrandt |
| 5,361,649 A | 11/1994 | Slocum, Jr. |
| D359,777 S | 6/1995 | Hildebrandt |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |
| 5,860,941 A | 1/1999 | Saringer et al. |
| 5,950,813 A | 9/1999 | Hoskins et al. |
| 6,007,459 A | 12/1999 | Burgess |
| D421,075 S | 2/2000 | Hildebrandt |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,162,189 A | 12/2000 | Girone et al. |
| 6,182,029 B1 | 1/2001 | Friedman |
| D438,580 S | 3/2001 | Shaw |
| 6,253,638 B1 | 7/2001 | Bermudez |
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,450,923 B1 | 9/2002 | Vatti |
| 6,474,193 B1 | 11/2002 | Farney |
| 6,491,649 B1 | 12/2002 | Ombrellaro |
| 6,514,085 B2 | 2/2003 | Slattery et al. |
| 6,535,861 B1 | 3/2003 | OConnor et al. |
| 6,543,309 B2 | 4/2003 | Heim |
| 6,589,139 B1 | 7/2003 | Butterworth |
| 6,601,016 B1 | 7/2003 | Brown et al. |
| 6,602,191 B2 | 8/2003 | Quy |
| 6,613,000 B1 | 9/2003 | Reinkensmeyer et al. |
| 6,626,800 B1 | 9/2003 | Casler |
| 6,626,805 B1 | 9/2003 | Lightbody |
| 6,640,122 B2 | 10/2003 | Manoli |
| 6,640,662 B1 | 11/2003 | Baxter |
| 6,652,425 B1 | 11/2003 | Martin et al. |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 6,902,513 B1 | 6/2005 | McClure |
| 7,058,453 B2 | 6/2006 | Nelson et al. |
| 7,063,643 B2 | 6/2006 | Arai |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,406,003 B2 | 7/2008 | Burkhardt et al. |
| 7,507,188 B2 | 3/2009 | Nurre |
| 7,594,879 B2 | 9/2009 | Johnson |
| 7,628,730 B1 | 12/2009 | Watterson et al. |
| D610,635 S | 2/2010 | Hildebrandt |
| 7,778,851 B2 | 8/2010 | Schoenberg et al. |
| 7,809,601 B2 | 10/2010 | Shaya et al. |
| 7,815,551 B2 | 10/2010 | Merli |
| 7,833,135 B2 | 11/2010 | Radow et al. |
| 7,837,472 B1 | 11/2010 | Elsmore et al. |
| 7,890,342 B1 | 2/2011 | Yruko |
| 7,955,219 B2 | 6/2011 | Birrell et al. |
| 7,969,315 B1 | 6/2011 | Ross et al. |
| 7,988,599 B2 | 8/2011 | Ainsworth et al. |
| 8,012,107 B2 | 9/2011 | Einav et al. |
| 8,021,270 B2 | 9/2011 | D'Eredita |
| 8,038,578 B2 | 10/2011 | Olrik et al. |
| 8,079,937 B2 | 12/2011 | Bedell |
| 8,113,991 B2 | 2/2012 | Kutliroff |
| 8,172,724 B2 | 5/2012 | Solomon |
| 8,177,732 B2 | 5/2012 | Einav et al. |
| 8,287,434 B2 | 10/2012 | Zavadsky et al. |
| 8,298,123 B2 | 10/2012 | Hickman |
| 8,371,990 B2 | 2/2013 | Shea |
| 8,419,593 B2 | 4/2013 | Ainsworth et al. |
| 8,465,398 B2 | 6/2013 | Lee et al. |
| 8,503,086 B2 | 8/2013 | French |
| 8,506,458 B2 | 8/2013 | Dugan |
| 8,515,777 B1 | 8/2013 | Rajasenan |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,613,689 B2 | 12/2013 | Dyer et al. |
| 8,615,529 B2 | 12/2013 | Reiner |
| 8,672,812 B2 | 3/2014 | Dugan |
| 8,751,264 B2 | 6/2014 | Beraja et al. |
| 8,784,273 B2 | 7/2014 | Dugan |
| 8,818,496 B2 | 8/2014 | Dziubinski et al. |
| 8,823,448 B1 | 9/2014 | Shen |
| 8,845,493 B2 | 9/2014 | Watterson et al. |
| 8,849,681 B2 | 9/2014 | Hargrove et al. |
| 8,864,628 B2 | 10/2014 | Boyette et al. |
| 8,893,287 B2 | 11/2014 | Gjonej et al. |
| 8,911,327 B1 | 12/2014 | Boyette |
| 8,979,711 B2 | 3/2015 | Dugan |
| 9,004,598 B2 | 4/2015 | Weber |
| 9,044,630 B1 | 6/2015 | Lampert et al. |
| 9,167,281 B2 | 10/2015 | Petrov et al. |
| D744,050 S | 11/2015 | Colburn |
| 9,248,071 B1 | 2/2016 | Brenda |
| 9,256,711 B2 | 2/2016 | Horseman |
| 9,272,091 B2 | 3/2016 | Skelton |
| 9,272,185 B2 | 3/2016 | Dugan |
| 9,283,434 B1 | 3/2016 | Wu |
| 9,295,878 B2 | 3/2016 | Corbalis et al. |
| 9,311,789 B1 | 4/2016 | Gwin |
| 9,312,907 B2 | 4/2016 | Auchinleck et al. |
| 9,367,668 B2 | 6/2016 | Flynt et al. |
| 9,409,054 B2 | 8/2016 | Dugan |

(56) References Cited

U.S. PATENT DOCUMENTS

| | | | |
|---|---|---|---|
| 9,443,205 | B2 | 9/2016 | Wall |
| 9,474,935 | B2 | 10/2016 | Abbondanza et al. |
| 9,480,873 | B2 | 11/2016 | Chuang |
| 9,481,428 | B2 | 11/2016 | Gros |
| 9,514,277 | B2 | 12/2016 | Hassing et al. |
| 9,566,472 | B2 | 2/2017 | Dugan |
| 9,579,056 | B2 | 2/2017 | Rosenbek et al. |
| 9,629,558 | B2 | 4/2017 | Yuen et al. |
| 9,640,057 | B1 | 5/2017 | Ross |
| 9,707,147 | B2 | 7/2017 | Levital et al. |
| 9,713,744 | B2 | 7/2017 | Suzuki |
| D794,142 | S | 8/2017 | Zhou |
| 9,717,947 | B2 | 8/2017 | Lin |
| 9,737,761 | B1 | 8/2017 | Govindarajan |
| 9,757,612 | B2 | 9/2017 | Weber |
| 9,773,330 | B1 | 9/2017 | Douglas |
| 9,782,621 | B2 | 10/2017 | Chiang et al. |
| 9,802,076 | B2 | 10/2017 | Murray et al. |
| 9,802,081 | B2 | 10/2017 | Ridgel et al. |
| 9,813,239 | B2 | 11/2017 | Chee et al. |
| 9,827,445 | B2 | 11/2017 | Marcos et al. |
| 9,849,337 | B2 | 12/2017 | Roman et al. |
| 9,868,028 | B2 | 1/2018 | Shin |
| 9,872,087 | B2 | 1/2018 | DelloStritto et al. |
| 9,872,637 | B2 | 1/2018 | Kording et al. |
| 9,914,053 | B2 | 3/2018 | Dugan |
| 9,919,198 | B2 | 3/2018 | Romeo et al. |
| 9,937,382 | B2 | 4/2018 | Dugan |
| 9,939,784 | B1 | 4/2018 | Berardinelli |
| 9,974,478 | B1 | 5/2018 | Brokaw |
| 9,977,587 | B2 | 5/2018 | Mountain |
| 9,993,181 | B2 | 6/2018 | Ross |
| 9,997,082 | B2 | 6/2018 | Kaleal |
| 10,004,946 | B2 | 6/2018 | Ross |
| 10,026,052 | B2 | 7/2018 | Brown et al. |
| D826,349 | S | 8/2018 | Oblamski |
| 10,055,550 | B2 | 8/2018 | Goetz |
| 10,058,473 | B2 | 8/2018 | Oshima et al. |
| 10,074,148 | B2 | 9/2018 | Cashman et al. |
| 10,089,443 | B2 | 10/2018 | Miller et al. |
| 10,111,643 | B2 | 10/2018 | Shulhauser et al. |
| 10,130,311 | B1 | 11/2018 | De Sapio et al. |
| 10,137,328 | B2 | 11/2018 | Baudhuin |
| 10,143,395 | B2 | 12/2018 | Chakravarthy et al. |
| 10,155,134 | B2 | 12/2018 | Dugan |
| 10,159,872 | B2 | 12/2018 | Sasaki et al. |
| 10,173,094 | B2 | 1/2019 | Gomberg |
| 10,173,095 | B2 | 1/2019 | Gomberg et al. |
| 10,173,096 | B2 | 1/2019 | Gomberg et al. |
| 10,173,097 | B2 | 1/2019 | Gomberg et al. |
| 10,198,928 | B1 | 2/2019 | Ross et al. |
| 10,226,663 | B2 | 3/2019 | Gomberg et al. |
| 10,231,664 | B2 | 3/2019 | Ganesh |
| 10,244,990 | B2 | 4/2019 | Hu et al. |
| 10,258,823 | B2 | 4/2019 | Cole |
| 10,322,315 | B2 | 6/2019 | Foley et al. |
| 10,325,070 | B2 | 6/2019 | Beale et al. |
| 10,327,697 | B1 | 6/2019 | Stein et al. |
| 10,362,940 | B2 | 7/2019 | Tran |
| 10,369,021 | B2 | 8/2019 | Zoss et al. |
| 10,380,866 | B1 | 8/2019 | Ross et al. |
| 10,413,222 | B1 | 9/2019 | Kayyali |
| 10,413,238 | B1 | 9/2019 | Cooper |
| 10,424,033 | B2 | 9/2019 | Romeo |
| 10,430,552 | B2 | 10/2019 | Mihai |
| D866,957 | S | 11/2019 | Ross et al. |
| 10,468,131 | B2 | 11/2019 | Macoviak et al. |
| 10,475,323 | B1 | 11/2019 | Ross |
| 10,475,537 | B2 | 11/2019 | Purdie et al. |
| 10,492,977 | B2 | 12/2019 | Kapure et al. |
| 10,507,358 | B2 | 12/2019 | Kinnunen et al. |
| 10,542,914 | B2 | 1/2020 | Forth et al. |
| 10,546,467 | B1 | 1/2020 | Luciano, Jr. et al. |
| 10,569,122 | B2 | 2/2020 | Johnson |
| 10,572,626 | B2 | 2/2020 | Balram |
| 10,576,331 | B2 | 3/2020 | Kuo |
| 10,581,896 | B2 | 3/2020 | Nachenberg |
| 10,625,114 | B2 | 4/2020 | Ercanbrack |
| 10,646,746 | B1 | 5/2020 | Gomberg et al. |
| 10,660,534 | B2 | 5/2020 | Lee et al. |
| 10,678,890 | B2 | 6/2020 | Bitran et al. |
| 10,685,092 | B2 | 6/2020 | Paparella et al. |
| 10,741,285 | B2 | 8/2020 | Moturu |
| 10,777,200 | B2 | 9/2020 | Will et al. |
| D899,605 | S | 10/2020 | Ross et al. |
| 10,792,495 | B2 | 10/2020 | Izvorski et al. |
| 10,814,170 | B2 | 10/2020 | Wang et al. |
| 10,857,426 | B1 | 12/2020 | Neumann |
| 10,867,695 | B2 | 12/2020 | Neagle |
| 10,874,905 | B2 | 12/2020 | Belson et al. |
| D907,143 | S | 1/2021 | Ach et al. |
| 10,881,911 | B2 | 1/2021 | Kwon et al. |
| 10,918,332 | B2 | 2/2021 | Belson et al. |
| 10,931,643 | B1 | 2/2021 | Neumann |
| 10,987,176 | B2 | 4/2021 | Poltaretskyi et al. |
| 10,991,463 | B2 | 4/2021 | Kutzko et al. |
| 11,000,735 | B2 | 5/2021 | Orady et al. |
| 11,045,709 | B2 | 6/2021 | Putnam |
| 11,065,170 | B2 | 7/2021 | Yang et al. |
| 11,065,527 | B2 | 7/2021 | Putnam |
| 11,069,436 | B2 | 7/2021 | Mason et al. |
| 11,071,597 | B2 | 7/2021 | Posnack et al. |
| 11,075,000 | B2 | 7/2021 | Mason et al. |
| D928,635 | S | 8/2021 | Hacking et al. |
| 11,087,865 | B2 | 8/2021 | Mason et al. |
| 11,094,400 | B2 | 8/2021 | Riley et al. |
| 11,101,028 | B2 | 8/2021 | Mason et al. |
| 11,107,591 | B1 | 8/2021 | Mason |
| 11,139,060 | B2 | 10/2021 | Mason et al. |
| 11,185,735 | B2 | 11/2021 | Arn et al. |
| 11,185,738 | B1 | 11/2021 | McKirdy et al. |
| D939,096 | S | 12/2021 | Lee |
| D939,644 | S | 12/2021 | Ach et al. |
| D940,797 | S | 1/2022 | Ach et al. |
| D940,891 | S | 1/2022 | Lee |
| 11,229,727 | B2 | 1/2022 | Tatonetti |
| 11,229,788 | B1 | 1/2022 | John |
| 11,265,234 | B2 | 3/2022 | Guaneri et al. |
| 11,270,795 | B2 | 3/2022 | Mason et al. |
| 11,272,879 | B2 | 3/2022 | Wiedenhoefer et al. |
| 11,278,766 | B2 | 3/2022 | Lee |
| 11,282,599 | B2 | 3/2022 | Mason et al. |
| 11,282,604 | B2 | 3/2022 | Mason et al. |
| 11,282,608 | B2 | 3/2022 | Mason et al. |
| 11,284,797 | B2 | 3/2022 | Mason et al. |
| D948,639 | S | 4/2022 | Ach et al. |
| 11,295,848 | B2 | 4/2022 | Mason et al. |
| 11,298,284 | B2 | 4/2022 | Bayerlein |
| 11,309,085 | B2 | 4/2022 | Mason et al. |
| 11,317,975 | B2 | 5/2022 | Mason et al. |
| 11,325,005 | B2 | 5/2022 | Mason et al. |
| 11,328,807 | B2 | 5/2022 | Mason et al. |
| 11,337,648 | B2 | 5/2022 | Mason |
| 11,347,829 | B1 | 5/2022 | Sclar et al. |
| 11,348,683 | B2 | 5/2022 | Guaneri et al. |
| 11,370,328 | B2 | 6/2022 | Main |
| 11,376,470 | B2 | 7/2022 | Weldemariam |
| 11,404,150 | B2 | 8/2022 | Guaneri et al. |
| 11,410,768 | B2 | 8/2022 | Mason et al. |
| 11,422,841 | B2 | 8/2022 | Jeong |
| 11,437,137 | B1 | 9/2022 | Harris |
| 11,495,355 | B2 | 11/2022 | McNutt et al. |
| 11,508,258 | B2 | 11/2022 | Nakashima et al. |
| 11,524,210 | B2 | 12/2022 | Kim et al. |
| 11,527,326 | B2 | 12/2022 | McNair et al. |
| 11,532,402 | B2 | 12/2022 | Farley et al. |
| 11,534,654 | B2 | 12/2022 | Silcock et al. |
| D976,339 | S | 1/2023 | Li |
| 11,553,969 | B1 | 1/2023 | Lang et al. |
| 11,621,067 | B1 | 4/2023 | Nolan |
| 11,636,944 | B2 | 4/2023 | Hanrahan et al. |
| 11,654,327 | B2 | 5/2023 | Phillips et al. |
| 11,663,673 | B2 | 5/2023 | Pyles |
| 11,673,024 | B2 | 6/2023 | Omid-Zohoor |

(56) References Cited

U.S. PATENT DOCUMENTS

| | | |
|---|---|---|
| 11,701,548 B2 | 7/2023 | Posnack et al. |
| 11,776,676 B2 | 10/2023 | Savolainen |
| 11,944,579 B2 | 4/2024 | Sankai |
| 11,957,960 B2 | 4/2024 | Bissonnette et al. |
| 12,004,871 B1 | 6/2024 | Fazeli |
| 12,057,210 B2 * | 8/2024 | Akinola ............... G16H 10/60 |
| 12,205,704 B2 | 1/2025 | Hosoi et al. |
| 2001/0044573 A1 | 11/2001 | Manoli |
| 2002/0010596 A1 | 1/2002 | Matory |
| 2002/0072452 A1 | 6/2002 | Torkelson |
| 2002/0143279 A1 | 10/2002 | Porter et al. |
| 2002/0160883 A1 | 10/2002 | Dugan |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0064860 A1 | 4/2003 | Yamashita et al. |
| 2003/0064863 A1 | 4/2003 | Chen |
| 2003/0083596 A1 | 5/2003 | Kramer et al. |
| 2003/0092536 A1 | 5/2003 | Romanelli et al. |
| 2003/0181832 A1 | 9/2003 | Carnahan et al. |
| 2004/0072652 A1 | 4/2004 | Alessandri et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2004/0197727 A1 | 10/2004 | Sachdeva et al. |
| 2004/0204959 A1 | 10/2004 | Moreano et al. |
| 2005/0015118 A1 | 1/2005 | Davis et al. |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0115561 A1 | 6/2005 | Stahmann |
| 2005/0143641 A1 | 6/2005 | Tashiro |
| 2005/0274220 A1 | 12/2005 | Reboullet |
| 2006/0003871 A1 | 1/2006 | Houghton et al. |
| 2006/0046905 A1 | 3/2006 | Doody, Jr. et al. |
| 2006/0058648 A1 | 3/2006 | Meier |
| 2006/0064136 A1 | 3/2006 | Wang |
| 2006/0064329 A1 | 3/2006 | Abolfathi et al. |
| 2006/0129432 A1 | 6/2006 | Choi et al. |
| 2006/0199700 A1 | 9/2006 | LaStayo et al. |
| 2006/0247095 A1 | 11/2006 | Rummerfield |
| 2006/0277074 A1 | 12/2006 | Einav |
| 2007/0042868 A1 | 2/2007 | Fisher et al. |
| 2007/0118389 A1 | 5/2007 | Shipon |
| 2007/0137307 A1 | 6/2007 | Gruben et al. |
| 2007/0173392 A1 | 7/2007 | Stanford |
| 2007/0184414 A1 | 8/2007 | Perez |
| 2007/0194939 A1 | 8/2007 | Alvarez et al. |
| 2007/0219059 A1 | 9/2007 | Schwartz |
| 2007/0271065 A1 | 11/2007 | Gupta et al. |
| 2007/0287597 A1 | 12/2007 | Cameron |
| 2008/0021834 A1 | 1/2008 | Holla et al. |
| 2008/0077619 A1 | 3/2008 | Gilley et al. |
| 2008/0082356 A1 | 4/2008 | Friedlander et al. |
| 2008/0096726 A1 | 4/2008 | Riley et al. |
| 2008/0153592 A1 | 6/2008 | James-Herbert |
| 2008/0161166 A1 | 7/2008 | Lo |
| 2008/0161733 A1 | 7/2008 | Einav et al. |
| 2008/0183500 A1 | 7/2008 | Banigan |
| 2008/0281633 A1 | 11/2008 | Burdea et al. |
| 2008/0300914 A1 | 12/2008 | Karkanias et al. |
| 2008/0312040 A1 | 12/2008 | Ochi |
| 2009/0011907 A1 | 1/2009 | Radow et al. |
| 2009/0037334 A1 | 2/2009 | Hsu |
| 2009/0058635 A1 | 3/2009 | LaLonde et al. |
| 2009/0070138 A1 | 3/2009 | Langheier et al. |
| 2009/0157617 A1 | 6/2009 | Herlocker |
| 2009/0211395 A1 | 8/2009 | Mule |
| 2009/0270227 A1 | 10/2009 | Ashby et al. |
| 2009/0287503 A1 | 11/2009 | Angell et al. |
| 2009/0299766 A1 | 12/2009 | Friedlander et al. |
| 2010/0048358 A1 | 2/2010 | Tchao et al. |
| 2010/0062818 A1 | 3/2010 | Haughay, Jr. |
| 2010/0076786 A1 | 3/2010 | Dalton et al. |
| 2010/0121160 A1 | 5/2010 | Stark et al. |
| 2010/0173747 A1 | 7/2010 | Chen et al. |
| 2010/0216168 A1 | 8/2010 | Heinzman et al. |
| 2010/0234184 A1 | 9/2010 | Le Page et al. |
| 2010/0248899 A1 | 9/2010 | Bedell et al. |
| 2010/0248905 A1 | 9/2010 | Lu |
| 2010/0262052 A1 | 10/2010 | Lunau et al. |
| 2010/0268304 A1 | 10/2010 | Matos |
| 2010/0293003 A1 | 11/2010 | Abbo |
| 2010/0298102 A1 | 11/2010 | Bosecker et al. |
| 2010/0326207 A1 | 12/2010 | Topel |
| 2010/0332583 A1 | 12/2010 | Szabo |
| 2011/0010188 A1 | 1/2011 | Yoshikawa et al. |
| 2011/0047108 A1 | 2/2011 | Chakrabarty et al. |
| 2011/0082007 A1 | 4/2011 | Birrell |
| 2011/0087137 A1 | 4/2011 | Hanoun |
| 2011/0119212 A1 | 5/2011 | De Bruin et al. |
| 2011/0172059 A1 | 7/2011 | Watterson et al. |
| 2011/0195819 A1 | 8/2011 | Shaw et al. |
| 2011/0218462 A1 | 9/2011 | Smith |
| 2011/0218814 A1 | 9/2011 | Coats |
| 2011/0275483 A1 | 11/2011 | Dugan |
| 2011/0281249 A1 | 11/2011 | Gammell et al. |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0130196 A1 | 5/2012 | Jain et al. |
| 2012/0130197 A1 | 5/2012 | Kugler et al. |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0232438 A1 | 9/2012 | Cataldi et al. |
| 2012/0259648 A1 | 10/2012 | Mallon et al. |
| 2012/0259649 A1 | 10/2012 | Mallon et al. |
| 2012/0278759 A1 | 11/2012 | Curl et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2013/0066647 A1 | 3/2013 | Andrie |
| 2013/0108594 A1 | 5/2013 | Martin-Rendon et al. |
| 2013/0110545 A1 | 5/2013 | Smallwood |
| 2013/0123071 A1 | 5/2013 | Rhea |
| 2013/0123667 A1 | 5/2013 | Komatireddy et al. |
| 2013/0137550 A1 | 5/2013 | Skinner et al. |
| 2013/0137552 A1 | 5/2013 | Kemp et al. |
| 2013/0158368 A1 | 6/2013 | Pacione |
| 2013/0165195 A1 | 6/2013 | Watterson |
| 2013/0178334 A1 | 7/2013 | Brammer |
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0031174 A1 | 1/2014 | Huang |
| 2014/0062900 A1 | 3/2014 | Kaula et al. |
| 2014/0074179 A1 | 3/2014 | Heldman et al. |
| 2014/0089836 A1 | 3/2014 | Damani et al. |
| 2014/0108035 A1 | 4/2014 | Akbay |
| 2014/0113261 A1 | 4/2014 | Akiba |
| 2014/0113768 A1 | 4/2014 | Lin et al. |
| 2014/0135173 A1 | 5/2014 | Watterson |
| 2014/0155129 A1 | 6/2014 | Dugan |
| 2014/0163439 A1 | 6/2014 | Uryash et al. |
| 2014/0172442 A1 | 6/2014 | Broderick |
| 2014/0172460 A1 | 6/2014 | Kohli |
| 2014/0172514 A1 | 6/2014 | Schumann et al. |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0200414 A1 | 7/2014 | Osorio |
| 2014/0207264 A1 | 7/2014 | Quy |

(56) References Cited

U.S. PATENT DOCUMENTS

| | | |
|---|---|---|
| 2014/0207486 A1 | 7/2014 | Carty et al. |
| 2014/0228649 A1 | 8/2014 | Rayner et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0275816 A1 | 9/2014 | Sandmore |
| 2014/0303540 A1 | 10/2014 | Baym |
| 2014/0309083 A1 | 10/2014 | Dugan |
| 2014/0322686 A1 | 10/2014 | Kang |
| 2014/0347265 A1 | 11/2014 | Aimone et al. |
| 2014/0371816 A1 | 12/2014 | Matos |
| 2014/0372133 A1 | 12/2014 | Austrum et al. |
| 2015/0025816 A1 | 1/2015 | Ross |
| 2015/0045700 A1 | 2/2015 | Cavanagh et al. |
| 2015/0046192 A1 | 2/2015 | Raduchel |
| 2015/0051721 A1 | 2/2015 | Cheng |
| 2015/0065213 A1 | 3/2015 | Dugan |
| 2015/0073814 A1 | 3/2015 | Linebaugh |
| 2015/0088544 A1 | 3/2015 | Goldberg |
| 2015/0094192 A1 | 4/2015 | Skwortsow et al. |
| 2015/0099458 A1 | 4/2015 | Weisner et al. |
| 2015/0099952 A1 | 4/2015 | Lain et al. |
| 2015/0111644 A1 | 4/2015 | Larson |
| 2015/0112230 A1 | 4/2015 | Iglesias |
| 2015/0112702 A1 | 4/2015 | Joao et al. |
| 2015/0130830 A1 | 5/2015 | Nagasaki |
| 2015/0141200 A1 | 5/2015 | Murray et al. |
| 2015/0142142 A1 | 5/2015 | Campana Aguilera et al. |
| 2015/0149217 A1 | 5/2015 | Kaburagi |
| 2015/0151162 A1 | 6/2015 | Dugan |
| 2015/0157938 A1 | 6/2015 | Domansky et al. |
| 2015/0161331 A1 | 6/2015 | Oleynik |
| 2015/0161876 A1 | 6/2015 | Castillo |
| 2015/0174446 A1 | 6/2015 | Chiang |
| 2015/0196804 A1 | 7/2015 | Koduri |
| 2015/0196805 A1 | 7/2015 | Koduri |
| 2015/0199494 A1 | 7/2015 | Koduri |
| 2015/0217056 A1 | 8/2015 | Kadavy et al. |
| 2015/0251074 A1 | 9/2015 | Ahmed et al. |
| 2015/0257679 A1 | 9/2015 | Ross |
| 2015/0265209 A1 | 9/2015 | Zhang |
| 2015/0290061 A1 | 10/2015 | Stafford et al. |
| 2015/0331997 A1 | 11/2015 | Joao |
| 2015/0335950 A1 | 11/2015 | Eder |
| 2015/0335951 A1 | 11/2015 | Eder |
| 2015/0339442 A1 | 11/2015 | Oleynik |
| 2015/0341812 A1 | 11/2015 | Dion et al. |
| 2015/0351664 A1 | 12/2015 | Ross |
| 2015/0351665 A1 | 12/2015 | Ross |
| 2015/0360069 A1 | 12/2015 | Marti et al. |
| 2015/0379232 A1 | 12/2015 | Mainwaring et al. |
| 2015/0379430 A1 | 12/2015 | Dirac et al. |
| 2016/0004820 A1 | 1/2016 | Moore |
| 2016/0007885 A1 | 1/2016 | Basta |
| 2016/0015995 A1 | 1/2016 | Leung et al. |
| 2016/0023081 A1 | 1/2016 | Popa-Simil et al. |
| 2016/0045170 A1 | 2/2016 | Migita |
| 2016/0081594 A1 | 3/2016 | Gaddipati |
| 2016/0086500 A1 | 3/2016 | Kaleal, III |
| 2016/0096073 A1 | 4/2016 | Rahman et al. |
| 2016/0117471 A1 | 4/2016 | Belt et al. |
| 2016/0132643 A1 | 5/2016 | Radhakrishna et al. |
| 2016/0140319 A1 | 5/2016 | Stark |
| 2016/0143593 A1 | 5/2016 | Fu et al. |
| 2016/0151670 A1 | 6/2016 | Dugan |
| 2016/0158534 A1 | 6/2016 | Guarraia et al. |
| 2016/0166833 A1 | 6/2016 | Bum |
| 2016/0166881 A1 | 6/2016 | Ridgel et al. |
| 2016/0193306 A1 | 7/2016 | Rabovsky et al. |
| 2016/0197918 A1 | 7/2016 | Turgeman et al. |
| 2016/0213924 A1 | 7/2016 | Coleman |
| 2016/0250519 A1 | 9/2016 | Watterson |
| 2016/0275259 A1 | 9/2016 | Nolan et al. |
| 2016/0287166 A1 | 10/2016 | Tran |
| 2016/0302666 A1 | 10/2016 | Shaya |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2016/0345841 A1 | 12/2016 | Jang et al. |
| 2016/0354636 A1 | 12/2016 | Jang |
| 2016/0361025 A1 | 12/2016 | Reicher et al. |
| 2016/0361597 A1 | 12/2016 | Cole et al. |
| 2016/0373477 A1 | 12/2016 | Moyle |
| 2017/0004260 A1 | 1/2017 | Moturu et al. |
| 2017/0011179 A1 | 1/2017 | Arshad et al. |
| 2017/0032092 A1 | 2/2017 | Mink et al. |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0091422 A1 | 3/2017 | Kumar et al. |
| 2017/0095670 A1 | 4/2017 | Ghaffari et al. |
| 2017/0095692 A1 | 4/2017 | Chang et al. |
| 2017/0095693 A1 | 4/2017 | Chang et al. |
| 2017/0100637 A1 | 4/2017 | Princen et al. |
| 2017/0106242 A1 | 4/2017 | Dugan |
| 2017/0113092 A1 | 4/2017 | Johnson |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0136298 A1 | 5/2017 | Bae |
| 2017/0143261 A1 | 5/2017 | Wiedenhoefer et al. |
| 2017/0147752 A1 | 5/2017 | Toru |
| 2017/0147789 A1 | 5/2017 | Wiedenhoefer et al. |
| 2017/0148297 A1 | 5/2017 | Ross |
| 2017/0168555 A1 | 6/2017 | Munoz et al. |
| 2017/0169177 A1 | 6/2017 | Beale |
| 2017/0173391 A1 | 6/2017 | Wiebe |
| 2017/0181698 A1 | 6/2017 | Wiedenhoefer et al. |
| 2017/0190052 A1 | 7/2017 | Jaekel et al. |
| 2017/0202724 A1 | 7/2017 | De Rossi |
| 2017/0209766 A1 | 7/2017 | Riley et al. |
| 2017/0220751 A1 | 8/2017 | Davis |
| 2017/0228517 A1 | 8/2017 | Saliman et al. |
| 2017/0235882 A1 | 8/2017 | Orlov et al. |
| 2017/0235906 A1 | 8/2017 | Dorris et al. |
| 2017/0243028 A1* | 8/2017 | LaFever .............. G06F 21/6254 |
| 2017/0258370 A1 | 9/2017 | Plotnik-Peleg et al. |
| 2017/0262604 A1 | 9/2017 | Francois |
| 2017/0265800 A1 | 9/2017 | Auchinleck et al. |
| 2017/0266501 A1 | 9/2017 | Sanders et al. |
| 2017/0270260 A1 | 9/2017 | Shetty |
| 2017/0278209 A1 | 9/2017 | Olsen et al. |
| 2017/0282015 A1 | 10/2017 | Wicks et al. |
| 2017/0283508 A1 | 10/2017 | Demopulos et al. |
| 2017/0286621 A1 | 10/2017 | Cox |
| 2017/0296861 A1 | 10/2017 | Burkinshaw |
| 2017/0300654 A1 | 10/2017 | Stein et al. |
| 2017/0304024 A1 | 10/2017 | Nobrega |
| 2017/0312614 A1 | 11/2017 | Tran et al. |
| 2017/0323481 A1 | 11/2017 | Tran et al. |
| 2017/0329917 A1 | 11/2017 | McRaith et al. |
| 2017/0329933 A1 | 11/2017 | Brust |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0347923 A1 | 12/2017 | Roh |
| 2017/0352157 A1 | 12/2017 | Madabhushi |
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0036591 A1 | 2/2018 | King et al. |
| 2018/0036593 A1 | 2/2018 | Ridgel et al. |
| 2018/0052962 A1 | 2/2018 | Van Der Koijk et al. |
| 2018/0056104 A1 | 3/2018 | Cromie et al. |
| 2018/0056130 A1 | 3/2018 | Bitran et al. |
| 2018/0060494 A1 | 3/2018 | Dias et al. |
| 2018/0070864 A1 | 3/2018 | Schuster |

(56) References Cited

U.S. PATENT DOCUMENTS

| | | |
|---|---|---|
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078182 A1 | 3/2018 | Chen |
| 2018/0078843 A1 | 3/2018 | Tran et al. |
| 2018/0085615 A1 | 3/2018 | Astolfi et al. |
| 2018/0089385 A1 | 3/2018 | Gupta |
| 2018/0096111 A1 | 4/2018 | Wells et al. |
| 2018/0099178 A1 | 4/2018 | Schaefer et al. |
| 2018/0102190 A1 | 4/2018 | Hogue et al. |
| 2018/0103859 A1 | 4/2018 | Provenzano |
| 2018/0113985 A1 | 4/2018 | Gandy et al. |
| 2018/0116741 A1 | 5/2018 | Garcia Kilroy et al. |
| 2018/0117417 A1 | 5/2018 | Davis |
| 2018/0130555 A1 | 5/2018 | Chronis et al. |
| 2018/0133551 A1 | 5/2018 | Chang |
| 2018/0140927 A1 | 5/2018 | Kito |
| 2018/0146870 A1 | 5/2018 | Shemesh |
| 2018/0177612 A1 | 6/2018 | Trabish et al. |
| 2018/0178061 A1 | 6/2018 | O'Larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0232492 A1 | 8/2018 | Al-Alul et al. |
| 2018/0236307 A1 | 8/2018 | Hyde et al. |
| 2018/0240552 A1 | 8/2018 | Tuyl et al. |
| 2018/0253991 A1 | 9/2018 | Tang et al. |
| 2018/0255110 A1 | 9/2018 | Dowlatkhah et al. |
| 2018/0256079 A1 | 9/2018 | Yang et al. |
| 2018/0263530 A1 | 9/2018 | Jung |
| 2018/0263535 A1 | 9/2018 | Cramer |
| 2018/0263552 A1 | 9/2018 | Graman et al. |
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0290017 A1 | 10/2018 | Fung |
| 2018/0296143 A1 | 10/2018 | Anderson et al. |
| 2018/0296157 A1 | 10/2018 | Bleich et al. |
| 2018/0318122 A1 | 11/2018 | LeCursi et al. |
| 2018/0326243 A1 | 11/2018 | Badi et al. |
| 2018/0330058 A1 | 11/2018 | Bates |
| 2018/0330810 A1 | 11/2018 | Gamarnik |
| 2018/0330824 A1 | 11/2018 | Athey et al. |
| 2018/0353812 A1 | 12/2018 | Lannon et al. |
| 2018/0360340 A1 | 12/2018 | Rehse et al. |
| 2018/0366225 A1 | 12/2018 | Mansi et al. |
| 2018/0373844 A1 | 12/2018 | Ferrandez-Escamez et al. |
| 2019/0005195 A1 | 1/2019 | Peterson |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0046794 A1 | 2/2019 | Goodall et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0080802 A1 | 3/2019 | Ziobro et al. |
| 2019/0083846 A1 | 3/2019 | Eder |
| 2019/0088356 A1 | 3/2019 | Oliver et al. |
| 2019/0090744 A1 | 3/2019 | Mahfouz |
| 2019/0096534 A1 | 3/2019 | Joao |
| 2019/0105551 A1 | 4/2019 | Ray |
| 2019/0108912 A1 | 4/2019 | Spurlock, III |
| 2019/0111299 A1 | 4/2019 | Radcliffe et al. |
| 2019/0115097 A1 | 4/2019 | Macoviak et al. |
| 2019/0117156 A1 | 4/2019 | Howard et al. |
| 2019/0118038 A1 | 4/2019 | Tana et al. |
| 2019/0118066 A1 | 4/2019 | Cardona |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0143191 A1 | 5/2019 | Ran et al. |
| 2019/0143193 A1 | 5/2019 | Kim |
| 2019/0145774 A1 | 5/2019 | Ellis |
| 2019/0163876 A1 | 5/2019 | Remme et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0200920 A1 | 7/2019 | Tien et al. |
| 2019/0209891 A1 | 7/2019 | Fung |
| 2019/0214119 A1 | 7/2019 | Wachira et al. |
| 2019/0223797 A1 | 7/2019 | Tran |
| 2019/0224528 A1 | 7/2019 | Omid-Zohoor et al. |
| 2019/0228856 A1 | 7/2019 | Leifer |
| 2019/0232108 A1 | 8/2019 | Kovach et al. |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0247718 A1 | 8/2019 | Blevins |
| 2019/0251456 A1 | 8/2019 | Constantin |
| 2019/0261959 A1 | 8/2019 | Frankel |
| 2019/0262084 A1 | 8/2019 | Roh |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0283247 A1 | 9/2019 | Chang |
| 2019/0304584 A1 | 10/2019 | Savolainen |
| 2019/0307983 A1 | 10/2019 | Goldman |
| 2019/0314681 A1 | 10/2019 | Yang |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0371472 A1 | 12/2019 | Blanchard |
| 2019/0385199 A1 | 12/2019 | Bender et al. |
| 2019/0388728 A1 | 12/2019 | Wang et al. |
| 2019/0392936 A1 | 12/2019 | Arric et al. |
| 2019/0392939 A1 | 12/2019 | Basta et al. |
| 2020/0005928 A1 | 1/2020 | Daniel |
| 2020/0015736 A1 | 1/2020 | Alhathal |
| 2020/0034665 A1 | 1/2020 | Ghanta |
| 2020/0034707 A1 | 1/2020 | Kivatinos et al. |
| 2020/0038703 A1 | 2/2020 | Cleary et al. |
| 2020/0051446 A1 | 2/2020 | Rubinstein |
| 2020/0054922 A1 | 2/2020 | Azaria |
| 2020/0066390 A1 | 2/2020 | Svendrys et al. |
| 2020/0085300 A1 | 3/2020 | Kwatra et al. |
| 2020/0090802 A1 | 3/2020 | Maron |
| 2020/0093418 A1 | 3/2020 | Kluger et al. |
| 2020/0121987 A1 | 4/2020 | Loh |
| 2020/0129808 A1 | 4/2020 | Fomin |
| 2020/0139194 A1 | 5/2020 | Min |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0188774 A1 | 6/2020 | Fung |
| 2020/0197744 A1 | 6/2020 | Schweighofer |
| 2020/0221975 A1 | 7/2020 | Basta et al. |
| 2020/0237291 A1 | 7/2020 | Raja |
| 2020/0237452 A1 | 7/2020 | Wolf et al. |
| 2020/0261763 A1 | 8/2020 | Park |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |

(56) References Cited

U.S. PATENT DOCUMENTS

| | | |
|---|---|---|
| 2020/0293712 A1 | 9/2020 | Potts et al. |
| 2020/0303063 A1 | 9/2020 | Sharma et al. |
| 2020/0312447 A1 | 10/2020 | Bohn et al. |
| 2020/0320454 A1 | 10/2020 | Almashor |
| 2020/0334972 A1 | 10/2020 | Gopalakrishnan |
| 2020/0346072 A1 | 11/2020 | Shah |
| 2020/0353314 A1 | 11/2020 | Messinger |
| 2020/0357299 A1 | 11/2020 | Patel et al. |
| 2020/0365256 A1 | 11/2020 | Hayashitani et al. |
| 2020/0391080 A1 | 12/2020 | Powers |
| 2020/0395112 A1 | 12/2020 | Ronner |
| 2020/0398083 A1 | 12/2020 | Adelsheim |
| 2020/0401224 A1 | 12/2020 | Cotton |
| 2020/0402662 A1 | 12/2020 | Esmailian et al. |
| 2020/0410374 A1 | 12/2020 | White |
| 2020/0410385 A1 | 12/2020 | Otsuki |
| 2020/0411162 A1 | 12/2020 | Lien et al. |
| 2020/0411170 A1 | 12/2020 | Brown |
| 2021/0005224 A1 | 1/2021 | Rothschild et al. |
| 2021/0005319 A1* | 1/2021 | Otsuki .................. G16H 40/40 |
| 2021/0008413 A1 | 1/2021 | Asikainen et al. |
| 2021/0015560 A1 | 1/2021 | Boddington et al. |
| 2021/0027889 A1 | 1/2021 | Neil et al. |
| 2021/0035674 A1 | 2/2021 | Volosin et al. |
| 2021/0050086 A1 | 2/2021 | Rose et al. |
| 2021/0065855 A1* | 3/2021 | Pepin .................... G16H 20/40 |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0077884 A1 | 3/2021 | De Las Casas Zolezzi et al. |
| 2021/0082554 A1 | 3/2021 | Kalia et al. |
| 2021/0093891 A1 | 4/2021 | Sheng et al. |
| 2021/0098099 A1 | 4/2021 | Neumann |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0125696 A1 | 4/2021 | Liu et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason |
| 2021/0134429 A1 | 5/2021 | Mason |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0187348 A1 | 6/2021 | Phillips et al. |
| 2021/0202090 A1 | 7/2021 | ODonovan et al. |
| 2021/0202103 A1 | 7/2021 | Bostic et al. |
| 2021/0205660 A1 | 7/2021 | Shavit |
| 2021/0217516 A1 | 7/2021 | Nash |
| 2021/0236020 A1 | 8/2021 | Matijevich et al. |
| 2021/0240853 A1 | 8/2021 | Carlson |
| 2021/0244998 A1 | 8/2021 | Hacking et al. |
| 2021/0245003 A1 | 8/2021 | Turner |
| 2021/0251562 A1 | 8/2021 | Jain |
| 2021/0272677 A1 | 9/2021 | Barbee |
| 2021/0338469 A1 | 11/2021 | Dempers |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0354002 A1 | 11/2021 | Schaefer |
| 2021/0361514 A1 | 11/2021 | Choi et al. |
| 2021/0366587 A1 | 11/2021 | Mason et al. |
| 2021/0375425 A1 | 12/2021 | Zhang |
| 2021/0383909 A1 | 12/2021 | Mason et al. |
| 2021/0391091 A1 | 12/2021 | Mason |
| 2021/0398668 A1 | 12/2021 | Chock et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0015838 A1 | 1/2022 | Posnack |
| 2022/0016480 A1 | 1/2022 | Bissonnette et al. |
| 2022/0016482 A1 | 1/2022 | Bissonnette |
| 2022/0016485 A1 | 1/2022 | Bissonnette |
| 2022/0016486 A1 | 1/2022 | Bissonnette |
| 2022/0020469 A1 | 1/2022 | Tanner |
| 2022/0044806 A1 | 2/2022 | Sanders et al. |
| 2022/0047921 A1 | 2/2022 | Bissonnette |
| 2022/0066548 A1 | 3/2022 | Helot |
| 2022/0079690 A1 | 3/2022 | Mason et al. |
| 2022/0080256 A1 | 3/2022 | Arn et al. |
| 2022/0080265 A1 | 3/2022 | Watterson |
| 2022/0105384 A1 | 4/2022 | Hacking et al. |
| 2022/0105385 A1 | 4/2022 | Hacking et al. |
| 2022/0105390 A1 | 4/2022 | Yuasa |
| 2022/0115133 A1 | 4/2022 | Mason et al. |
| 2022/0118218 A1 | 4/2022 | Bense et al. |
| 2022/0122724 A1* | 4/2022 | Durlach ............... A61B 5/6891 |
| 2022/0126169 A1 | 4/2022 | Mason |
| 2022/0133576 A1 | 5/2022 | Choi et al. |
| 2022/0148725 A1 | 5/2022 | Mason et al. |
| 2022/0158916 A1 | 5/2022 | Mason et al. |
| 2022/0176039 A1 | 6/2022 | Lintereur et al. |
| 2022/0181004 A1 | 6/2022 | Zilca et al. |
| 2022/0193491 A1 | 6/2022 | Mason |
| 2022/0230729 A1 | 7/2022 | Mason |
| 2022/0238222 A1 | 7/2022 | Neuberg |
| 2022/0238223 A1 | 7/2022 | Mason |
| 2022/0258935 A1 | 8/2022 | Kraft |
| 2022/0262483 A1 | 8/2022 | Rosenberg et al. |
| 2022/0262504 A1 | 8/2022 | Bratty et al. |
| 2022/0266094 A1 | 8/2022 | Mason et al. |
| 2022/0270738 A1 | 8/2022 | Mason et al. |
| 2022/0273985 A1 | 9/2022 | Jeong et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305291 A1 | 9/2022 | Hibbard |
| 2022/0305328 A1 | 9/2022 | Choi et al. |
| 2022/0314072 A1 | 10/2022 | Bissonnette et al. |
| 2022/0314075 A1 | 10/2022 | Mason et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0328181 A1 | 10/2022 | Mason et al. |
| 2022/0330823 A1 | 10/2022 | Janssen |
| 2022/0331663 A1 | 10/2022 | Mason |
| 2022/0338761 A1 | 10/2022 | Maddahi et al. |
| 2022/0339052 A1 | 10/2022 | Kim |
| 2022/0339501 A1 | 10/2022 | Mason et al. |
| 2022/0370851 A1 | 11/2022 | Guidarelli et al. |
| 2022/0384010 A1 | 12/2022 | Kanayama |
| 2022/0384012 A1 | 12/2022 | Mason |
| 2022/0392591 A1 | 12/2022 | Guaneri et al. |
| 2022/0395232 A1 | 12/2022 | Locke |
| 2022/0401783 A1 | 12/2022 | Choi |
| 2022/0415469 A1 | 12/2022 | Mason |
| 2022/0415471 A1 | 12/2022 | Mason |
| 2023/0001268 A1 | 1/2023 | Bissonnette et al. |

(56) References Cited

U.S. PATENT DOCUMENTS

| | | |
|---|---|---|
| 2023/0013530 A1 | 1/2023 | Mason |
| 2023/0014598 A1 | 1/2023 | Mason et al. |
| 2023/0029639 A1 | 2/2023 | Roy |
| 2023/0047253 A1 | 2/2023 | Gnanasambandam et al. |
| 2023/0048040 A1 | 2/2023 | Hacking et al. |
| 2023/0051751 A1 | 2/2023 | Hacking et al. |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |
| 2023/0190100 A1 | 6/2023 | Stump |
| 2023/0197240 A1 | 6/2023 | Rosenberg |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0218950 A1 | 7/2023 | Belson et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0249599 A1 | 8/2023 | Nicola |
| 2023/0253089 A1 | 8/2023 | Rosenberg et al. |
| 2023/0255555 A1 | 8/2023 | Sundaram et al. |
| 2023/0263428 A1 | 8/2023 | Hull et al. |
| 2023/0274813 A1 | 8/2023 | Rosenberg et al. |
| 2023/0282329 A1 | 9/2023 | Mason et al. |
| 2023/0364472 A1 | 11/2023 | Posnack |
| 2023/0368886 A1 | 11/2023 | Rosenberg |
| 2023/0377710 A1 | 11/2023 | Chen et al. |
| 2023/0377711 A1 | 11/2023 | Rosenberg |
| 2023/0377712 A1 | 11/2023 | Rosenberg |
| 2023/0386639 A1 | 11/2023 | Rosenberg |
| 2023/0390627 A1 | 12/2023 | Bolton |
| 2023/0395231 A1 | 12/2023 | Rosenberg |
| 2023/0395232 A1 | 12/2023 | Rosenberg |
| 2024/0029856 A1 | 1/2024 | Rosenberg |
| 2024/0058651 A1 | 2/2024 | Bissonnette |
| 2024/0177846 A1 | 5/2024 | Gnanasambandam |
| 2024/0203580 A1 | 6/2024 | Mason |

FOREIGN PATENT DOCUMENTS

| | | |
|---|---|---|
| CN | 101964151 A | 2/2011 |
| CN | 201889024 U | 7/2011 |
| CN | 202220794 U | 5/2012 |
| CN | 102670381 A | 9/2012 |
| CN | 103263336 A | 8/2013 |
| CN | 103390357 A | 11/2013 |
| CN | 103473631 A | 12/2013 |
| CN | 103488880 A | 1/2014 |
| CN | 103501328 A | 1/2014 |
| CN | 103721343 A | 4/2014 |
| CN | 203677851 U | 7/2014 |
| CN | 104335211 A | 2/2015 |
| CN | 105263448 A | 1/2016 |
| CN | 105620643 A | 6/2016 |
| CN | 105683977 A | 6/2016 |
| CN | 103136447 B | 8/2016 |
| CN | 105894088 A | 8/2016 |
| CN | 105930668 A | 9/2016 |
| CN | 205626871 U | 10/2016 |
| CN | 106127646 A | 11/2016 |
| CN | 106236502 A | 12/2016 |
| CN | 106510985 A | 3/2017 |
| CN | 106621195 A | 5/2017 |
| CN | 107066819 A | 8/2017 |
| CN | 107430641 A | 12/2017 |
| CN | 107551475 A | 1/2018 |
| CN | 107736982 A | 2/2018 |
| CN | 107930021 A | 4/2018 |
| CN | 108078737 A | 5/2018 |
| CN | 208224811 A | 12/2018 |
| CN | 109191954 A | 1/2019 |
| CN | 109363887 A | 2/2019 |
| CN | 208573971 U | 3/2019 |
| CN | 110148472 A | 8/2019 |
| CN | 110201358 A | 9/2019 |
| CN | 110215188 A | 9/2019 |
| CN | 110322957 A | 10/2019 |
| CN | 110808092 A | 2/2020 |
| CN | 110931103 A | 3/2020 |
| CN | 110993057 A | 4/2020 |
| CN | 111105859 A | 5/2020 |
| CN | 111111110 A | 5/2020 |
| CN | 111370088 A | 7/2020 |
| CN | 111460305 A | 7/2020 |
| CN | 111790111 A | 10/2020 |
| CN | 112071393 A | 12/2020 |
| CN | 212141371 U | 12/2020 |
| CN | 112289425 A | 1/2021 |
| CN | 212624809 U | 2/2021 |
| CN | 112603295 A | 4/2021 |
| CN | 213190965 U | 5/2021 |
| CN | 113384850 A | 9/2021 |
| CN | 113499572 A | 10/2021 |
| CN | 215136488 U | 12/2021 |
| CN | 113885361 A | 1/2022 |
| CN | 114049961 A | 2/2022 |
| CN | 114203274 A | 3/2022 |
| CN | 216258145 U | 4/2022 |
| CN | 114632302 A | 6/2022 |
| CN | 114694824 A | 7/2022 |
| CN | 114898832 A | 8/2022 |
| CN | 114983760 A | 9/2022 |
| CN | 217472652 U | 9/2022 |
| CN | 110270062 B | 10/2022 |
| CN | 218420859 U | 2/2023 |
| CN | 115954081 A | 4/2023 |
| DE | 95019 C | 1/1897 |
| DE | 7628633 U1 | 12/1977 |
| DE | 8519150 U1 | 10/1985 |
| DE | 3732905 A1 | 7/1988 |
| DE | 19619820 A1 | 12/1996 |
| DE | 29620008 U1 | 2/1997 |
| DE | 19947926 A1 | 4/2001 |
| DE | 102018202497 A1 | 8/2018 |
| DE | 102018211212 A1 | 1/2019 |
| DE | 102019108425 B3 | 8/2020 |
| EP | 199600 A2 | 10/1986 |
| EP | 0383137 A2 | 8/1990 |
| EP | 634319 A2 | 1/1995 |
| EP | 0919259 A1 | 6/1999 |
| EP | 1034817 A1 | 9/2000 |
| EP | 1159989 A1 | 12/2001 |
| EP | 1391179 A1 | 2/2004 |
| EP | 1968028 | 9/2008 |
| EP | 2564904 A1 | 3/2013 |
| EP | 2575064 A1 | 4/2013 |
| EP | 1909730 B1 | 4/2014 |
| EP | 2815242 A4 | 12/2014 |
| EP | 2869805 A | 5/2015 |
| EP | 2997951 A1 | 3/2016 |
| EP | 2688472 B1 | 4/2016 |
| EP | 3264303 A1 | 1/2018 |
| EP | 3323473 A1 | 5/2018 |
| EP | 3547322 A1 | 10/2019 |
| EP | 3627514 A1 | 3/2020 |
| EP | 3671700 A1 | 6/2020 |
| EP | 3688537 A1 | 8/2020 |
| EP | 3731733 A1 | 11/2020 |
| EP | 3984508 A1 | 4/2022 |
| EP | 3984509 A1 | 4/2022 |
| EP | 3984510 A1 | 4/2022 |
| EP | 3984511 A1 | 4/2022 |
| EP | 3984512 A1 | 4/2022 |
| EP | 3984513 A1 | 4/2022 |
| EP | 4054699 A1 | 9/2022 |
| EP | 4112033 A1 | 1/2023 |
| FR | 2527541 A2 | 12/1983 |
| FR | 3127393 A1 | 3/2023 |
| GB | 141664 A | 11/1920 |

(56) References Cited

FOREIGN PATENT DOCUMENTS

| | | |
|---|---|---|
| GB | 2336140 A | 10/1999 |
| GB | 2372459 A | 8/2002 |
| GB | 2512431 A | 10/2014 |
| GB | 2591542 B | 3/2022 |
| IN | 201811043670 A | 7/2018 |
| JP | 2000005339 A | 1/2000 |
| JP | 2003225875 A | 8/2003 |
| JP | 2005227928 A | 8/2005 |
| JP | 2005227928 A1 | 8/2005 |
| JP | 2009112336 A | 5/2009 |
| JP | 2013515995 A | 5/2013 |
| JP | 2014104139 A | 6/2014 |
| JP | 3193662 U | 10/2014 |
| JP | 3198173 U | 6/2015 |
| JP | 5804063 B2 | 11/2015 |
| JP | 2018102842 A | 7/2018 |
| JP | 2019028647 A | 2/2019 |
| JP | 2019134909 A | 8/2019 |
| JP | 6573739 B1 | 9/2019 |
| JP | 6659831 B2 | 3/2020 |
| JP | 2020057082 A | 4/2020 |
| JP | 6710357 B1 | 6/2020 |
| JP | 6775757 B1 | 10/2020 |
| JP | 2021027917 A | 2/2021 |
| JP | 6871379 B2 | 5/2021 |
| JP | 2022521378 A | 4/2022 |
| JP | 3238491 U | 7/2022 |
| JP | 7198364 B2 | 12/2022 |
| JP | 7202474 B2 | 1/2023 |
| JP | 7231750 B2 | 3/2023 |
| JP | 7231751 B2 | 3/2023 |
| JP | 7231752 B2 | 3/2023 |
| KR | 20020009724 A | 2/2002 |
| KR | 200276919 Y1 | 5/2002 |
| KR | 20020065253 A | 8/2002 |
| KR | 100582596 B1 | 5/2006 |
| KR | 101042258 B1 | 6/2011 |
| KR | 101258250 B1 | 4/2013 |
| KR | 101325581 B1 | 11/2013 |
| KR | 20140128630 A | 11/2014 |
| KR | 20150017693 A | 2/2015 |
| KR | 20150078191 A | 7/2015 |
| KR | 101580071 B1 | 12/2015 |
| KR | 101647620 B1 | 8/2016 |
| KR | 20160093990 A | 8/2016 |
| KR | 20170038837 A | 4/2017 |
| KR | 20180004928 A | 1/2018 |
| KR | 20190029175 A | 3/2019 |
| KR | 20190056116 A | 5/2019 |
| KR | 101988167 B1 | 6/2019 |
| KR | 101969392 B1 | 8/2019 |
| KR | 102055279 B1 | 12/2019 |
| KR | 20200019548 A | 2/2020 |
| KR | 102088333 B1 | 3/2020 |
| KR | 20200025290 A | 3/2020 |
| KR | 20200029180 A | 3/2020 |
| KR | 102097190 B1 | 4/2020 |
| KR | 102116664 B1 | 5/2020 |
| KR | 102116968 B1 | 5/2020 |
| KR | 20200056233 A | 5/2020 |
| KR | 102120828 B1 | 6/2020 |
| KR | 102121586 B1 | 6/2020 |
| KR | 102142713 B1 | 8/2020 |
| KR | 102162522 B1 | 10/2020 |
| KR | 20200119665 A | 10/2020 |
| KR | 102173553 B1 | 11/2020 |
| KR | 102180079 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102224618 B1 | 3/2021 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 20210052028 A | 5/2021 |
| KR | 102264498 B1 | 6/2021 |
| KR | 102352602 B1 | 1/2022 |
| KR | 102352603 B1 | 1/2022 |
| KR | 102352604 B1 | 1/2022 |
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| RU | 2014131288 A | 2/2016 |
| RU | 2607953 C2 | 1/2017 |
| TW | M474545 U | 3/2014 |
| TW | I442956 B | 7/2014 |
| TW | M638437 U | 3/2023 |
| WO | 1998009687 A1 | 3/1998 |
| WO | 0149235 A2 | 7/2001 |
| WO | 0151083 A2 | 7/2001 |
| WO | 2001050387 A1 | 7/2001 |
| WO | 2001056465 A1 | 8/2001 |
| WO | 02062211 A2 | 8/2002 |
| WO | 02093312 A2 | 11/2002 |
| WO | 2003043494 A1 | 5/2003 |
| WO | 2005018453 A1 | 3/2005 |
| WO | 2005074369 A2 | 8/2005 |
| WO | 2006004430 A2 | 1/2006 |
| WO | 2006012694 A1 | 2/2006 |
| WO | 2007102709 A1 | 9/2007 |
| WO | 2008114291 A1 | 9/2008 |
| WO | 2008140780 A1 | 11/2008 |
| WO | 2009003170 A1 | 12/2008 |
| WO | 2009008968 A1 | 1/2009 |
| WO | 2011025322 A2 | 3/2011 |
| WO | 2012128801 A1 | 9/2012 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2014163976 A1 | 10/2014 |
| WO | 2015026744 A1 | 2/2015 |
| WO | 2015065298 A1 | 5/2015 |
| WO | 2015082555 A1 | 6/2015 |
| WO | 2016154318 A1 | 9/2016 |
| WO | WO-2016151364 A1 * | 9/2016 ........... A61B 5/4842 |
| WO | 2017030781 A1 | 2/2017 |
| WO | 2017166074 A1 | 5/2017 |
| WO | 2017091691 A1 | 6/2017 |
| WO | 2017165238 A1 | 9/2017 |
| WO | 2018027080 A1 | 2/2018 |
| WO | 2018081795 A1 | 5/2018 |
| WO | 2018171853 A1 | 9/2018 |
| WO | 2019022706 A1 | 1/2019 |
| WO | 2019143940 A1 | 7/2019 |
| WO | 2020014710 A2 | 1/2020 |
| WO | 2020075190 A1 | 4/2020 |
| WO | 2020130979 A1 | 6/2020 |
| WO | 2020149815 A2 | 7/2020 |
| WO | 2020229705 A1 | 11/2020 |
| WO | 2020245727 A1 | 12/2020 |
| WO | 2020249855 A1 | 12/2020 |

(56) References Cited

FOREIGN PATENT DOCUMENTS

| | | | |
|---|---|---|---|
| WO | 2020252599 | A1 | 12/2020 |
| WO | 2020256577 | A1 | 12/2020 |
| WO | 2021021447 | A1 | 2/2021 |
| WO | 2021022003 | A1 | 2/2021 |
| WO | 2021038980 | A1 | 3/2021 |
| WO | 2021055427 | A1 | 3/2021 |
| WO | 2021061061 | A1 | 4/2021 |
| WO | 2021090267 | A1 | 5/2021 |
| WO | 2021138620 | A1 | 7/2021 |
| WO | 2021216881 | A1 | 10/2021 |
| WO | 2021236961 | A1 | 11/2021 |
| WO | 2022047006 | A1 | 3/2022 |
| WO | 2022092493 | A1 | 5/2022 |
| WO | 2022092494 | A1 | 5/2022 |
| WO | 2022212883 | A1 | 10/2022 |
| WO | 2022212921 | A1 | 10/2022 |
| WO | 2022216498 | A1 | 10/2022 |
| WO | 2022251420 | A1 | 12/2022 |
| WO | 2023008680 | A1 | 2/2023 |
| WO | 2023008681 | A1 | 2/2023 |
| WO | 2023022319 | A1 | 2/2023 |
| WO | 2023022320 | A1 | 2/2023 |
| WO | 2023052695 | A1 | 4/2023 |
| WO | 2023091496 | A1 | 5/2023 |
| WO | 2023215155 | A1 | 11/2023 |
| WO | 2023230075 | A1 | 11/2023 |
| WO | 2024013267 | A1 | 1/2024 |
| WO | 2024107807 | A1 | 5/2024 |

OTHER PUBLICATIONS

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https://towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience.com/natural-language-processing-nlp-for-machine-learning-d44498845d5b.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Ahmed et al., "Artificial Intelligence With Multi-Functional Machine Learning Platform Development for Better Healthcare and Precision Medicine," Database (Oxford), 2020, pp. 1-35, vol. 2020.

Davenport et al., "The Potential for Artificial Intelligence in Healthcare," Future Healthcare Journal, 2019, pp. 94-98, vol. 6, No. 2.

Gerbild et al., "Physical Activity to Improve Erectile Dysfunction: A Systematic Review of Intervention Studies," Sexual Medicine, 2018, 15 pages.

Barrett et al., "Artificial intelligence supported patient self-care in chronic heart failure: a paradigm shift from reactive to predictive, preventive and personalised care," EPMA Journal (2019), pp. 445-464.

Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.

Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.

Thomas et al., "Home-Based Cardiac Rehabilitation," Circulation, 2019, pp. e69-e89, vol. 140.

Thomas et al., "Home-Based Cardiac Rehabilitation," Journal of the American College of Cardiology, Nov. 1, 2019, pp. 133-153, vol. 74.

Thomas et al., "Home-Based Cardiac Rehabilitation," HHS Public Access, Oct. 2, 2020, pp. 1-39.

Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.

Chen et al., "Home-based cardiac rehabilitation improves quality of life, aerobic capacity, and readmission rates in patients with chronic heart failure," Medicine, 2018, pp. 1-5 vol. 97:4.

Lima de Melo Ghisi et al., "A systematic review of patient education in cardiac patients: Do they increase knowledge and promote health behavior change?," Patient Education and Counseling, 2014, pp. 1-15.

Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.

Beene et al., "AI and Care Delivery: Emerging Opportunities for Artificial Intelligence to Transform How Care Is Delivered," Nov. 2019, American Hospital Association, pp. 1-12.

Jeong et al., "Computer-assisted upper extremity training using interactive biking exercise (iBikE) platform," Sep. 2012, pp. 1-5, 34th Annual International Conference of the IEEE EMBS.

Hcl Fitness, Hci Fitness PhysioTrainer Pro, 2017, retrieved on Aug. 19, 2021, 7 pages, https://www.amazon.com/HCI-Fitness-Physio Trainer-Electronically-Controlled/dp/B0759YMW78/.

International Searching Authority, International Preliminary Report on Patentability of International Application No. PCT/US2017/50895, Date of Mailing Dec. 11, 2018, 52 pages.

International Searching Authority, Search Report and Written Opinion for International Application No. PCT/US2017/50895, Date of Mailing Jan. 12, 2018, 6 pages.

International Searching Authority, Search Report and Written Opinion for International Application No. PCT/US2020/021876, Date of Mailing May 28, 2020, 8 pages.

International Searching Authority, Search Report and Written Opinion for International Application No. PCT/US2020/051008, Date of Mailing Dec. 10, 2020, 9 pages.

International Searching Authority, Search Report and Written Opinion for International Application No. PCT/US2020/056661, Date of Mailing Feb. 12, 2021, 12 pages.

International Searching Authority, Search Report and Written Opinion for International Application No. PCT/US2021/032807, Date of Mailing Sep. 6, 2021, 11 pages.

Matrix, R3xm Recumbent Cycle, retrieved on Aug. 4, 2020, 7 pages, https://www.matrixfitness.com/en/cardio/cycles/r3xm-recumbent.

ROM3 Rehab, ROM3 Rehab System, Apr. 20, 2015, retrieved on Aug. 31, 2018, 12 pages, https://vimeo.com/125438463.

International Search Report and Written Opinion for PCT/US2023/014137, dated Jun. 9, 2023, 13 pages.

Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.

Abedtash, "An Interoperable Electronic Medical Record-Based Platform for Personalized Predictive Analytics", ProQuest LLC, Jul. 2017, 185 pages.

(56) References Cited

OTHER PUBLICATIONS

Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.

Androutsou et al., "A Smartphone Application Designed to Engage the Elderly in Home-Based Rehabilitation," Frontiers in Digital Health, Sep. 2020, vol. 2, Article 15, 13 pages.

Silva et al., "SapoFitness: A mobile health application for dietary evaluation," 2011 IEEE 13th International Conference on U e-Health Networking, Applications and Services, Columbia, MO, USA, 2011, 6 pages.

Wang et al., "Interactive wearable systems for upper body rehabilitation: a systematic review," Journal of NeuroEngineering and Rehabilitation, 2017, 21 pages.

Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.

Nijjar et al., "Randomized Trial of Mindfulness-Based Stress Reduction in Cardiac Patients Eligible for Cardiac Rehabilitation," Scientific Reports, 2019, 12 pages.

Lara et al., "Human-Robot Sensor Interface for Cardiac Rehabilitation," IEEE International Conference on Rehabilitation Robotics, Jul. 2017, 8 pages.

Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.

Zakari et al., "Are There Limitations to Exercise Benefits in Peripheral Arterial Disease?," Frontiers in Cardiovascular Medicine, Nov. 2018, vol. 5, Article 173, 12 pages.

You et al., "Including Blood Vasculature into a Game-Theoretic Model of Cancer Dynamics," Games 2019, 10, 13, 22 pages.

Jeong et al., "Computer-assisted upper extremity training using interactive biking exercise (iBikE) platform," Sep. 2012, 34th Annual International Conference of the IEEE EMBS, 5 pages.

Website for "Pedal Exerciser", p. 1, retrieved on Sep. 9, 2022 from https://www.vivehealth.com/collections/physical therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

Website for "ComfySplints Goniometer Knee", pp. 1-5, retrieved on Sep. 9, 2022 from https://www.comfysplints.com/product/knee-splints/.

Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.

Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.

Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.

Ahmed et al., "Artificial intelligence with multi-functional machine learning platform development for better healthcare and precision medicine," Database, 2020, pp. 1-35.

Davenport et al., "The potential for artificial intelligence in healthcare," Digital Technology, Future Healthcare Journal, 2019, pp. 1-5, vol. 6, No. 2.

Website for "OxeFit XS1", pp. 1-3, retrieved on Sep. 9, 2022 from https://www.oxefit.com/xs1.

Website for "Preva Mobile", pp. 1-6, retrieved on Sep. 9, 2022 from https://www.precor.com/en-us/resources/introducing-preva-mobile.

Website for "J-Bike", pp. 1-3, retrieved on Sep. 9, 2022 from https://www.magneticdays.com/en/cycling-for-physical-rehabilitation.

Website for "Excy", pp. 1-12, retrieved on Sep. 9, 2022 from https://excy.com/portable-exercise-rehabilitation-excy-xcs-pro/.

Website for "OxeFit XP1", p. 1, retrieved on Sep. 9, 2022 from https://www.oxefit.com/xp1.

Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.

Chrif et al., "Control design for a lower-limb paediatric therapy device using linear motor technology," Article, 2017, pp. 119-127, Science Direct, Switzerland.

Robben et al., "Delta Features From Ambient Sensor Data are Good Predictors of Change in Functional Health," Article, 2016, pp. 2168-2194, vol. 21, No. 4, IEEE Journal of Biomedical and Health Informatics.

Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.

Warburton et al., "International Launch of the Par-•Q+ and ePARmed-•X+ Validation of the PAR-•Q+ and ePARmed••X+," Health & Fitness Journal of Canada, 2011, 9 pages, vol. 4, No. 2.

Jeong et al., "Remotely controlled biking is associated with improved adherence to prescribed cycling speed," Technology and Health Care 23, 2015, 7 pages.

Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.

Blasiak et al., "Curate.AI: Optimizing Personalized Medicine with Artificial Intelligence,"SLAS TECHNOLOGY: Translating Life Sciences Innovation, 2020, 11 pages.

Abidi, Samina; A Knowledge-Modeling Approach to Integrate Multiple Clinical Practice Guidelines to Provide Evidence-Based Clinical Decision Support for Managing Comorbid Conditions; Journal of Medical Systems 41.12: 1-19. Springer Nature B.V. (Dec. 2017) (Year: 2017).

Fuller, Carole G.; Diagnosis and treatment considerations with comorbid developmentally disabled populations; Journal of Clinical Psychology 54.1: 1-10. John VWey and Sons Inc. (Jan. 1998) (Year: 1998).

He, Jianxing et al. The practical implementation ofartificial intelligence technologies in medicine. Nature Medicine; New York vol. 25, Iss. 1. Jan. 2019. (Year: 2019).

CG. Acampora, D. J. Cook, P. Rashidi and A. V. Vasilakos, "A Survey on Ambient Intelligence in Healthcare," in Proceedings of the IEEE, vol. 101, No. 12, pp. 2470-2494, Dec. 2013, doi: 10.1109/JPROC.2013.2262913. (Year: 2013).

H. Demirkan, "A Smart Healthcare Systems Framework," in IT Professional, vol. 15, No. 5, pp. 38-45, Sep.-Oct. 2013, doi: 10.1109/MITP.2013.35. (Year: 2013).

W. Rashwan, J. Fowler and A. Arisha, "A Multl-Method Scheduling Framework for Medical Staff," 2018 Winter Simulation Conference (WSC), Gothenburg, Sweden, pp. 1464-1475, doi: 10.1109/WSC.2018.8632247. (Year: 2018.

Marios et al., "The effect of tele-monitoring on exercise training adherence, functional capacity, quality of life and glycemic control in patients with type II diabetes," Journal of Sports Science and Medicine, Mar. 2012, vol. 11, 6 pages.

* cited by examiner

| | Patients | | | | | | Tina Turner CLINICIAN | |
|---|---|---|---|---|---|---|---|---|
| | 🔍 Patient Name | | | + Add Patient | | | | |
| | NAME | PROCEDURE | POST-OP DAY | PAIN | ROM | BIKE | LOCKED | ALERTS |
| | Hunt, Kevin | Left leg surgery, daily | 22 | 0 | | ● | | |
| | Conner, Karen | left leg, continuous | 22 | 0 | | | | ◆ |
| | Hayes, Simone | Ut ut quia aspernatur autem. | 13 | 0 | | | | |
| | Smith, Emily | right leg, daily, PDT | 22 | 0 | | | | ◆ |
| | Bolton, Olivia | | 5 | 0 | | | | |
| | Dee, Sandra | left leg, daily | 15 | 0 | | | | ◆ |
| | Nader, Kyle | left leg, continuous | 15 | 0 | | | | |

ROM3 Rehab,LLC. | 1(888) 374-0855 | Privacy Policy | Disclaimer | Contact Us

Create Profile

Please complete the required information in the below

First name

✉ E-mail address

Last name

Password ●

Practice name

Confirm Password ●

[ Create Account ]

FIG. 7

Team Management

| Team Member | E-mail address | Phone number | Role | Specialty | Actions |
|---|---|---|---|---|---|
| Tina Turner | brooke.davis@rom3rehab.com | (617) 555-1299 | Clinician | Leg and Knee Outpatient Rehab | [Edit] [Archive] |
| Dana Elliott | d@e.com | | Clinician | | [Edit] [Archive] |

[Add New Team Member]

FIG. 8

Edit Team Member

| Team Member | Permission |
|---|---|

Role
Clinician — 242

Prefix
Ms

First Name
Tina

LastName
Turner

Speciality
Leg and KneeOutpaient Rehab

} 244

Q Patient Name

+ Add Patient

✓ Sam steele
PRACTICE

Q Patient Name

+ Add Patient

✔ Sam steele
PRACTICE

Edit Team Member

Team Member   Permission

Organization
Steele Suite Office

Email
brooke.davis@rom3rehab.com

Password
●

Office Phone
(617) 555-1299

Mobile Phone
(617) 555-2300

} 244

Skip    Save and Continue

| Q Patient Name | | + Add Patient | ✓ Sam steele PRACTICE |

Edit Team Member

Team Member   Permission

| Permission | Allow |
|---|---|
| Add Clinician | ☑ —262 |
| Edit Clinician | ☑ —264 |
| View Clinician | ☑ —266 |
| Add Staff | ☑ |
| Edit Staff | ☑ |
| View Staff | ☑ |
| Add Patient | ☑ |
| Edit Patient | |

FIG. 11

Edit Team Member

Patient Name

+ Add Patient

✓ Sam steele
PRACTICE

Team Member   Permission

| | |
|---|---|
| View Patient Personal Data | ☑ |
| View Patient Medical Data | ☑ |
| View Patient List | ☑ |
| View Patient Dashboard | ☑ |
| Add Treatment Plan | ☑ |
| Edit Treatment Plan | ☑ |
| View Treatment Plan | ☑ |

} 282

Cancle    Save and Finish 20, 280

Q Patient Name _____

+ Add Patient   ❤ Tina Turner CLINICIAN

Patient Information

Personal Information   Procedure Details   Devices

First Name
Kayli

Last Name
Hudson

Date of Birth
02/27/1965

Address
31681 Bosco Mews

City
East Jesse

State
Wisconsin

[Add a Photo] — 324

Patient Name

+ Add Patient

Tina Turner
CLINICIAN

Patient Information

Personal Information   Procedure Details   Devices

Clinician
Turner, Tina
Procedure — 342
Knee surgery
Procedure Date
10/23/2019          344
Treatment Start Date
10/23/2019
Procedure Leg
Left

FIG. 17

Patient Information

Personal Information  Procedure Details  Devices

Treatment Mode
Daily Session

Primary Daignosis (ICD10)
Quo quia sit voluptatem

Primary DME Code
123456789

Pain Medication
Iste corporis laborum unlla

Notes
Maiores cumque id error

} 344

Save & Continue

Q Patient Name

+ Add Patient

✓ Tina Turner
CLINICIAN 20, 350

Patient Information

Personal Information     Procedure Details     Devices

Motor
SN-032
45:64:86:84:68:44

Pedals
PD-045
FA:48:BE:46:84:82

Accuangle
AC-103
F8:FA:48:68:45:6F

Accustep
ST-007
A4:8B:68:46:8E:46

} 362

[ Finish ]

FIG. 19

SYSTEM FOR REMOTE TREATMENT UTILIZING PRIVACY CONTROLS

CROSS-REFERENCES TO RELATED APPLICATIONS

This application is a divisional of patent application Ser. No. 17/075,049 filed Oct. 20, 2020, titled "System for Remote Treatment Utilizing Privacy Controls," which claims priority to and the benefit of U.S. Provisional Application Patent Ser. No. 62/931,278 filed Nov. 6, 2019, titled "System for Remote Treatment Utilizing Privacy Controls," the entire disclosures of which are hereby incorporated by reference for all purposes.

BACKGROUND

Patients may use treatment apparatuses for any suitable purpose, such as rehabilitation of a body part, pre-habilitation of a body part, strengthening a body part, exercising a body part, and the like.

SUMMARY

A method for a clinician user interface generated by a computer is provided. The clinician user interface comprises a protocol management display presenting a treatment plan, with the treatment plan comprising a plurality of treatment protocols. The clinician user interface also comprises a plan modification control configured to modify the plurality of treatment protocols of the treatment plan, and a login interface configured to enable a person to access the clinician user interface by providing a credential associated with one of a plurality of user accounts. Each of the plurality of user accounts has a corresponding set of permissions controlling access to patient data on the clinician user interface.

A computer-implemented system for a clinician user interface generated by a computer is also provided. The clinician user interface comprises a protocol management display presenting a treatment plan, with the treatment plan comprising a plurality of treatment protocols. The clinician user interface also comprises a plan modification control configured to modify the plurality of treatment protocols of the treatment plan, and a login interface configured to enable a person to access the clinician user interface by providing a credential associated with one of a plurality of user accounts. Each of the plurality of user accounts has a corresponding set of permissions controlling access to patient data on the clinician user interface.

A clinician user interface generated by a computer is also provided. The clinician user interface comprises a protocol management display presenting a treatment plan, with the treatment plan comprising a plurality of treatment protocols. The clinician user interface also comprises a plan modification control configured to modify the plurality of treatment protocols of the treatment plan, and a login interface configured to enable a person to access the clinician user interface by providing a credential associated with one of a plurality of user accounts. Each of the plurality of user accounts has a corresponding set of permissions controlling access to patient data on the clinician user interface.

BRIEF DESCRIPTION OF THE DRAWINGS

For a detailed description of example embodiments, reference will now be made to the accompanying drawings in which:

FIG. 5 shows an example embodiment of an overview display of a clinician interface;

FIG. 6 shows an example embodiment of an overview display of a clinician interface with a patient detail overlay;

FIG. 7 shows an example embodiment of an account creation display of a clinician interface;

FIG. 8 shows an example embodiment of a team management display of a clinician interface;

FIG. 9 shows an example embodiment of a team member display of a clinician interface for modifying team member data;

FIG. 10 shows an example embodiment of another team member display of a clinician interface for modifying team member data;

FIG. 11 shows an example embodiment of another team member display of a clinician interface for modifying team member data;

FIG. 12 shows an example embodiment of another team member display of a clinician interface for modifying team member data;

FIG. 13 shows an example embodiment of a notifications settings display of a clinician interface;

FIG. 15 shows an example embodiment of a patient data display of a clinician interface for modifying patient personal information;

FIG. 17 shows an example embodiment of a medical data display of a clinician interface for modifying patient procedure details information;

FIG. 18 shows an example embodiment of another medical data display of a clinician interface for modifying patient procedure details information;

FIG. 19 shows an example embodiment of a device data display of a clinician interface;

NOTATION AND NOMENCLATURE

Figure 1:
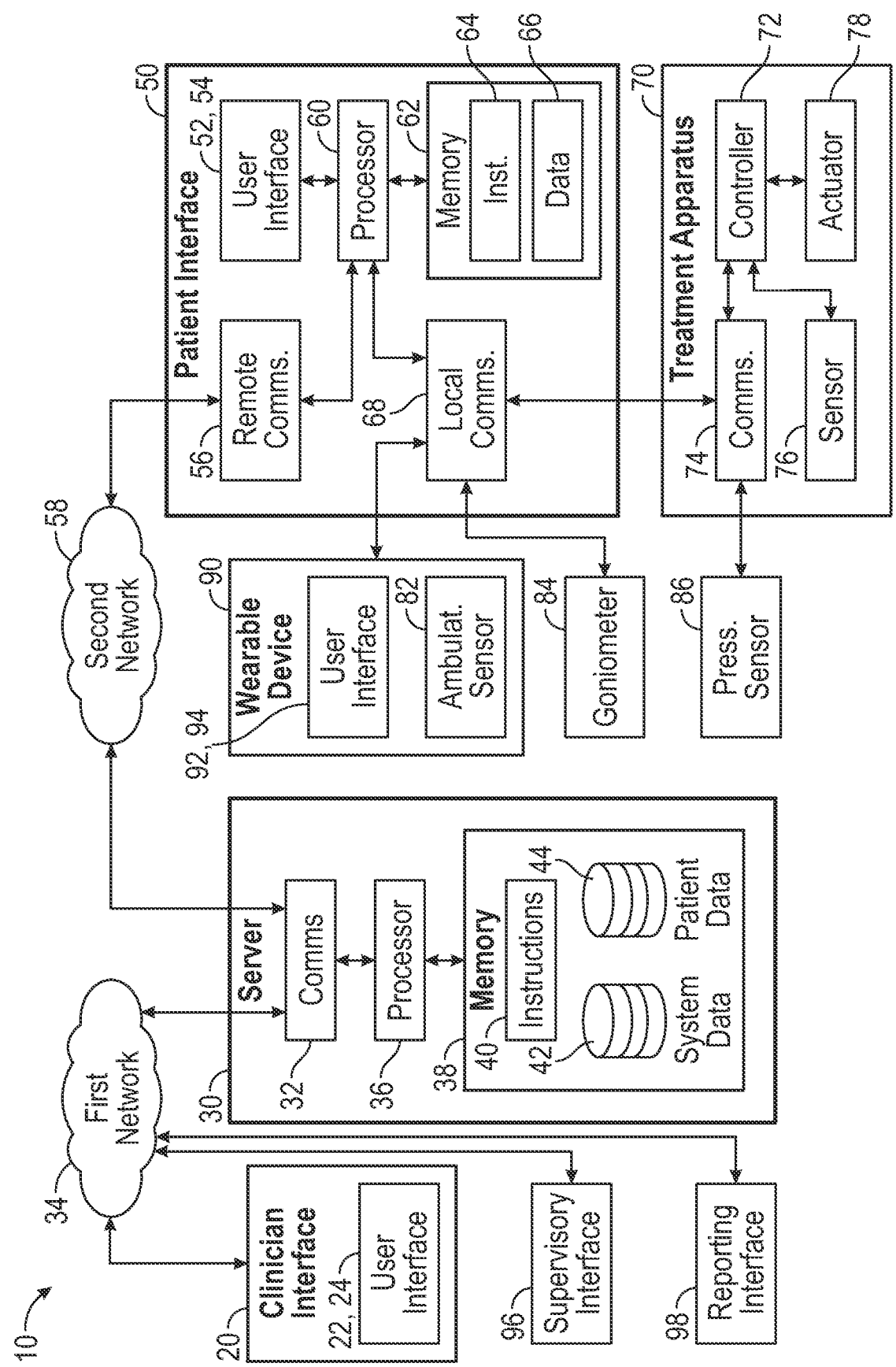
FIG. 1 shows a block diagram of an embodiment of a computer implemented system for managing a treatment plan.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

DETAILED DESCRIPTION

The following discussion is directed to various embodiments of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Regulatory frameworks dealing with the practice of medicine have only recently begun to allow telemedicine, or, alternatively a medical practice wherein the patient is virtually seen, diagnosed, prescribed treatments, etc. by a clinician remote from the patient in time and/or physical distance. In light of such recent developments in regulatory frameworks, telemedicine systems using an integrated set of access controls and a privacy enhancing technology (PET) engine executing privacy enhancing technologies to ensure patient privacy have not been addressed heretofore. Telemedicine, including remote physical therapy, presents a number of new challenges for protecting patient data and for compliance with patient privacy regulations such as the Health Insurance Portability and Accountability Act (HIPAA), the California Consumer Privacy Act (CCPA), or the General Data Protection Regulation (GDPR). Specifically, the present disclosure provides a unique combination of computerized access controls with PETs to enable a novel system 10 engineered to provide information for practicing remote physical therapy by a patient separated from a supervising clinician in time and/or physical distance. More specifically, the system 10 of the present disclosure incorporates a PET engine and user access controls to provide information tailored for use by different individuals, including clinicians, patients, practice managers, and staff members. The system 10 of the present disclosure, thereby, enables remote physical therapy, via a telemedicine session between one or more computing devices (e.g., a patient, a clinician, practice manager, staff members, etc.) compliant with privacy regulations and other regulatory frameworks that pertain to the practice of medicine.

In some embodiments, the PET engine may be implemented in computer instructions stored in one or more memory devices of one or more servers and executed by one or more processing devices of the one or more servers. The one or more servers may be included in distributed, cloud-based computing system. The PET engine may execute one or more machine learning models trained to use one or more privacy enhancing technologies (PETs) to control access to PII. The machine learning models may be trained with training data that maps inputs with certain outputs, such that the machine learning models are trained to identify pattern in data that should be de-identified, re-identified, protected, removed, stored, modified, etc. The training of the machine learning models may be iteratively performed to dynamically change based on certain regulations, laws, and/or protocols that are enacted or de-enacted. Accordingly, the PET engine enables dynamically learning and maintaining up-to-date machine learning models based on the current regulations, laws, and/or protocols pertaining to data privacy.

FIG. 1 shows a block diagram of a computer-implemented system 10, hereinafter called "the system" for managing a treatment plan. The treatment plan includes one or more treatment protocols, and each treatment protocol includes one or more sessions. Each session comprises several session periods, with each session period including a particular activity for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery.

The system 10 includes a clinician interface 20 for a clinician, such as a doctor, a nurse, a physical therapist, or a technician, to use to review and to configure various aspects of a treatment plan for use in treating a patient. The clinician interface 20 includes a clinician input device 22 and a clinician display 24, which may be collectively called a clinician user interface 22, 24. The clinician input device 22 may include one or more of a keyboard, a mouse, a trackpad, or a touch screen, for example. Alternatively or additionally, the clinician input device 22 may include one or more microphones and voice-based functionalities, with hardware and/or software configured to interpret spoken instructions by the clinician by using the one or more microphones. The clinician input device 22 may include functionality provided by or similar to existing voice-based assistants such as Siri by Apple, Alexa by Amazon, Google Assistant, or Bixby by Samsung. The clinician input device 22 may include other hardware and/or software components. The clinician input device 22 may include one or more general purpose devices and/or special-purpose devices.

The clinician display 24 may take one or more different forms including, for example, a computer monitor or display screen on a tablet, smartphone, or a smart watch. The clinician display 24 may include other hardware and/or software components such as a projector, virtual reality capability, or augmented reality capability etc. The clinician display 24 may incorporate various different visual, audio, or other presentation technologies. For example, the clinician display 24 may include a non-visual display, such as an audio signal, which may include spoken language and/or other sounds such as tones, chimes, and/or melodies which may signal different conditions and/or directions. The clinician display 24 may comprise one or more different display screens presenting various data and/or interfaces or controls for use by the clinician. The clinician display 24 may include graphics, which may be presented by a web-based interface and/or by a computer program or application (App.).

The system 10 also includes a server 30 configured to store and to provide data related to managing the treatment plan. The server 30 may include one or more computers and may take the form of a distributed and/or virtualized computer or computers. In some embodiments, the server 30 may generate aspects of the clinician display 24 for presentation by the clinician interface 20. For example, the server 30 may include a web server configured to generate the display screens for presentation upon the clinician display 24. In some embodiments, the clinician display 24 may be configured to present a virtualized desktop that is hosted by the server 30. The server 30 also includes a first communication interface 32 configured to communicate with the clinician interface 20 via a first network 34. In some embodiments, the first network 34 may include a local area network (LAN), such as an Ethernet network. In some embodiments, the first network 34 may include the Internet, and communications between the server 30 and the clinician interface 20 may be secured via encryption, such as, for example, by using a virtual private network (VPN). In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36.

The server 30 is configured to store data regarding the treatment plan. For example, the memory 38 includes a system data store 42 configured to hold system data, such as data pertaining to treatment plans for treating one or more patients. The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

The server 30 is configured to execute and be controlled by a privacy-enhancing technology (PET) engine that uses one or more privacy-enhancing technologies that control access to personally identifiable information (PII) associated with the patient. Controlling access may refer to defining access, enabling access, disabling access, etc. In some embodiments, the PET engine is configured to pseudonymize or anonym ize the PII associated with the patient. In some embodiments, the PET engine may enable de-identification and/or re-identification of the PII associated with the patient. PETs, as used by the PET engine herein, may include, without limitation, differential privacy, homomorphic encryption, public key encryption, digital notarization, pseudonymization, pseudonymisation, anonymization, anonymisation, digital rights management, k-anonymity, I-diversity, synthetic data creation, suppression, generalization, identity management, and the introduction of noise into existing data or systems.

In some embodiments, the computer-implemented system 10 is configured to maintain a plurality of user accounts, with each of the user accounts having an account type associated therewith, and each of the plurality of user accounts has a corresponding set of permissions enabling an owner of the user account to access the patient data. The computer-implemented system 10 may be configured to restrict access to each of the user accounts using login credentials.

The account types may include a super-administrator account type. A user account having the super-administrator account type may have unrestricted access to the patient data, or at least a greater access to the patient data than any other one of the account types. A user having the super-administrator account type can also be a controlling entity with respect to the granting or revocation of access to the P II or any portion thereof and with respect to which other entities are granted or denied such access, including the level of such access granted or denied, and, last with respect to any other conditions, such as time, location, identity, etc. which may further be used by a PET engine to grant or deny any of the types of access contemplated.

The account types may also include a practice manager account type. In some embodiments, the practice manager may have access to all patient data for patients assigned to the practice manager. In some embodiments, the practice manager may have access to view and/or to modify at least some of the patient data for patients assigned to the practice manager. More specifically, the practice manager may have access to some, but not all, patient data for patients assigned to the practice manager. For example, the practice manager may have access to biographical and/or scheduling data within the patient data, but the practice manager may not have access to view and/or modify to certain types of medical data within the patient data. In some embodiments, the practice manager may not have any access to patient data. For example, the practice manager may be limited to managing user accounts of other team members, such as clinicians and/or staff members.

The account types may also include a clinician account type. A user account having the clinician account type may have access to view and/or to modify at least some of the patient data for patients assigned to the owner of the user account having the clinician account type. For example, a particular doctor may have a user account with the clinician account type. The particular doctor may have access to view and modify patient data of patients that are assigned to that particular doctor. However, the particular doctor may not have access to patient data regarding other patients that are not assigned to that particular doctor.

The account types may also include a staff member account type. The staff member account type may be used, for example, by a nurse or a physical therapist. A user account having the staff member account type may have access to view and/or to modify at least some of the patient data for patients assigned to the owner of the user account having the staff member account type. For example, a particular nurse may have a user account with the staff member account type. The particular nurse may have access to view and modify patient data of patients assigned to that particular nurse. However, the particular doctor may not have access to patient data regarding other patients not assigned to that particular nurse.

The account types may also include a patient account type. A user account having the patient account type may have access to view at least some of the patient data associated with their own user account. However, the user account having the patient account type may not have access to modify any patient data.

In some embodiments, user accounts having one or more of the account types may have abilities to designate another one of the user accounts as having predetermined account types. For example, a user account having the practice manager account type may have the ability to designate another user account as having the clinician account type. Additionally or alternatively, the user account having the practice manager account type may have the ability to designate another user account as having the staff member or patient user type. In another example, a user account having the clinician account type may have the ability to designate another user account as having the staff member account type. Additionally or alternatively, the user account having the clinician account type may have the ability to designate another user account as having the patient user type.

The system 10 also includes a patient interface 50 configured to communicate information to a patient and to receive feedback from the patient. Specifically, the patient interface 50 includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

As shown in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. More specifically, the regimen may be a physical rehabilitation regimen for improving strength and/or range of motion of the body part. The body part may include, for example, a spine, a hand, a foot, a knee, or a shoulder. The body part may include a part of a joint, a bone, or a muscle group, such as one or more vertebrae or a ligament. As shown in FIG. 1, the treatment apparatus 70 includes a controller 72, which may include one or more processors, computer memory, and/or other components. The treatment apparatus 70 also includes a fourth communication interface 74 configured to communicate with the patient interface 50 via the local communication interface 68. The treatment apparatus 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the patient interface 50. The goniometer 84 measures a position of the patient's body part. More specifically, the goniometer 84 measures an angle of the body part, particularly where the body part is a joint. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 also includes a wearable device 90 configured to be worn or carried on the patient's person. The wearable device 90 may take one of several different forms such as, for example, a smart watch, a wristband, a pendant, or a smartphone. The wearable device 90 may include a means of attachment, such as a pin, a belt clip, a strap, or a lanyard, to facilitate the device's being worn or carried by the patient. In some embodiments, and as shown in FIG. 1, the wearable device 90 includes the ambulation sensor 82. The wearable device 90 may include one or more other sensors, such as a heartrate sensor, a blood pressure sensor, or a pulse oximeter. The ambulation sensor 82 or another one of the sensors in the wearable device 90 may be configured to monitor one or more factors that indicate an activity level of the patient. The patient's activity level could be used to determine a quantity and/or quality of exercise performed by the patient. The patient's activity level could also be used to determine a quantity and/or quality of the patient's sleep.

The wearable device 90 includes a wearable input device 92 and a wearable display 94, which may be collectively called a wearable user interface 92, 94. The wearable input device 92 may include one or more devices, such as a keyboard, a mouse, a touch screen input, a gesture sensor, and/or a microphone and processor configured for voice recognition. The wearable display 94 may take one or more different forms including, for example, a display screen, and/or one or more lights or other indicators. The wearable display 94 may incorporate various different visual, audio, or other presentation technologies. For example, the wearable display 94 may include a non-visual display, such as a haptic or tactile device and/or an audio signal, which may include spoken language and/or other sounds such as tones, chimes, and/or melodies, and the non-visual display may signal different conditions and/or directions. The wearable display 94 may comprise one or more different display screens configured to present various data and/or interfaces or controls for use by the patient. The wearable display 94 may include graphics, which may be presented by a web-based interface and/or by a computer program or application (App.). The wearable user interface 92, 94 may be configured to present different types of information to the patient. For example, the wearable user interface 92, 94 may be configured to present a reminder when it is time for the patient to perform a rehabilitation session. The wearable user interface 92, 94 may allow the patient to track daily goals or to receive messages from a clinician, etc. This function of the wearable device 90 may be especially useful when the patient is away from the patient interface 50.

The system 10 shown in FIG. 1 also includes a supervisory interface 96 which may be similar or identical to the clinician interface 20. In some embodiments, the supervisory interface 96 may have enhanced functionality beyond what is provided on the clinician interface 20. The supervisory interface 96 may be configured for use by a person having responsibility for the treatment plan, such as an orthopedic surgeon.

The system 10 shown in FIG. 1 also includes a reporting interface 98 which may be similar or identical to the clinician interface 20. In some embodiments, the reporting interface 98 may have less functionality from what is provided on the clinician interface 20. For example, the reporting interface 98 may not have the ability to modify a treatment plan. Such a reporting interface 98 may be used, for example, by a biller to determine the use of the system 10 for billing purposes. In another example, the reporting interface 98 may not have the ability to display patient identifiable information, presenting only pseudonymized data and/or anonym ized data for certain data fields concerning a data subject and/or for certain data fields concerning a quasi-identifier of the data subject. Such a reporting interface 98 may be used, for example, by a researcher to determine various effects of a treatment plan on different patients.

In some embodiments, the patient interface 50 and the treatment apparatus 70 are each configured to operate from a patient location geographically separate from a location of the clinician interface 20. For example, the patient interface 50 and the treatment apparatus 70 may be used as part of an in-home rehabilitation system, which may be monitored remotely by using the clinician interface 20 at a centralized location, such as a clinic or hospital. In some embodiments, either or both of the patient interface 50 and/or the treatment apparatus 70 are configured to communicate with a remote computer, such as the server 30, to receive the treatment plan and to report back to the remote computer with data regarding performance by the patient in following the treatment plan.

Figure 2:
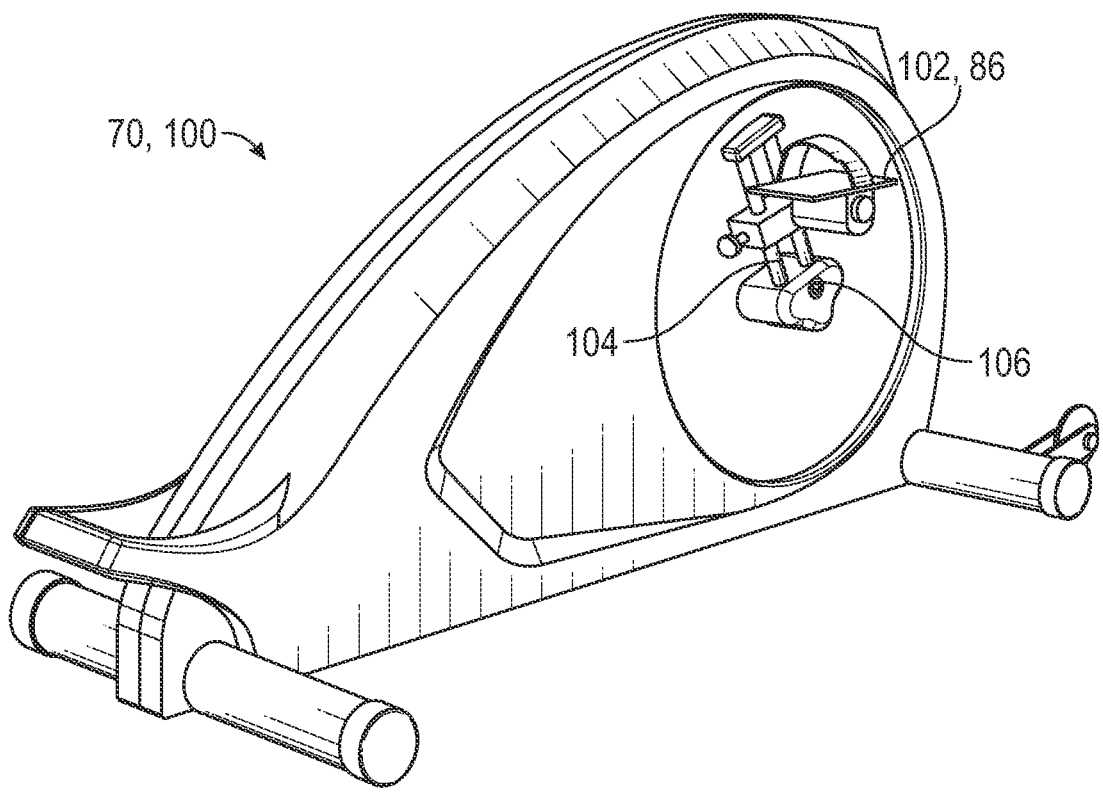
FIG. 2 shows a perspective view of an embodiment of a treatment apparatus.
Figure 3:
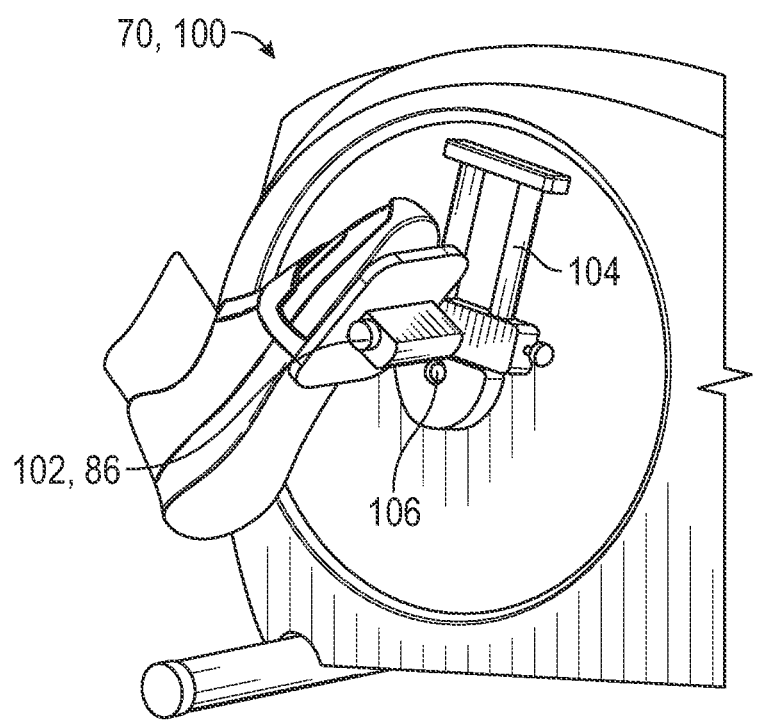
FIG. 3 shows a perspective view of a pedal of the treatment apparatus of FIG. 2.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 106 for measuring an amount of force applied by the patient on the pedal 106. The pressure sensor 86 may communicate wirelessly to the treatment apparatus 70 and/or to the patient interface 50.

Figure 4:
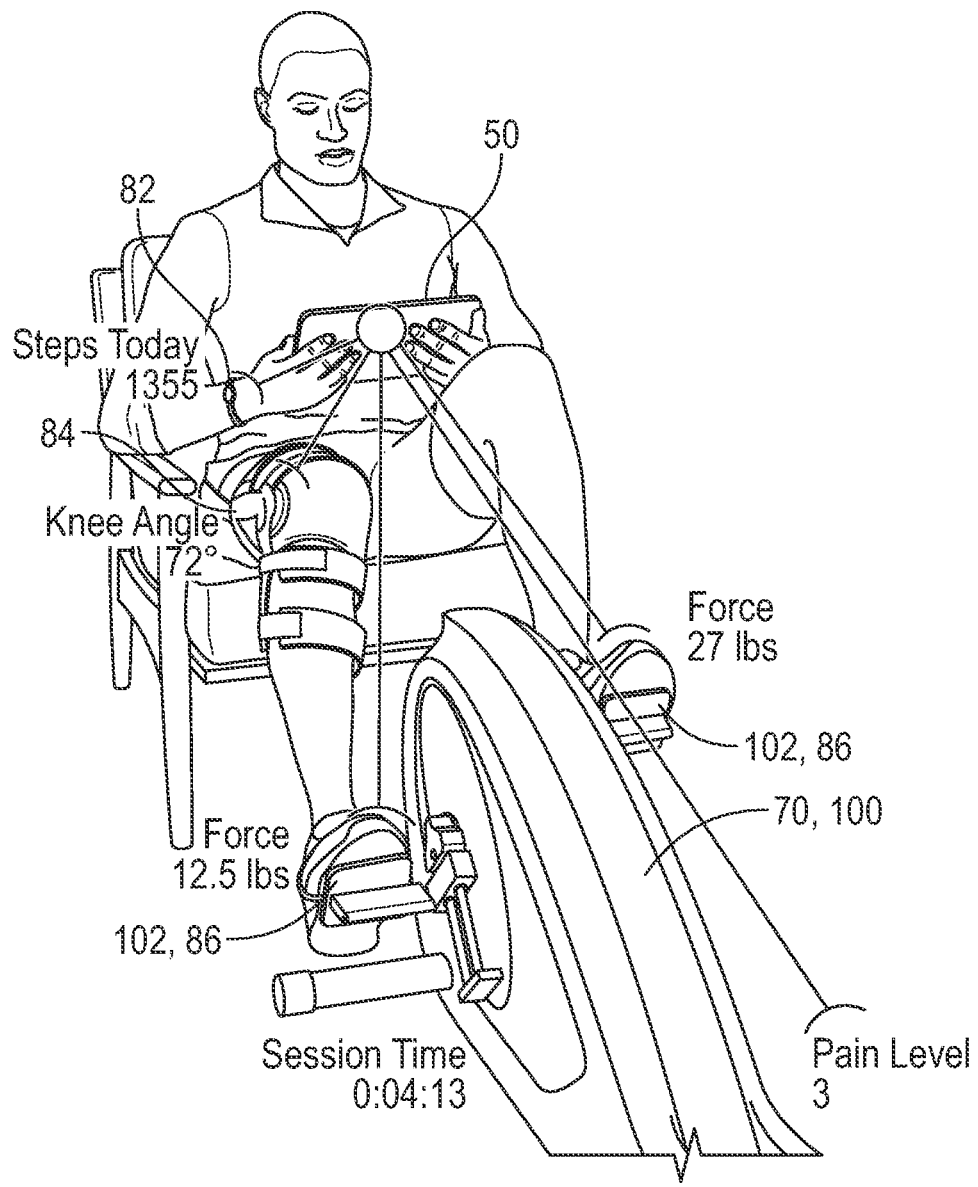
FIG. 4 shows a perspective view of a person using the treatment apparatus of FIG. 2.

FIG. 4 shows a person (a patient) using the treatment apparatus of FIG. 2, and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment apparatus 70. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72°", indicating that the goniometer 84 is measuring and transmitting that knee angle to the patient interface 50. FIG. 4 also shows a right side of one of the pedals 106 with a pressure sensor 86 showing "FORCE 12.5 lbs.,", indicating that the right pedal pressure sensor 86 is measuring and transmitting that force measurement to the patient interface 50. FIG. 4 also shows a left side of one of the pedals 106 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patent in response to a solicitation, such as a question, presented upon the patient interface 50.

FIG. 5 is an example embodiment of an overview display 110 of the clinician interface 20. Specifically, the overview display 110 presents summary information regarding each of a plurality of different patients. In some embodiments, and as shown on FIG. 5, the summary information includes an indicator showing a procedure performed upon each of the patients, temporal progress of the patient within the treatment plan (post-op day), an indicator of a last-reported pain level, range-of-motion (ROM) numbers, and an indicator showing if there are any alerts requiring special attention.

FIG. 5 also shows a header 112, which is shared with many or all of the other screens of the clinician interface 20. The header 112 includes a patient search input 113 whereby a user may quickly access patient data by entering the patient's name. The header 112 also includes an Add Patient control 114 in the form of a button. When pressed, the Add Patient control 114 causes the clinician interface 20 to enable a user to add a new patient to the system 10. The header 112 also includes a user account login control 116 presenting information regarding the user account currently logged-in to the clinician interface 20, and allowing a user to change the user account logged-in to the clinician interface 20. As shown in the example display on FIG. 5, the user account login control 116 includes a name 117 and a pictorial icon 118 associated with the user account currently logged-in to the clinician interface 20. The user account login control 118 also includes an account type indicator 119 of the account type (e.g., Clinician, Staff, Practice Manager, etc.) for the user account currently logged-in to the clinician interface 20.

Figure 6:
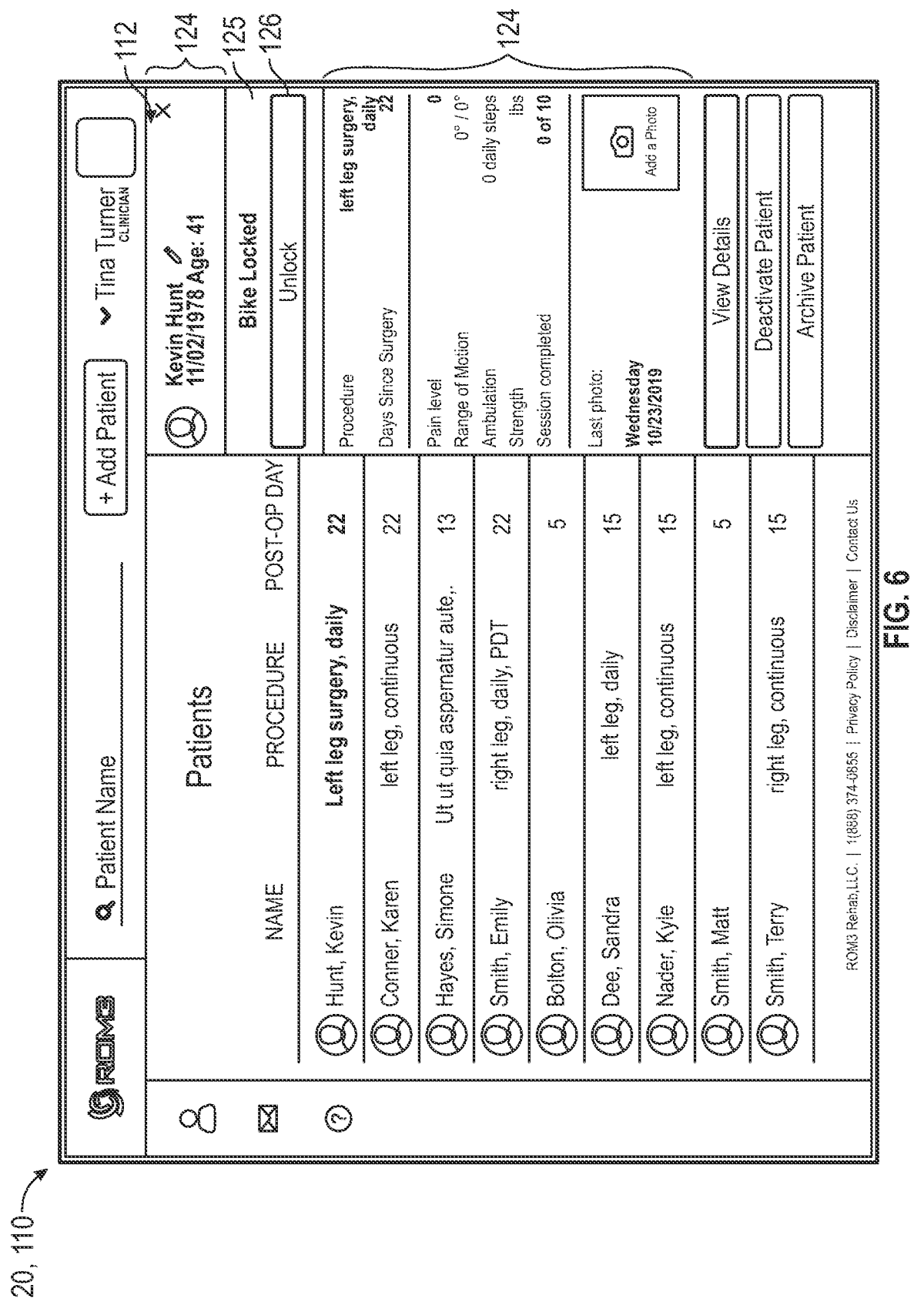

FIG. 6 shows an example embodiment of the overview display 110 of the clinician interface 20 with a patient detail overlay 122. The patient detail overlay 122 may take the form of a modal window or a popup window that overlies the overview display 120. Alternatively, the patient detail overlay 122 may be a separate display or screen on the clinician interface 20. In some embodiments, the patient detail overlay 122 may be presented in response to a user of the clinician interface 20 selecting one of the patients listed on the overview display 120. Alternatively or additionally, the patient detail overlay 122 for a particular patient may be presented in response to an occurrence of a triggering condition regarding that particular patient, such as the particular patient's treatment apparatus 70 being in a locked condition. The patient detail overlay 122 includes several patient profile data fields 124, each presenting corresponding data regarding the patient. The data patient profile data fields 124 of the patient detail overlay 122 may include, for example, name, age, date of birth, procedure for which the patient is being treated, days since surgery, last reported pain level, range of motion statistics, ambulation data, strength data, sessions completed within the treatment plan, a photograph of the patient, etc. The patient detail overlay 122 also includes an apparatus status display 125 and an apparatus unlock control 124 for a user of the clinician interface 20 to unlock or to re-enable the treatment apparatus 70.

FIG. 7 shows an example embodiment of an account creation display 200 of the clinician interface 20. The example account creation display 200 includes fields for data entry for use in creating a user account in the system 10.

FIG. 8 shows an example embodiment of a team management display 220 of the clinician interface 20. The team management display 220 presents a list of user accounts associated with a practice. The example team management display 220 includes team member records 222 for each of a plurality of user accounts having an account type associated with team members (e.g., clinician or staff member) who have access to the patient data by virtue of their position. For example, the team members may all be individuals that are clinicians or staff members of a particular practice managed by a practice manager. The team management display 220 may present the team member records 222 in rows or in other forms, such as tabular data, graphical icons, etc. As shown in the example team management display 220 of FIG. 8, the team member records 222 each include summary biographical information such as name, phone number, role (i.e., clinician or staff member), and specialty. The example team management display 220 includes an edit control 224, such as a button, associated with each of the team member records 222 for enabling a user to modify attributes of the associated team member. The example team management display 220 also includes an archive control 226, such as a button, associated with each of the team member records 222, for enabling a user to archive or to disable the associated team member. The edit control 224 and/or the archive control 226 may be available only for users having certain user types. For example, a user having the clinician user type may have the ability to modify or to archive accounts having the staff member user type, but the user having the clinician user type may not have the ability to modify or to archive user accounts having user accounts that have the clinician user type. The example team management display 220 also includes a new user add control 228, which may take the form of a button, configured to add a new user account or to associate an account type with a new or an existing user account.

FIG. 9 shows an example embodiment of a first team member display 240 of the clinician interface 20 for modifying team member data. Using an edit control 224 on the team management display 220, the first team member display 240 may be invoked for a selected team member. The example first team member display 240 presents an account type control input 242 for modifying an account type associated with the selected user account. The account type control input 242 is shown in FIG. 9 as being a drop-down selector type control, although the account type control input 242 may take any one of several different forms including radio buttons or a text entry field. The example first team member display 240 also presents other data entry fields 244 for a user to input various data regarding a team member. The data entry fields 244 may include, for example, inputs for name and specialty.

FIG. 10 shows an example embodiment of a second team member display 250 of the clinician interface 20 for modifying team member data. The second team member display 250 may be a continuation of the first team member display 240. The example second team member display 250 includes additional data entry fields 244 for additional data regarding the team member, such as organization, email address, and phone numbers. The example second team member display 250 also includes a skip button 246 for allowing a user to bypass entering information into the data entry fields 244. The example second team member display 250 also includes a "save and continue" button 248 for saving information entered into the data entry fields 244 to the system data store 42 for association with the user account of the selected team member.

FIG. 11 shows an example embodiment of a third team member display 260 of the clinician interface 20 for modifying team member data. The third team member display 260 presents a plurality of permission controls, with each of the permission controls configured to modify an ability of the selected user account to perform an action or to view or to modify a subset of the patient data. Specifically, the third team member display 260 includes an "add clinician" permission control 262 in the form of a check box. The "add clinician" permission control 262 enables the selected user account to add a user account having the clinician account type or to designate another one of the user accounts as the clinician account type.

The third team member display 260 also includes a plurality of account permission controls associated with a given account type. For example, the account permission controls include an "edit clinician" permission control 264 in the form of a check box. The "edit clinician" permission control 264 enables the selected user account to modify a user account having the clinician account type. The account permission controls also include a "view clinician" permission control 266 in the form of a check box. The "view clinician" permission control 266 enables the selected user account to view one or more non-public attributes of a user account having the clinician account type. The account permission controls 262, 264, 266 may take other forms such as, for example, radio buttons or a drop-down selector. The third team member display 260 includes add/edit/view account permission controls (not labeled) for other account types including staff member and patient.

FIG. 12 shows an example embodiment of a fourth team member display 280 of the clinician interface 20 for modifying team member data. Specifically, the example fourth team member display 280 includes a plurality of patient data permission controls 282, with each of the patient data permission controls 282 configured to modify an ability of the selected user account to perform an action or to view or to modify a subset of the patient data. For example, the permission controls 282 include check boxes for selectively allowing the selected user account to view patient personal information, patient medical data, the patient list, the patient dashboard, and/or to add, edit, or to view patient treatment plans. The patient data permission controls 282 may take other forms such as, for example, radio buttons, or drop-down selectors. As used herein, "patient personal information" refers to a bibliographic subset of PII, e.g., name, address, email, etc., but not medical data, conditions, measurements, etc."

The team member displays 240, 250, 260, 208 of FIGS. 9-12 may have other configurations or arrangements. For example, the team member modification displays 240, 250, 260 may be combined as any of one or more display screens.

Figure 13:
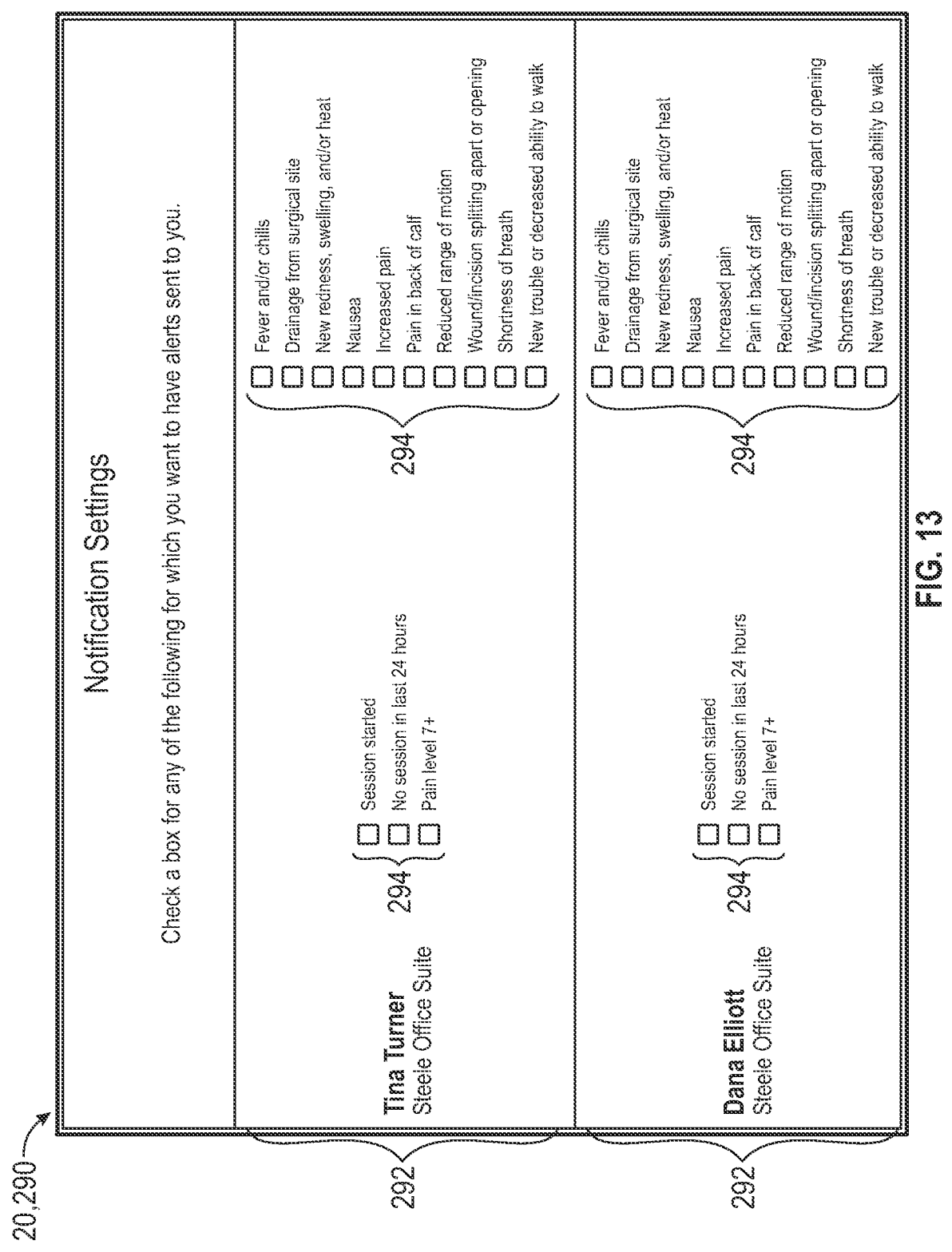

FIG. 13 shows an example embodiment of a notifications settings display 290 of the clinician interface 20. The example notifications settings display 290 includes a notification control panel 294 for each of a plurality of user accounts having an account type associated with team members (e.g. clinician or staff member) who have access to the patient data by virtue of their position. The notifications settings display 290 may present the notification control panel 292 in rows or in other forms, such as tabular data, graphical icons, etc. As shown in the example notifications settings display 290 of FIG. 13, the notification control panels 292 each include a plurality of notification enable controls 294. Each of the notification enable controls 294 is configured for designating an associated trigger condition as being enabled or disabled for a specified user account (i.e., the user account associated with the notification control panel 292 that contains the notification enable control 294). Various different trigger conditions having notification enable controls 294 are shown on FIG. 13. Those trigger conditions may include, for example, a patient starting a treatment session, a patient reporting a pain level of 7 or greater, or a reduction in range of motion. The notification enable controls 294 are shown on FIG. 13 as check boxes, however, the notification enable controls 294 may take other forms such as, for example, radio buttons or a drop-down selector.

The system 10 is configured to send an alert message to a person having the specified user account in response to occurrence of a given trigger condition for any patients assigned to the person having the specified user account, but only if the given trigger condition is designated as being enabled for the specified user account. The notification trigger event may be a reported event, which is an event based upon a condition reported by the patient, such as a pain level, a report of nausea or wound/incision splitting. Alternatively or additionally, the trigger event may be a measured event resulting from satisfaction of a condition that includes a measurement of the patient. Measured events may include, for example, a heartrate measured by a heart-rate monitor exceeding a predetermined value or reduced range of motion, as determined by a goniometer 84 which performed measurements of a patient's knee.

In some embodiments, the alert message may be sent using a communication channel outside of the clinician user interface 20 to the person having the specified user account. For example, the system 10 may be configured to send the alert message in the form of a phone call, an email, a text message, or a pager message. In some embodiments, the alert message does not include any unacceptable PII regarding the patient. For example, the alert message may include a generic message directing the person to check the clinician user interface 20. The alert message may include some additional information, such as a type of trigger condition or a severity of an associated condition (e.g., critical alert or non-critical warning alert) without including unacceptable PII regarding the patient.

Figure 14:
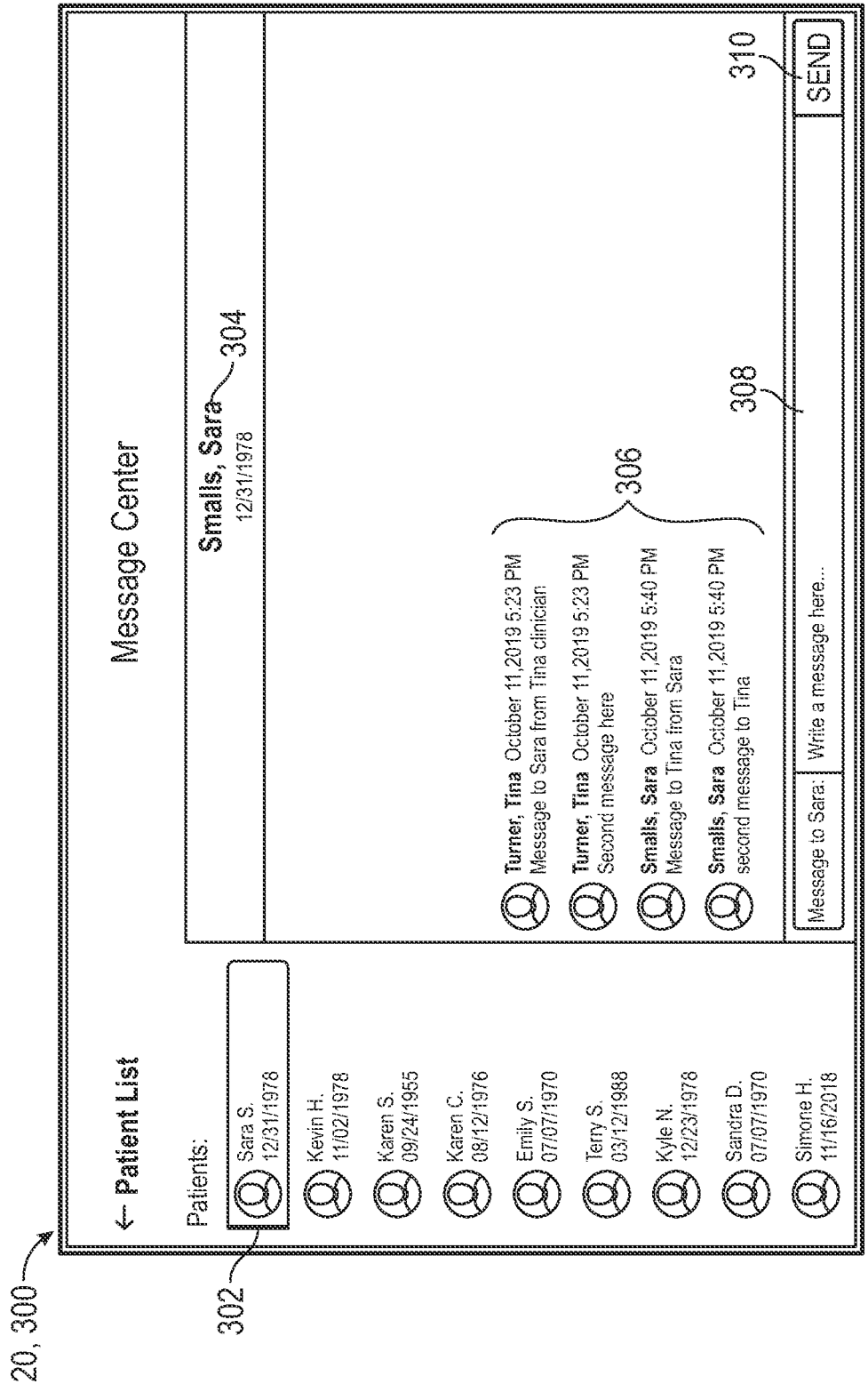
FIG. 14 shows an example embodiment of a message center display of a clinician interface.

FIG. 14 shows an example embodiment of a message center interface 300 of the clinician interface 20. The message center interface 300 may be configured as a display screen 300 as shown in FIG. 14, although the message center interface 300 may have other forms or appearances. The message center interface 300 configured to enable a textual message exchange between owners of different user accounts. Specifically, the example message center interface 300 includes a patient selector 302 for a user to select one of a plurality of patients to communicate with. The message center interface 300 also includes a selected patient indicator 304 that shows identifying information regarding a patient currently selected to send, receive, and/or view messages. The identifying information in the selected patient indicator 304 includes name and date of birth of the selected patient. The message center interface 300 also includes a message history display 306 showing a record of one or more previous textual messages exchanged between the person using the message center interface 300 and the selected patient. The message center interface 300 also includes a message input field 308 for the person using the message center interface 300 (e.g., a clinician or staff member) to compose textual messages to be sent to the selected patient). The message center interface 300 also includes a message send control 310, such as a button, and which is configured to cause the system 10 to deliver the textual message to the patient.

Figure 16:
FIG. 16 shows an example embodiment of another patient data display of a clinician interface for modifying patient personal information.

FIGS. 15-16 show example embodiments of patient data displays 320, 330 of the clinician interface 20. More specifically, the example patient data displays 320, 330 of FIGS. 15-16 are configured for modifying personal information regarding a patient. The patient data displays 320, 330 may be presented using one or more screens or displays. Each of the patient data displays 320, 330 includes a plurality of PII fields 322, each holding a corresponding PII item regarding a given patient. The PII items may include, for example, first name, last name, date of birth, email address, mobile phone number, etc. Any or all of the patient data displays 320, 330 may include a photo display 324 showing a picture of the given patient.

FIGS. 17-18 show example embodiments of medical data displays 340, 350 of the clinician interface 20. More specifically, the example medical data displays 340, 350 of FIGS. 17-18 are configured for modifying medical procedure information regarding a patient. The medical data displays 340, 350 may be presented using one or more screens or displays. One or more of the medical data displays 340, 350 include a clinician assignment control 342 configured to assign one or more clinicians as being associated with (e.g., responsible for) the given patient. Each of the medical data displays 340, 350 also includes a plurality of treatment information fields 344, each holding a corresponding treatment information item regarding the given patient. The treatment information items may include, for example, a type of procedure performed or to be performed upon the given patient, a procedure date, a start date for a rehabilitation treatment plan, a body part being treated, a treatment mode, a primary diagnosis or differential diagnosis (e.g., DRG, ICD10, etc.), a listing of pain medication prescribed to the given patient, etc.

FIG. 19 shows an example embodiment of a device data display 360 of the clinician interface 20. The device data display 360 includes device data fields 362, including data regarding the treatment apparatus 70 and/or any other devices provided for use by the given patient in performing the treatment plan. The device data fields 362 may include serial numbers and other identifying information, such as a Bluetooth MAC address for various equipment such as the treatment apparatus 70 (i.e., the "Motor"), the pedals 102, the goniometer 84 (i.e., the "Accuangle"), and/or the ambulation sensor 82 (i.e., the "Accustep").

Figure 20:
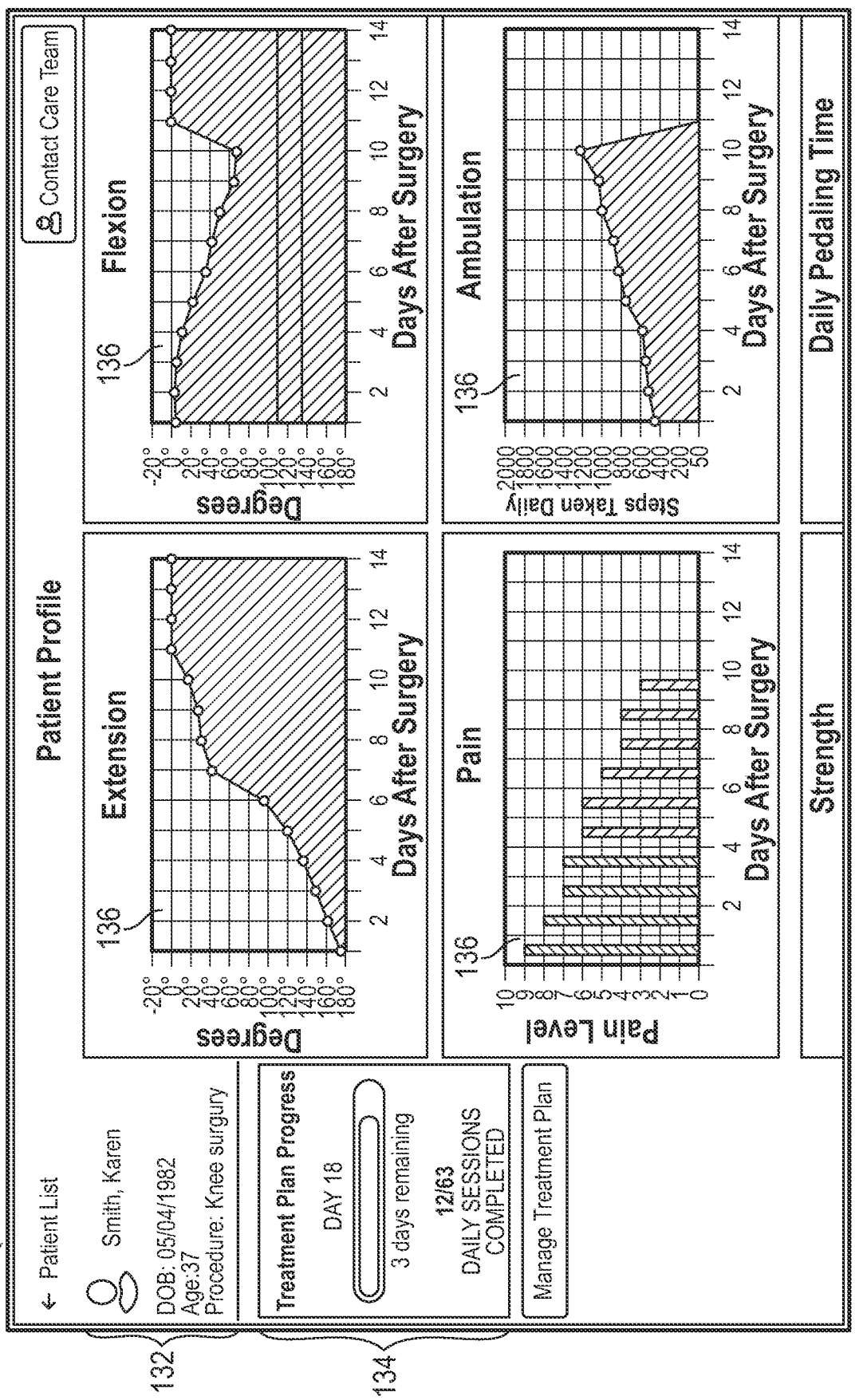
FIG. 20 shows an example embodiment of a patient profile display of a clinician interface.
Figure 21:
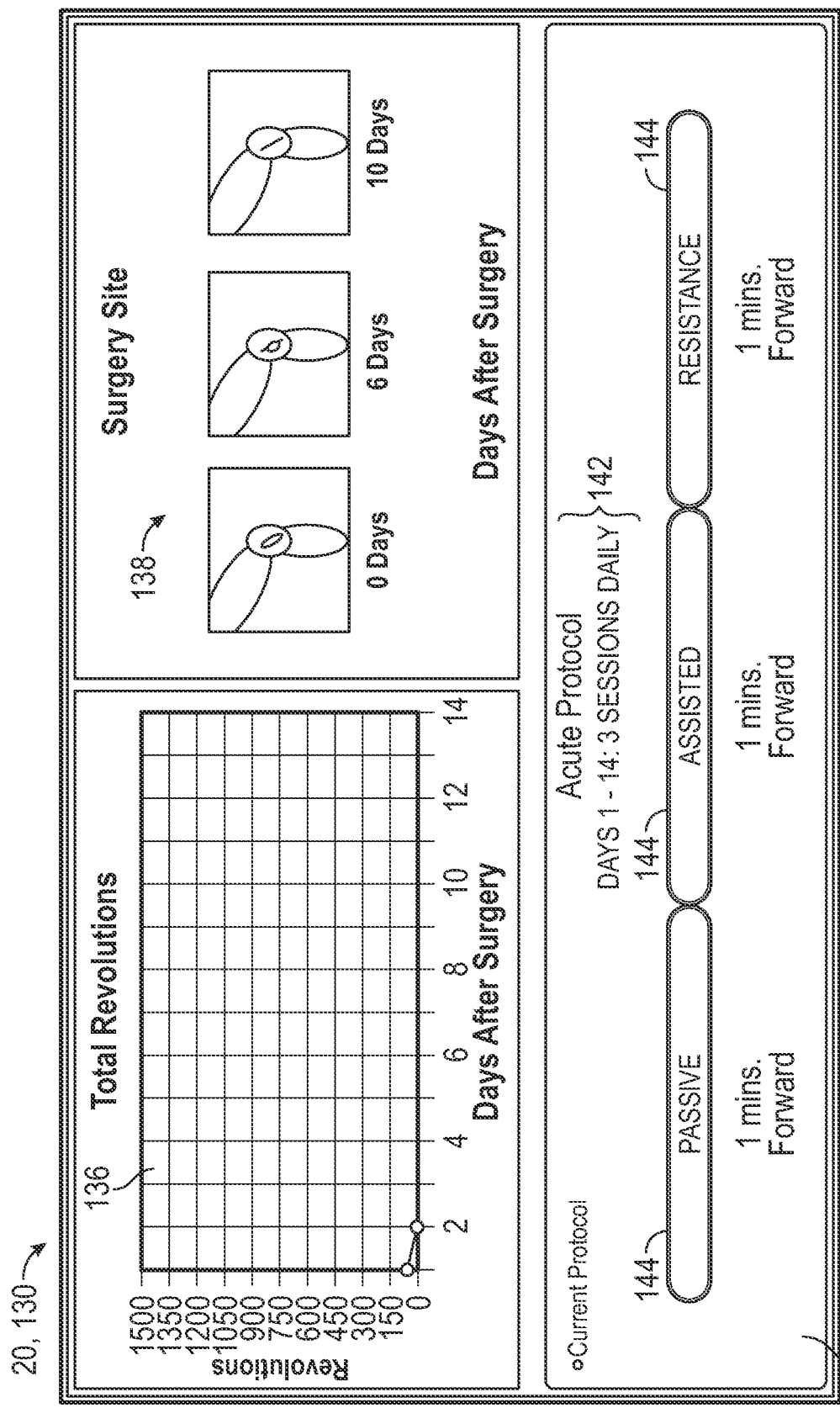
FIG. 21 shows another view of the example patient profile display of FIG. 6.

FIGS. 20-21 show an example embodiment of a patient profile display 130 of the clinician interface 20. The example patient profile display 130 includes a patient summary 132 with the patient's name, date of birth (DOB), age, a description of a procedure performed or to be performed on the patient, e.g., "Knee surgery", and a picture of the patient, if available. The example patient profile display 130 also includes a treatment progress summary 134, showing one or more indicators of progress within a treatment regimen or plan. The example treatment progress summary 134 shown on FIG. 20 includes textual progress summaries, "DAY 18", "3 days remaining", "12/63 DAILY SESSIONS COMPLETED", as well as graphical progress summaries in the form of horizontal bar graphs, which may also be called progress bars.

The example patient profile display 130 presents information regarding a treatment history of the patient. For example, the example patient profile display 130 includes a plurality of different treatment graphs 136 showing the effect of various treatment parameters over time. The treatment graphs 136 shown in the example patient profile display 130 of FIGS. 20-21 include extension (angle), flexion (angle), pain (0-10 scale), ambulation (steps/day), and total revolutions (i.e., revolutions performed on the stationary cycling machine 100). The patient profile display 130 shown on FIG. 21 also includes a pictorial history 138, showing one or more images of the surgical site for reference by a clinician or other healthcare professional in reviewing post-operative progress. The images in the pictorial history 138 may be taken by the patient and/or by a clinician or other healthcare professional. For example, the first picture may be taken by a member of the surgical staff, and subsequent pictures may be taken by the patient and/or the rehabilitation clinician. The example patient profile display 130 shown on FIG. 21 also includes a protocol summary display 140 showing a summary overview of a treatment protocol to be performed by the patient. The example protocol summary display 140 includes a protocol heading 142 with a protocol name, e.g. "Acute Protocol." The protocol heading 142 also includes overview information regarding how and when the protocol is to be performed, e.g. "Days 1-14, 3 sessions daily." The protocol summary display 140 also includes several protocol session icons 144, each indicating details of an activity to be performed within a protocol session, e.g., "Passive", "Active", or "Resistance", together with other information regarding the protocol session, such as a direction (forward/reverse), and an amount of time that each protocol session is prescribed to be performed.

Figure 22:
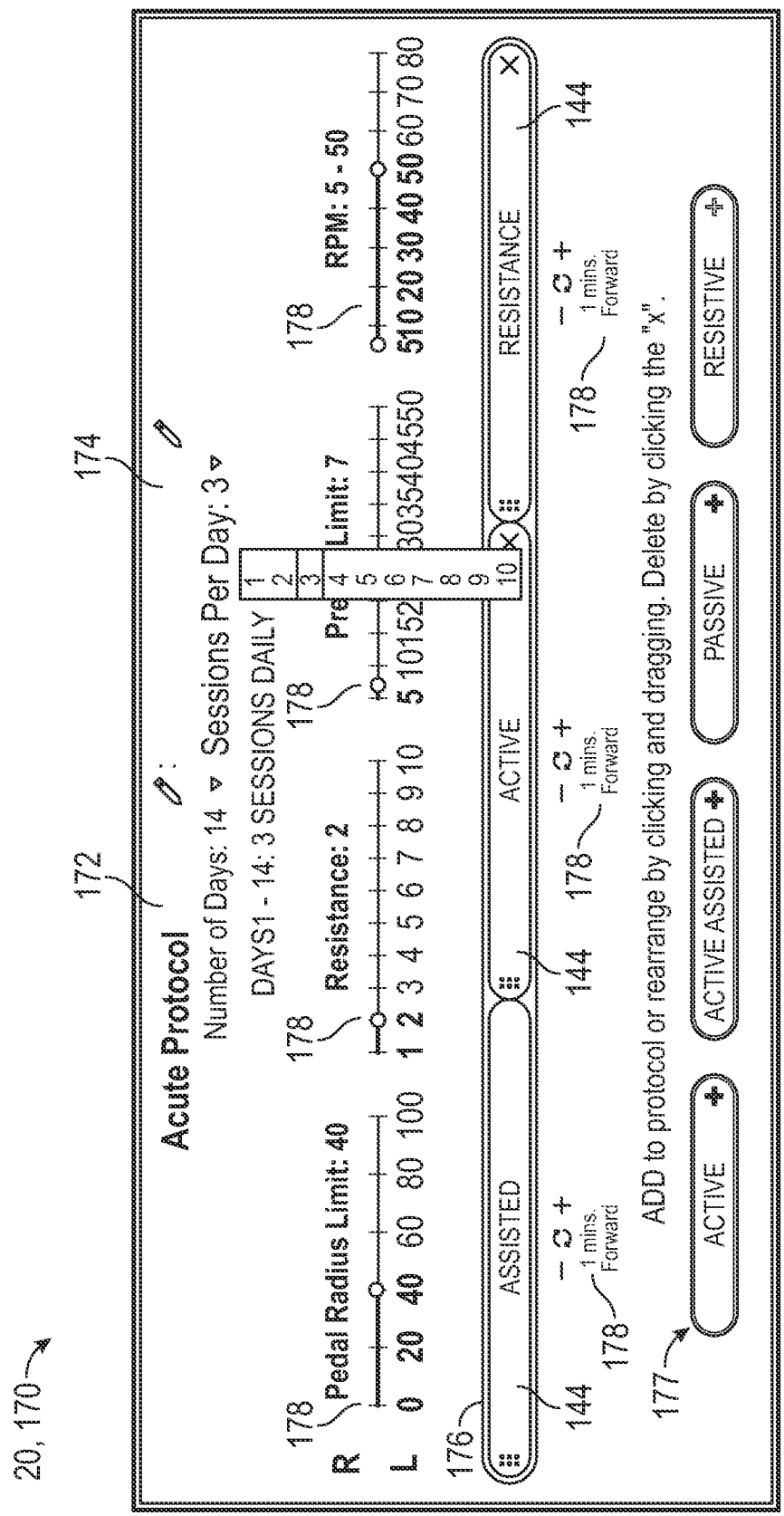
FIG. 22 shows an example embodiment of a treatment protocol management display of a clinician interface.

FIG. 22 shows an example embodiment of a protocol management display 170 of a clinician interface 20 for editing a treatment protocol 156. Specifically, the protocol management display 170 includes a protocol name control 172 for renaming the treatment protocol 156. The protocol management display 170 also includes a protocol timing control 174 for adjusting various timing settings of the treatment protocol 156, such as a duration for the treatment protocol 156 within the treatment plan 152, and a number of sessions to be performed per day. The example protocol timing control 174 shown on FIG. 22 includes drop-down menus for changing the various timing settings, but other controls could be used such as, for example, numeric entry fields or increase/decrease buttons. The protocol management display 170 also includes a protocol session control 176 for customizing the session periods. Specifically, the protocol session control 176 includes a graphical representation of a session, with protocol session icons 144, which may be similar or identical to the protocol session icons 144 of the protocol summary display 140. Each session period may have an associated type, such as passive, resistance, assisted, or active. Each session period may also have several parameters associated therewith.

The protocol session control 176 allows the clinician to adjust the number, the order, and the types of the session periods within a given session of the treatment protocol 156. Each session period has a type that corresponds to a category of activity to be performed upon a body part during that session period. For example, the session periods may be one of a passive period, an assisted period, an active period, or a resistance period. Each passive period is associated with a particular activity that includes moving a body part by an external force; each assisted period is associated with a particular activity that includes moving the body part by the patient with assistance of the external force; each active period is associated with a particular activity that includes the patient moving the body part without assistance of the external force; and each resistance period is associated with a particular activity that includes the patient actively moving the body part against a resistance force. For example, where the treatment apparatus 70 includes a stationary cycling machine 100, a passive period may include an actuator 78, such as a motor, that rotates the pedals 108 with the patient's feet and legs attached thereto and without any action or force being applied by the patient. An assisted period may include the patient applying force to rotate the pedals 108 with some additional help or assistance from the actuator 78. An active period may include the patient applying force to rotate the pedals 108 without any assistance from any outside force. A resistance period may include the patient exerting some force to rotate the pedals 108 in opposition to a resistance force applied by the actuator 78. In some embodiments, the actuator 78 may produce the external forces for each of the different categories of the session periods. The external forces may have different attributes, such as directions, intensities, or rates of changes, for each of the different categories of the session periods. Each session may include any number of session periods in any combination.

In some embodiments, the protocol session icons 144 may be modified using a drag-and-drop interface. Additional protocol sessions may be added to the protocol session using a session period control 177. Additionally, parameters for any or all of the session periods may be adjusted using various session parameter controls 178. For example, a duration and direction of each session period may be adjusted using the session parameter controls 178 located below an associated one of the protocol session icons 144. Various other parameters, such as resistance, target speed range (RPM), pedal radius limits, etc. may be adjusted using other session parameter controls 178. In some embodiments, the number and the type of session parameter controls 178 may change depending on the type of session period selected. For example, selecting a protocol session icon 144 for an active type of session period may cause the target speed range (RPM) session parameter control 178 to be visible and adjustable, but the target speed range (RPM) session parameter control 178 may not be visible and/or adjustable in response to selecting a protocol session icon 144 for a passive type session.

In some embodiments, the system 10 may impose limits on values that can be set using the session parameter controls 178. For example, the treatment plan 154 may include a maximum session time. In some embodiments, to satisfy a rule of the system 10 or a rule within the treatment plan 154, one or more of the values of the parameters may be automatically changed by the system 10. For example, the treatment plan 154 may require a resistance type of session period after an active type of session period, wherein the former is at least 25% as long as the active type of session to allow the patient to cool down after active exercise. The system 10 may automatically create the resistance type session period in response to the clinician creating an active type session period. The system 10 may also automatically adjust the time of the resistance type session period to satisfy the requirement of it lasting at least 25% as long as the active type of session.

In some embodiments, the treatment plan 154 may include maximum values for certain parameters until an associated condition is satisfied. For example, the pedal radius limit may be limited to 40 mm until an associated condition is satisfied. Associated conditions may include, for example, approval by an authorized person, such as an orthopedic surgeon; the elapsing of a particular time, such as 5 days after a surgical procedure; or successful completion of a post-operation checkup. Similarly, the treatment plan 154 may place limits on the types of session periods that may be performed until an associated condition is satisfied. The treatment plan 154 may be limited to only passive or assisted session periods (and not active periods or resistance periods until an associated condition is satisfied. Different associated conditions may be associated with each of the different parameters and/or with limits on the types of session periods available.

Figure 23:
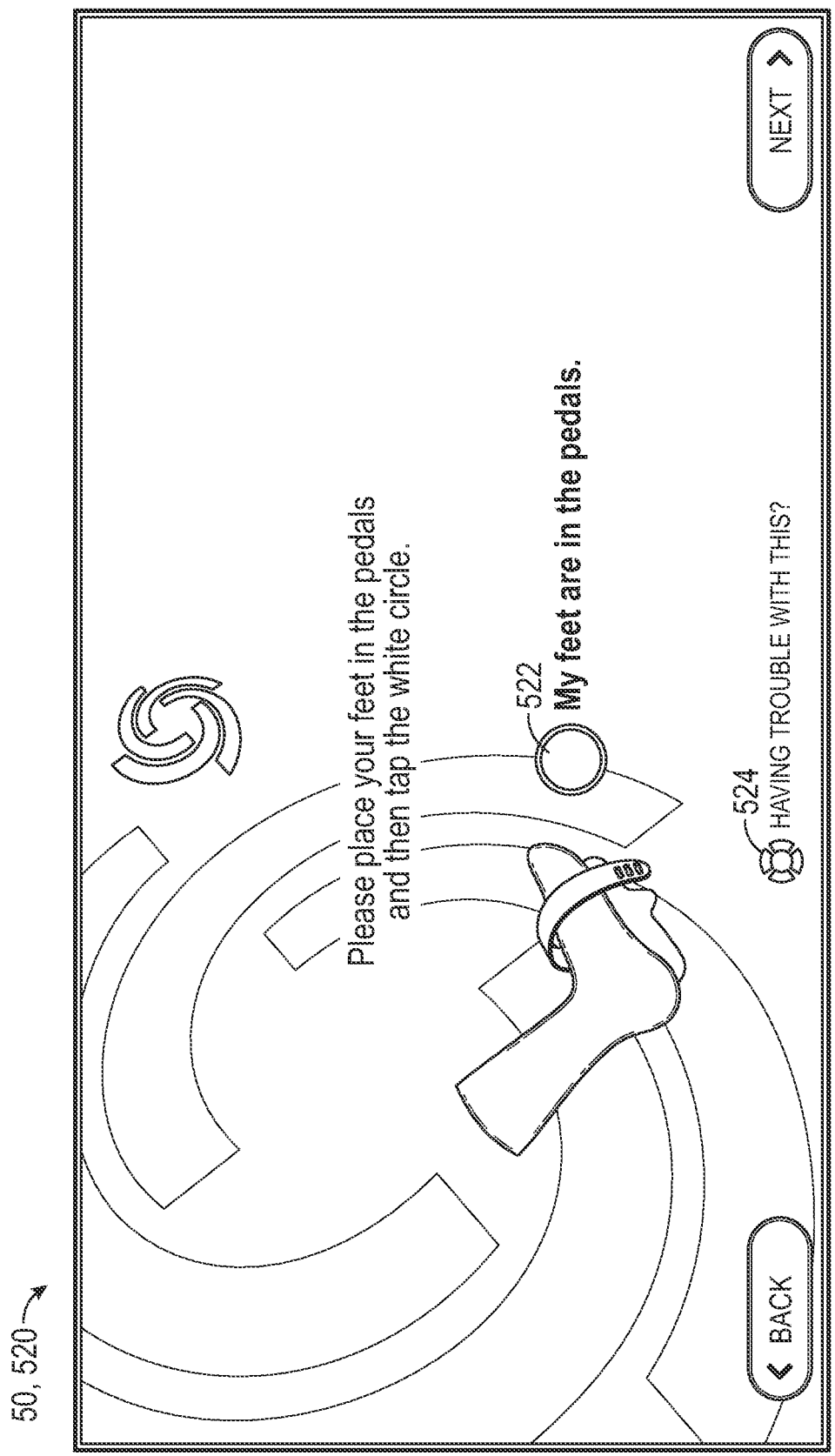
FIG. 23 shows an example embodiment of a positioning confirmation screen of a patient interface.

FIG. 23 shows an example embodiment of positioning confirmation screen 520 of the patient interface 50. This screen 520 is the beginning of a guided walk-through for the patient to use the treatment apparatus 70. Specifically, this screen 520 includes written instructions to guide the patient in placing their feet in the pedals 102 of a stationary cycling machine 100. In some embodiments, this screen 520 may include graphics, such as pictures or animations to help the patient perform particular actions for using the treatment apparatus 70. Screen 520 includes a position confirmation selector 522 for the patient to indicate that they are in position to use the treatment apparatus 70. Screen 520 also includes a trouble button 524 for the patient to indicate that they are having trouble getting in position to use the treatment apparatus 70.

Figure 24:
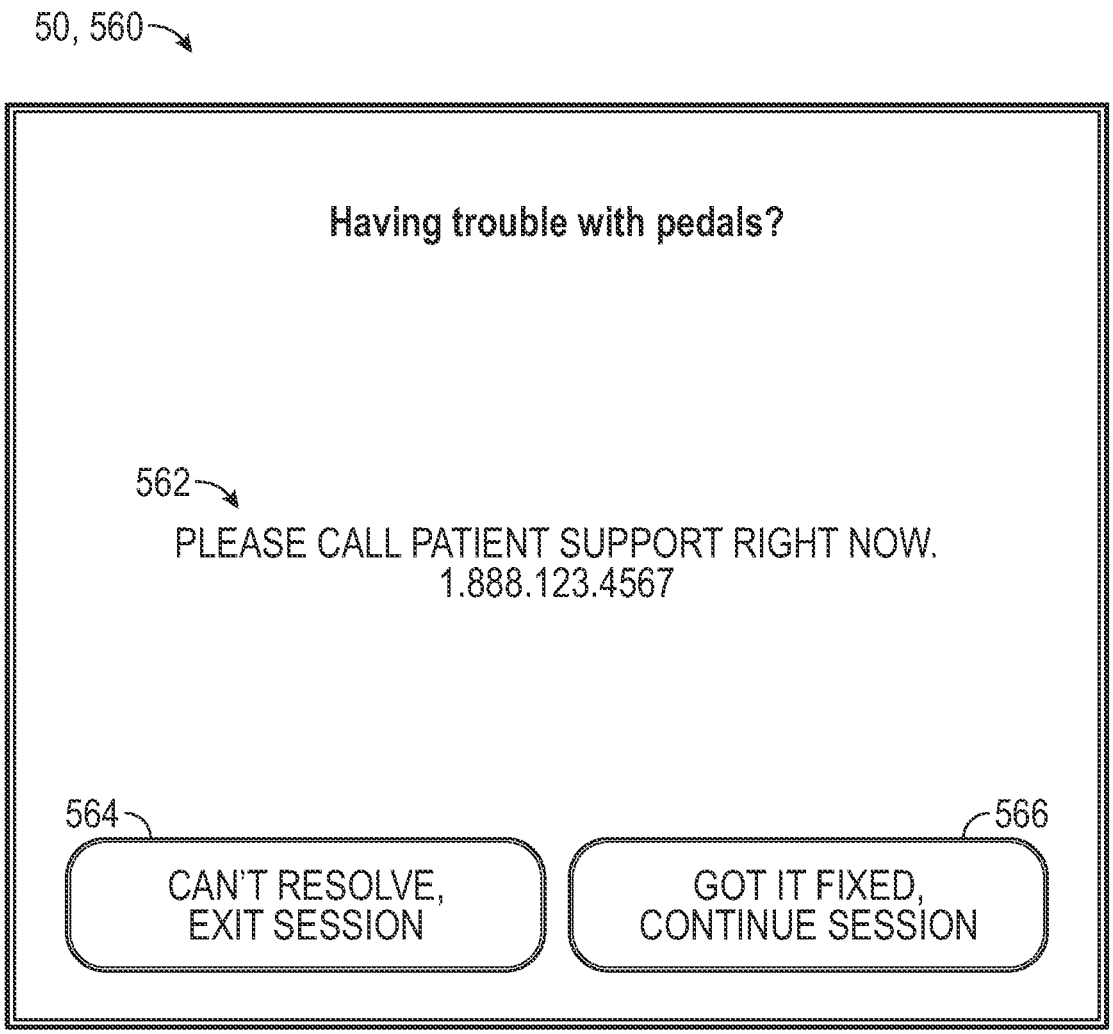
FIG. 24 shows an example embodiment of a positioning help screen of a patient interface.

FIG. 24 shows an example embodiment of a positioning help screen 560 of the patient interface 50. This help screen 560 may be shown in response to the user selecting the trouble button 524 on the positioning confirmation screen 520. The help screen 560 may automatically be displayed if the patient fails to select the position confirmation selector 522 within a predetermined period of time. In some embodiments, an intermediate screen such as a popup asking if the patient needs more time may be displayed before the help screen 560 is shown. The help screen 560 includes assistance instructions 562 for the patient to obtain assistance for using the treatment apparatus 70. In some embodiments, the assistance instructions 562 may include a phone number. The assistance instructions 562 may also include other items, such as a link to a video conference with someone able to help the patient, and/or a link to a video or animated walk-through with detailed instructions for performing a particular action to use the treatment apparatus 70. The particular action may include, for example, placing the feet in the pedals. The help screen 560 may also include an exit button 564 that the patient can use to stop the treatment session in case they are unable to resolve their issue with using the treatment apparatus 70. Use of the exit button 564 may generate an alert to the clinician. The help screen 560 also includes a proceed button 566 that the patient can use to indicate that they have resolved their issue and are able to proceed with the treatment session.

Figure 25:
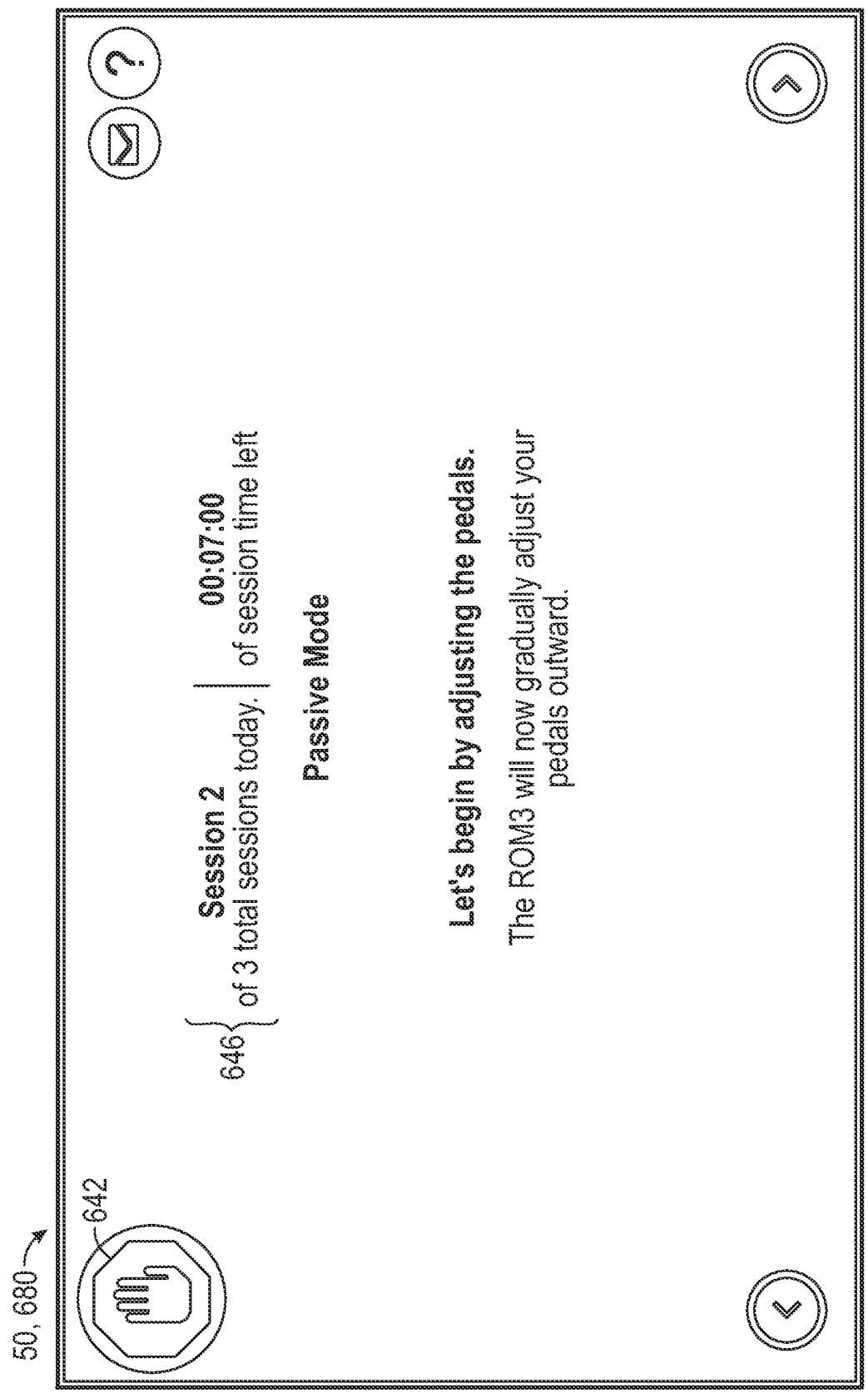
FIG. 25 shows an example embodiment of an adjustment introduction screen of a patient interface.

FIG. 25 shows an example embodiment of an adjustment introduction screen 680 of the patient interface 50. The adjustment introduction screen 680 includes text and/or graphics indicating various adjustments to be performed by the treatment apparatus 70. In the example shown, the adjustments include the treatment apparatus 70 that is a stationary cycling machine 100 that automatically moves the pedals 102 outwardly to a predetermined position for the session period.

In some embodiments, the patient interface 50 presents an adjustment confirmation control configured to solicit a response regarding the patient's comfort level with the position of the body part or the force exerted by the body part. The comfort level may be indicated by a binary selection (e.g., comfortable or not comfortable). In some embodiments, the comfort level may be an analog value that may be indicated numerically or with an analog input control, such as a slider or a rotary knob. In some embodiments, the comfort level may be indicated by one of several different comfort level values, such as an integer number from 1 to 5. In some embodiments, the comfort level may be indicated using controls for the patient to maintain a setting or for the patient to change the setting. More specifically, the control for the patient to change the setting may provide for the patient to change the setting in either of two or more directions. For example, the controls may allow the patient to maintain the value of a setting, to increase the value of the setting, or to decrease the value of the setting.

Figure 26:
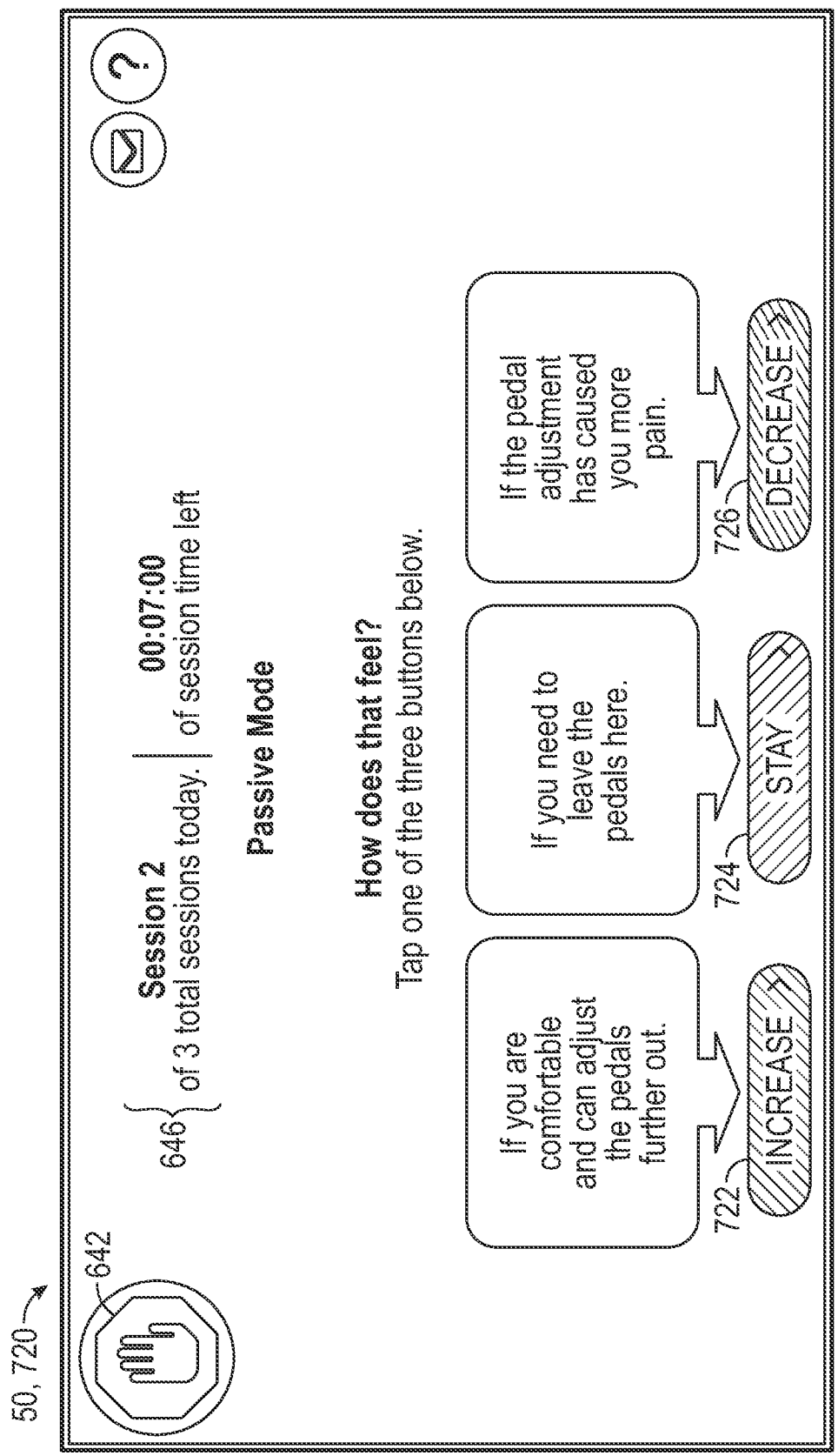
FIG. 26 shows an example embodiment of an adjustment confirmation screen of a patient interface.

The adjustment confirmation control may take the form of an adjustment confirmation screen 720, as shown, for example, in FIG. 26. The adjustment confirmation control may take other forms, such as a popup window or a portion of a larger display screen. The patient interface 50 may present the adjustment confirmation control on a graphical user interface, such as a display screen or an overlay or virtual control within a virtual reality (VR) or augmented reality (AR) display. Additionally or alternatively, the adjustment confirmation control may include one or more physical control devices, such as buttons, knobs, sliders, etc. In some embodiments, the adjustment confirmation control may be used in conjunction with an automatic adjustment, such as an actuator 78 within the treatment apparatus 70. For example, as shown in the FIGS., an actuator 78 may change the radius of one of the pedals 102, thus changing the position of the patient's knees. The adjustment confirmation control may then solicit a response regarding the patient's comfort or discomfort with the adjusted position. In another example, the patient interface 50 may prompt the patient to apply a target pressure, such as 50 lbs. The adjustment confirmation control may then solicit a response regarding the patient's comfort or discomfort in applying the target pressure.

The phrases 'increase control', 'decrease control', and 'stay control', unless explicitly stated otherwise, are intended to be understood as noun phrases meaning controls that serve the functions of increasing, decreasing, or maintaining corresponding values.

The adjustment confirmation screen 720 includes text and/or graphics requesting the patient to confirm their satisfaction with the position of the treatment apparatus 70 during and/or after the automatic adjustments are made. The adjustment confirmation screen 720 includes an increase control that the patient may select to indicate a desire to increase the value of a corresponding parameter. The corresponding parameter may be a position of the treatment apparatus 70 such as the radius of the pedal 102 on the pedal arm 104. The corresponding parameter may be a setting for a force or a speed of an exercise performed as part of the regimen. For example, the corresponding parameter may be a target pressure or a target RPM speed in a given session period. The increase control may take the form of an increase button 722, such as the button shown on FIG. 26. The increase control may take other forms, such as a knob or slider control, which may be a physical device or part of a graphical user interface. The adjustment confirmation screen 720 also includes a stay control that the patient may select to indicate a desire to maintain the value of the corresponding parameter. The stay control may take the form of a stay button 724, such as the button shown on FIG. 26. The stay control may take other forms, such as a knob or slider control, which may be a physical device or part of a graphical user interface. The adjustment confirmation screen 720 also includes a decrease control that the patient may select to indicate a desire to decrease the value of the corresponding parameter. The decrease control may take the form of a decrease button 726 such as the button shown on FIG. 26. The decrease control may take other forms, such as a knob or slider control, which may be a physical device or part of a graphical user interface. For example, if the patient experiences pain or discomfort with the initial position, he or she may change the position using the decrease button 726 until the pain or discomfort is alleviated.

In some embodiments, one or more of the increase, the decrease, and/or the stay control(s) may be provided by one or more of the sensors 76, 84, 86. For example, the patient interface 50 may prompt the patient to move a body part until they start to feel discomfort, the system 10 may use one or more of the sensors 76, 84, 86 to measure the range of motion that the body part moved, and that range of motion may be used for performing the rehabilitation regimen. In another example, one or more of the sensors 76, 84, 86, such as a pressure sensor 76 and/or a goniometer 84, may measure a physical response by the patient, such as a flinch that indicates pain. A target value of the parameter may be set based upon the value of the parameter where the patient indicated pain or discomfort. That target value of the parameter may then be used for performing the rehabilitation regimen. The target value of the parameter may be set based upon a value of the parameter where the patient indicated pain or discomfort. The target parameter value may be set to X % of P, where X is a predetermined percentage, and P is the value of the parameter where the patient indicated pain or discomfort. For example, if a patient indicated pain at a pedal radius of 6.0 cm, and X is 90%, the target parameter value for the pedal position may be set to 5.4 cm, or 90% of 6.0 cm. Alternatively, the target parameter value may be set using an offset value that is added or subtracted from the value of the parameter where the patient indicated pain or discomfort. For example, if a patient indicated pain at pedal radius of 8.0 cm, and the offset value is −1.2 cm, then the target parameter value for the pedal radius may be set to 6.8 cm. Values of other parameters, such as target pressure or target speed, may be similarly adjusted.

In some embodiments, the system 10 may be configured to persuasively motivate the patient to use one or more settings for the position of the body part and/or the force exerted by the body part. For example, the patient interface 50 may show a target value or a target range for the position of the body part and/or the force exerted by the body part. In another example, the patient interface 50 may periodically encourage the patient to increase a setting for the position of the body part and/or the force exerted by the body part, particularly where that setting is below a target value or a target range. The system 10 may gradually increase a setting for the position of the body part and/or the force exerted by the body part while the patient is using the body part to perform the rehabilitation regimen. In some embodiments, the adjustment confirmation control may be presented to the patient only after the setting for the position of the body part and/or the force exerted by the body part has been actively used in performing the rehabilitation regimen for some period of time. In some embodiments, the adjustment confirmation control may not be presented to the patient, even after the setting for the position of the body part and/or the force exerted by the body part is adjusted.

In some embodiments, the patient interface 50 may present the adjustment confirmation control before the patient performs the rehabilitation regimen. Such a pre-performance adjustment allows the patient to use a confirmed or adjusted position and/or force setting while performing the rehabilitation regimen. Additionally or alternatively, the patient interface 50 may present the adjustment confirmation control during and/or after the rehabilitation regimen. For example, the adjustment confirmation screen 720 may be presented to the patient during a session or between sessions of the rehabilitation regimen. In some embodiments, the adjustment confirmation control may be presented in response to a triggering event. The triggering event may include, for example, the patient reporting pain in excess of a given value, or an inability to complete one or more activities within the treatment plan 154, or a sudden decrease in walking performed by the patient. Additionally or alternatively, the adjustment confirmation screen 720 may be presented to the patient after the patient has completed a session of the rehabilitation regimen. Such a post-session confirmation may be used to determine the patient's comfort, which may be a proxy for satisfaction with the session of the rehabilitation regimen. The post-session confirmation may be used to determine one or more settings for use in subsequent sessions. For example, an indication of "stay" or "increase" may cause a target value for position and/or pressure of the body part to be increased in subsequent sessions of the rehabilitation regimen.

Figure 27:
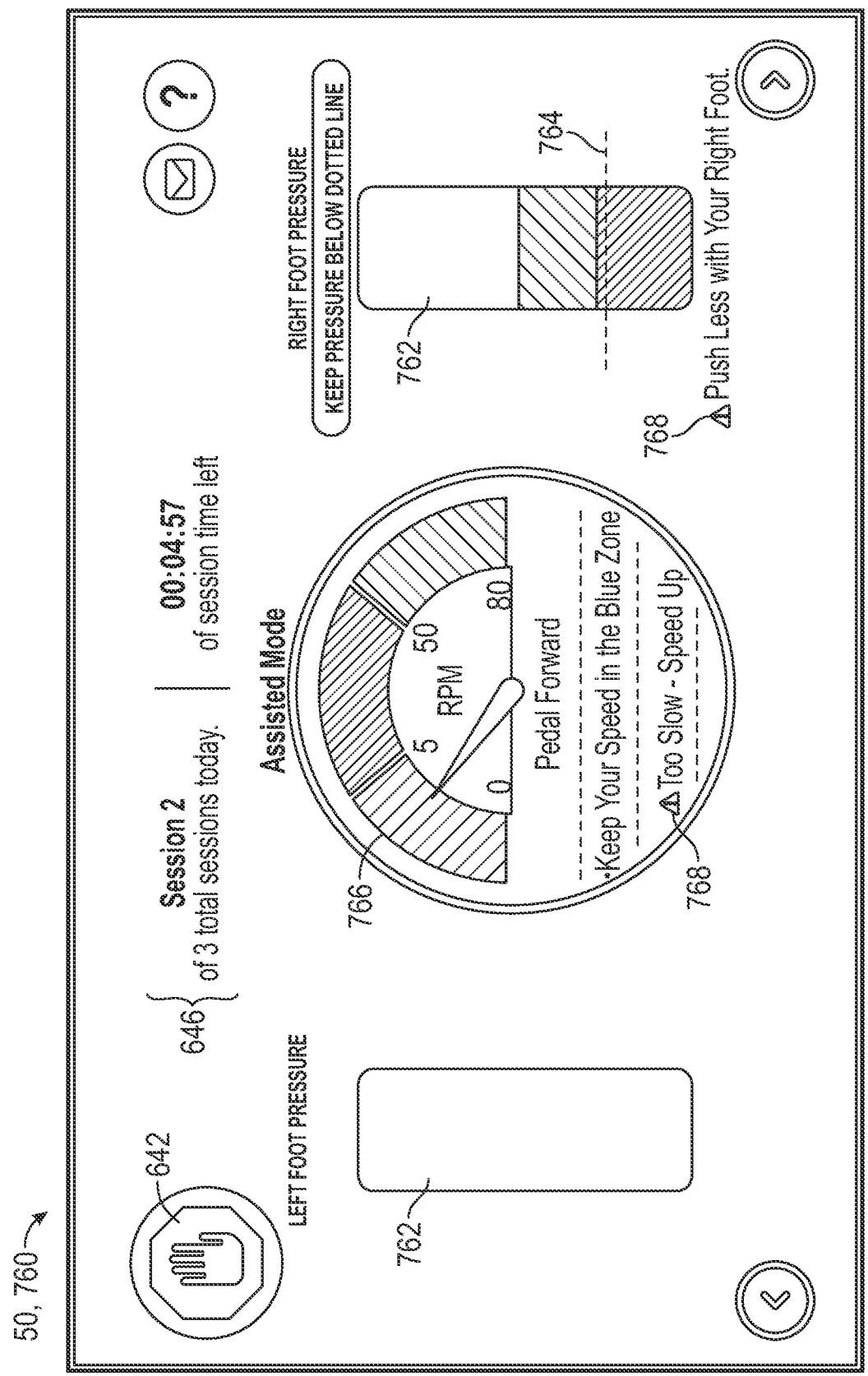
FIG. 27 shows an example embodiment of a session period action screen of a patient interface.

FIG. 27 shows an example embodiment of a session period action screen 760 of the patient interface 50. This screen 760 is displayed while a given session period is in progress. It includes one or more indicators showing real-time status of measurements regarding the patient's use of the treatment apparatus 70 to perform the rehabilitation regimen upon patient's body part. The measurements displayed may include, for example, a position of, and/or a force exerted by, the patient's body part. The example session period action screen 760 of FIG. 27 includes pressure indicators 762 showing an amount of pressure or force applied by each foot. The pressure indicators 762 show the pressures of the patient's feet upon the pedals 106 as measured by the pressure sensors 86. The pressure indicators 762 are shown as bar graphs, but other types of displays may be used, such as rotary gauges and/or numeric indicators. The pressure indicators 762 may also include a target pressure indicator 764 representing a target setting such as a target pressure value. The target setting may be determined by the clinician using an associated session parameter control 178 on the protocol management display 170, as shown, for example, on FIG. 22. The target setting may be set or adjusted via the adjustment confirmation control, by the patient.

In some embodiments, the clinician interface 20 may present information regarding the position of the body part and/or the force exerted by the body part. This information may include actual and/or target positions and/or forces as measured by one or more of the sensors 76, 84, 86. Additionally or alternatively, the information regarding the position of the body part and/or the force exerted by the body part may include a target value or a target range of values for either or both of the position of the body part and/or the force exerted by the body part. For example, the clinician interface 20 may provide a control for the clinician to adjust a value or a range of values as a target for a parameter such as a position, a force, or a speed used in a session or a session period or for a particular exercise within the rehabilitation regimen. Similarly, the clinician interface 20 may provide a control for the clinician to adjust minimum and/or maximum values for the parameter. For example, the patient may adjust the value of a pedal radius parameter from the preset target value up to the maximum value for that parameter, where the preset target value and the maximum value are both set by the clinician using corresponding controls on the clinician interface 20.

The session period action screen 760 also includes a speed indicator 766 showing a speed that the pedals 106 are turning, as measured by an internal sensor 76 of the stationary cycling machine 100. The speed indicator 766 is shown as a rotary gauge, but other types of displays may be used, such as a bar graph and/or a numeric indicator. The speed indicator 766 includes an optimal or desired speed range, which may be determined by the clinician using an associated session parameter control 178 on the protocol management display 170, as shown, for example, on FIG. 22. The session period action screen 760 may present prompts or messages 768 to enable the user to change the pressure and/or speed if either of those parameters is outside of a predetermined range.

Figure 28:
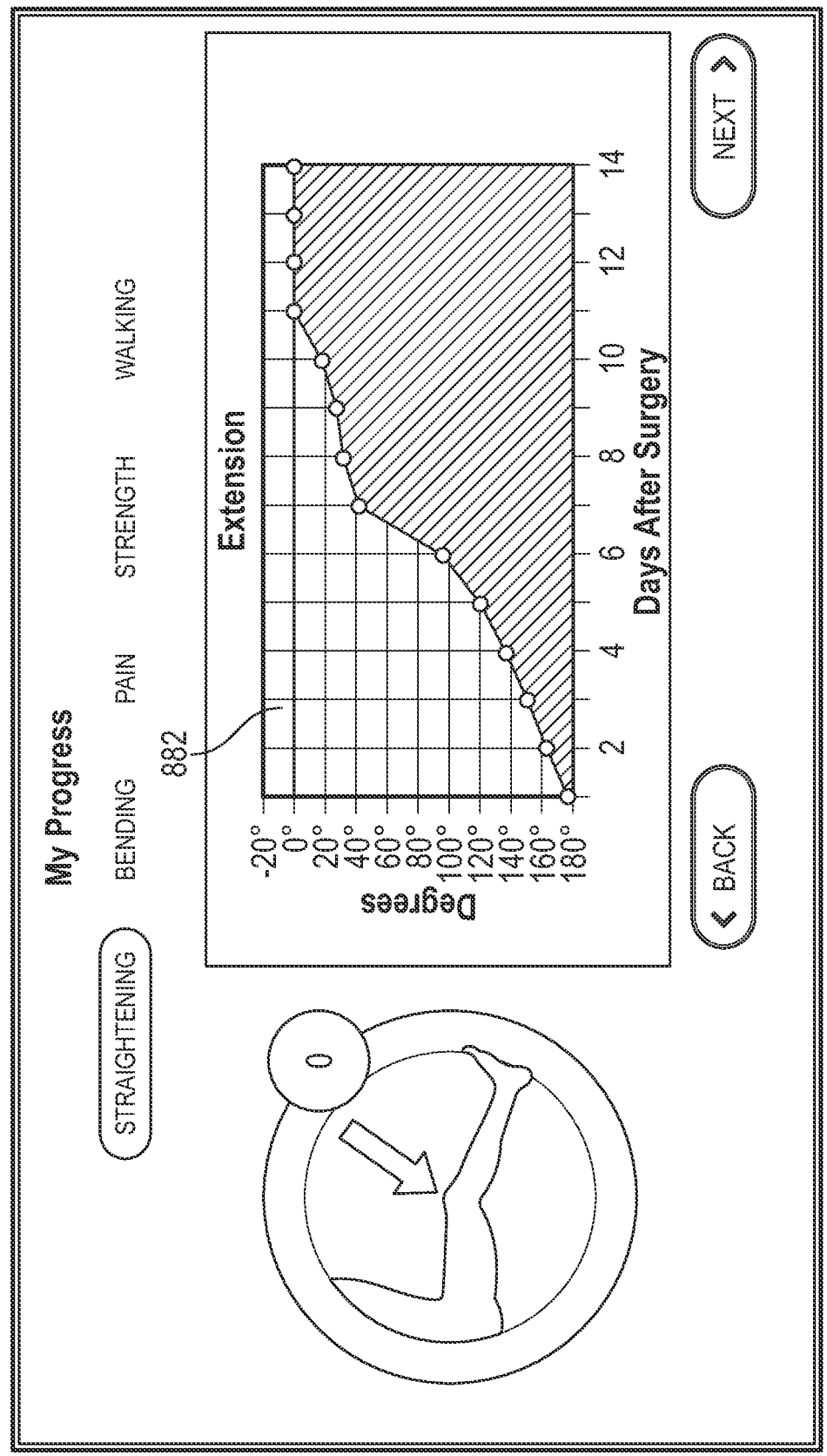
FIG. 28 shows an example embodiment of a first progress data screen of a patient interface.

FIG. 28 shows an example progress data screen 880 of the patient interface 50. The progress data screen 880 presents a progress graph 882 for each of several different parameters related to the treatment plan 154. For example, the progress graphs 882 may include historical data for straightening and bending of the knee pain, strength (lbs. pressure), and walking (steps per day). The progress graphs 882 may show identical data or data similar to what is presented on the treatment parameter graphs 136 of the clinician interface 20.

In some embodiments, a computer, such as the server 30, is configured to automatically modify the treatment plan 154 in response to satisfaction by the patient of a predetermined condition. For example, the treatment plan 154 may be limited in speed, velocity, or pressure settings or number of sessions per day until a predetermined condition is satisfied. In another example, the treatment plan 154 may include only certain types of session periods, such as passive type exercises, until the predetermined condition is satisfied. The predetermined condition may include, for example, a successful post-operative checkup; or completion of a predetermined number of sessions or satisfying a performance benchmark within the treatment plan. Such a benchmark may include, for example, walking X number of steps in a day, or some given RPM speed or a given number of pounds of force using the treatment apparatus 70. In some embodiments, the computer is configured to increase at least one of a frequency, a duration, or an intensity of an aspect of the treatment plan 154 in response to performance or occurrence of the predetermined condition. In some embodiments, the computer is configured to decrease at least one of a frequency, a duration, or an intensity of an aspect of the treatment plan 154 in response to a performance or occurrence of the condition. The predetermined condition may include, for example, the patient reporting pain in excess of a given value, or an inability to complete one or more activities within the treatment plan 154, or a sudden decrease in walking performed by the patient.

In some embodiments, the patient interface 50 may provide a prompt to the patient in response to occurrence of the predetermined condition. For example, in a session period where the patient is expected to maintain the stationary cycling machine at a speed of between 40 and 50 RPM, the predetermined condition may include the cycling machine operating below 30 RPM for a period of 5 seconds. In that case, the patient interface 50 may provide a prompt asking the patient if they are having trouble or pain in performing the activity. The prompts may narrow down a problem. For example, if the patient is unable to perform a given activity, then a computer, such as the server 30, may automatically modify the treatment plan 154 to include activities that are easier for the patient to complete, such as only passive or only assisted session periods.

Alternatively, the treatment plan 154 may be suspended until the clinician or another qualified person, such as an orthopedic surgeon, directs the system 10 to re-enable the treatment plan 154. Additionally or alternatively, the patient's responses to the prompts may generate an alert to the clinician.

In some embodiments, the system may communicate an alert message to the clinician using a communication message, such as a pager message or a text message or an email. The alert message may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject". For example, an alert message may direct the clinician that a particular type of alert exists, such as a patient reporting wound splitting, without identifying which patient made the report. The alert message may direct the clinician to check the clinician interface 20 for more specific details regarding the alert.

According to further aspects, the computer-implemented system 10 may be configured to automatically modify one or more parameters of the treatment plan based upon progress made by the patient in performing the treatment plan. For example, the server 30 may be configured to adjust one or more settings, such as frequency of sessions, a range of motion setting, and/or a pressure setting based on how the patient is progressing in the treatment plan. In some embodiments, the parameters available to be modified by the system may be adjusted within a corresponding range of values set by the clinician. For example, the clinician interface 20 may present one or more controls for the clinician to set a range of values that the system can use for each of the adjustable parameters. The system 10 may use an algorithm to add more sessions (e.g., if the patient is behind schedule). Alternatively, the system 10 may accelerate ahead to more difficult sessions if the recovery is proceeding faster than expected.

Figure 29:
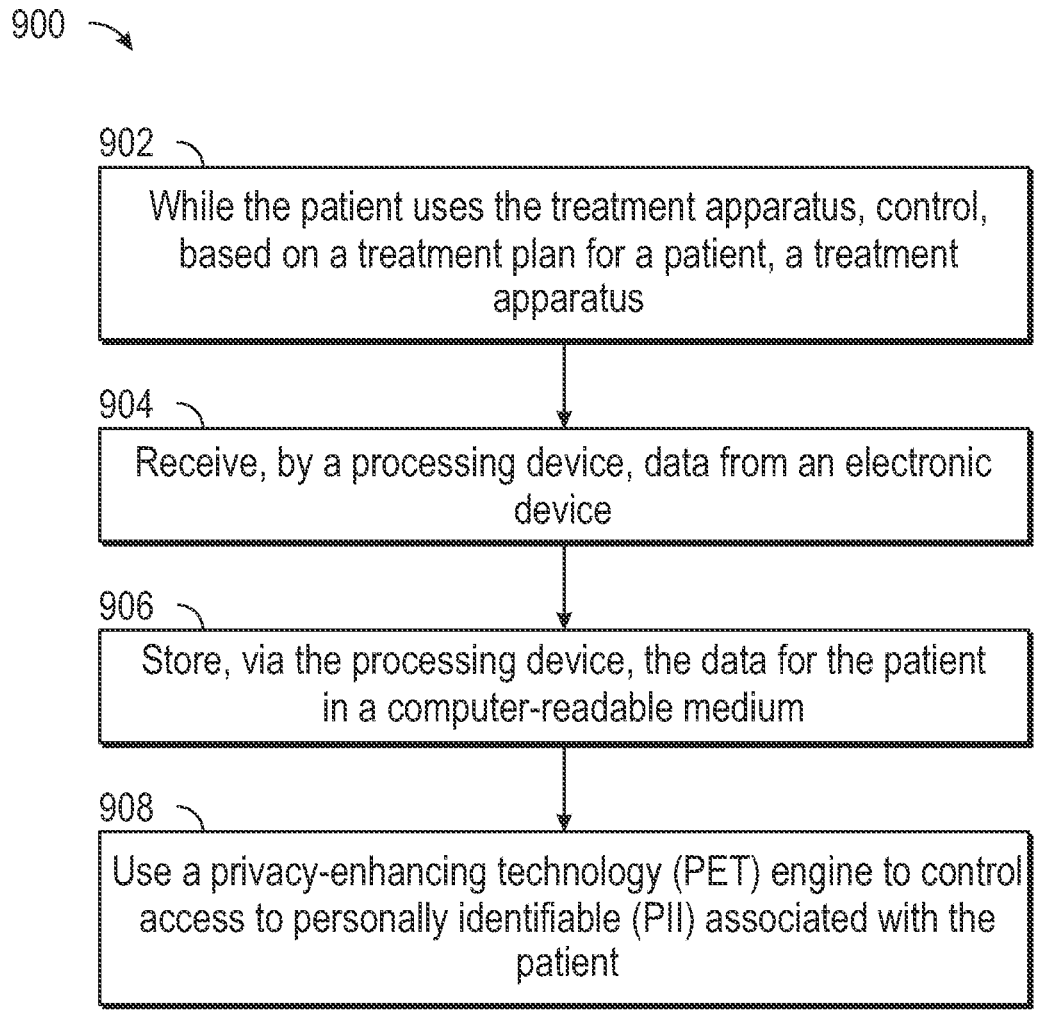
FIG. 29 shows an example flow diagram of a method for managing a treatment plan.

FIG. 29 shows an example flow diagram of a method 2900 for managing a treatment plan. The method 2900 is performed by processing logic that may include hardware (circuitry, dedicated logic, etc.), software (such as is run on a general-purpose computer system or a dedicated machine), or a combination of both. The method 2900 and/or each of its individual functions, routines, other methods, scripts, subroutines, or operations may be performed by one or more processors of a computing device (e.g., any component of any of the FIGs., such as interfaces, servers, treatment apparatuses, sensors, etc.). In certain implementations, the method 2900 may be performed by a single processing thread. Alternatively, the method 2900 may be performed by two or more processing threads, each thread implementing one or more individual functions or routines; or other methods, scripts, subroutines, or operations of the methods.

For simplicity of explanation, the method 2900 is depicted and described as a series of operations. However, operations in accordance with this disclosure can occur in various orders and/or concurrently, and/or with other operations not presented and described herein. For example, the operations depicted in the method 2900 may occur in combination with any other operation of any other method disclosed herein. Furthermore, not all illustrated operations may be required to implement the method 2900 in accordance with the disclosed subject matter. In addition, those skilled in the art will understand and appreciate that the method 2900 could alternatively be represented as a series of interrelated states via a state diagram, a directed graph, a deterministic finite state automaton, a non-deterministic finite state automaton, a Markov diagram, or event diagrams.

At 902, the processing device may control, based on a treatment plan for a patient, a treatment apparatus 70 while the patient uses the treatment apparatus 70. The treatment plan is for a body part, the body part may include at least one of a joint, a bone, or a muscle group. The treatment plan may include a physical rehabilitation regimen for improving strength or range of motion of the body part.

At 904, the processing device may receive, by a processing device, data from an electronic device (e.g., patient interface, computing device of an individual (patient, clinician, staff member, nurse, etc.), sensor internal or external to the treatment apparatus 70, or any some combination thereof). The data may include a measurement (e.g., pressure measurement from a sensor in a pedal of the treatment apparatus, speed of a motor operating within the treatment apparatus 70, range of motion (of a limb of the patient) received from a goniometer, etc.) pertaining to performance of a treatment plan by a patient using the treatment apparatus 70, a characteristic (e.g., a heartrate, a blood pressure, an amount of blood oxygen, a glucose level, a temperature, a perspiration rate, a pain level, etc.) pertaining to the patient, or both.

At 906, the processing device may store, via the processing device, the data for the patient in a computer-readable medium. At 908, the processing device may use a privacy-enhancing technology (PET) engine that uses privacy-enhancing technologies to control access to personally identifiable information (P II) associated with the patient. The PII may be included in the data stored in the computer-readable medium. In some embodiments, the PETs pseudonymize or anonymize the PII associated with the patient. In some embodiments, the PETs enable de-identification and re-identification of the PII associated with the patient.

In some embodiments, the processing device may maintain a set of user accounts, with each of the user accounts having an account type associated therewith. Each of the set of user accounts has a corresponding set of permissions enabling an owner of the user account to access the patient data.

In some embodiments, the processing device in a computing device of the patient or the clinician (e.g., patient interface or clinician interface) may select the treatment plan for the patient prior to controlling the treatment apparatus. In some embodiments, the processing device may select the treatment plan during a telemedicine session between a computing device of the patient (patient interface) and a computing device of a clinician (clinician interface).

Clauses

Clause 1. A method comprising:
while the patient uses the treatment apparatus, controlling, based on a treatment plan for a patient, a treatment apparatus;
receiving, by a processing device, data from an electronic device, wherein the data comprises a measurement pertaining to performance of a treatment plan by a patient using a treatment apparatus, a characteristic pertaining to the patient, or both;
storing, via the processing device, the data for the patient in a computer-readable medium; and
using a privacy-enhancing technology (PET) engine to control access to personally identifiable information (PII) associated with the patient.

Clause 2. The method of clause 1, wherein the treatment plan is for a body part, the body part comprising at least one of a joint, a bone, or a muscle group.

Clause 3. The method of clause 1, wherein the treatment plan comprises a physical rehabilitation regimen for improving strength or range of motion of the body part.

Clause 4. The method of clause 1, wherein the PET engine pseudonymize or anonym ize the PII associated with the patient.

Clause 5. The method of clause 1, wherein the PET engine is configured to de-identify and re-identify the PII associated with the patient.

Clause 6. The method of clause 1, further comprising:
maintaining a plurality of user accounts, with each of the user accounts having an account type associated therewith, wherein each of the plurality of user accounts has a corresponding set of permissions enabling an owner of the user account to access the patient data.

Clause 7. The method of clause 1, wherein:
the processing device is included in a computing device of a clinician or a server, and
the electronic device comprises a computing device of the patient, a sensor internal or external to the treatment apparatus, or some combination thereof.

Clause 8. The method of clause 1, further selecting, via a computing device of the patient or a clinician, the treatment plan for the patient controlling the treatment apparatus.

Clause 9. The method of clause 8, wherein the treatment plan is selected during a telemedicine session between a computing device of the patient and a computing device of a clinician.

Clause 10. A computer-implemented system for physical rehabilitation, comprising:
a clinician or patient interface comprising a patient profile display configured to present data regarding performance, by a patient, of a treatment plan for a body part, the body part comprising at least one of a joint, a bone, or a muscle group;
wherein the treatment protocol comprises a plurality of sessions for treatment of the body part of the patient;
a sensor configured to measure one of a position of the body part or a force exerted by or on the body part; and
a server configured to store patient data, the patient data including performance data regarding the performance of the treatment plan, wherein the server is controlled by a privacy-enhancing technology (PETs) engine that controls access to personally identifiable information (PII) associated with the patient.

Clause 11. The computer-implemented system of clause 10, wherein the treatment plan comprises a physical rehabilitation regimen for improving strength or range of motion of the body part.

Clause 12. The computer-implemented system of clause 10, wherein the PET engine pseudonym izes or anonym izes the P11 associated with the patient.

Clause 13. The computer-implemented system of clause 10, wherein the PET engine enables de-identification and re-identification of the PII associated with the patient.

Clause 14. The computer-implemented system of clause 10, wherein the computer-implemented system is configured to maintain a plurality of user accounts, with each of the user accounts having an account type associated therewith; and
wherein each of the plurality of user accounts has a corresponding set of permissions enabling an owner of the user account to access the patient data.

Clause 15. The computer-implemented system of clause 14, wherein the account type is one of a plurality of different account types;
wherein the plurality of different account types comprises a super-administrator account type, wherein the computer-implemented system is configured to provide a user account giving the super-administrator account type at least a greater access to the patient data than any other one of the account types.

Clause 16. The computer-implemented system of clause 14, wherein the account type is one of a plurality of different account types;
wherein the plurality of different account types comprises a practice manager account type and a clinician account type;
wherein the computer-implemented system is configured to provide a user account having the clinician account type with access to modify at least some of the patient data for patients assigned to an owner of the user account having the clinician account type, wherein the computer-implemented system is configured to provide a user account having the practice manager account type, where such account type is configured to designate another one of the user accounts as the clinician account type.

Clause 17. The computer-implemented system of clause 14, wherein the account type is one of a plurality of different account types;

wherein the plurality of different account types comprises a clinician account type and a staff member account type;

wherein the computer-implemented system is configured to provide a user account having the staff member account type, wherein the staff member account type is configured to modify at least some of the patient data for patients assigned to an owner of the user account having the staff member account type, wherein the computer-implemented system is configured to enable a user account having the clinician account type to designate another one of the user accounts as the staff member account type, wherein the computer-implemented system is configured to enable the user account having the clinician account type to assign a patient to a user account having the staff member account type.

Clause 18. The computer-implemented system of clause 14, wherein the account type is one of a plurality of different account types;

wherein the plurality of different account types comprises a patient account type, wherein the computer-implemented system is configured to enable a user account having the patient account type to view the patient data associated with their own user account.

Clause 19. The computer-implemented system of clause 14, wherein the computer-implemented system is configured to use login credentials to restrict access to each of the user accounts.

Clause 20. The computer-implemented system of clause 14, wherein, using a communication channel outside of the clinician interface and in response to a notification trigger event, the server is configured to generate an alert message to a clinician;

wherein the notification trigger event is one of a reported event or a measured event, a reported event being a condition reported by the patient, and a measured event being satisfaction of a condition that includes a measurement of the patient; and wherein the alert message comprises only authorized PII of the patient.

Clause 21. A system for remote treatment, comprising:

a clinician or patient interface configured to present controls for modifying a treatment plan comprising a regimen for treatment of a body part of a patient, with the body part comprising at least one of a joint, a bone, or a muscle group;

a treatment apparatus for performing the regimen upon the body part, the treatment apparatus configured to be manipulated by the patient; and a server configured to store patient data, the patient data including performance data regarding the performance by the patient in following the treatment plan;

wherein the patient interface and the treatment apparatus are each configured to enable operation from a patient location geographically separate from a location of the clinician interface; and wherein the server is controlled by a PET engine that controls access to PII associated with the patient.

Clause 22. A method for displaying clinician user interface generated by a computer, comprising:

a profile display presenting information regarding a treatment history of a patient;

a protocol management display presenting a treatment plan, with the treatment plan comprising a plurality of treatment protocols;

a plan modification control configured to modify the plurality of treatment protocols of the treatment plan; and a login interface configured to enable a person to access the clinician user interface by providing a credential associated with one of a plurality of user accounts, wherein each of the plurality of user accounts has a corresponding set of permissions controlling access to patient data on the clinician user interface.

Clause 23. The method of clause 1, further comprising:

a notification settings display configured to designate one or more trigger conditions as being enabled for a specified user account;

wherein an alert message is sent to a person having the specified user account in response to occurrence of a given trigger condition for any patients assigned to the person having the specified user account, only if the given trigger condition is designated as being enabled for the specified user account; and wherein the alert message is sent to the person having the specified user account using a communication channel outside of the clinician user interface.

Clause 24. The method of any clause herein, further comprising:

a team management display presenting a list of user accounts associated with a practice; and a new user add control configured to add a new user account or to associate an account type with a user account.

Clause 25. The method of any clause herein, further comprising:

a team member display configured to enable modification of characteristics of a selected user account.

Clause 26. The method of any clause herein, wherein the team member display presents an account type control input for modifying an account type associated with the selected user account.

Clause 27. The method of any clause herein, wherein the team member display presents a plurality of permission controls, wherein each of the permission controls is configured to modify an ability of the selected user account to perform an action or to view or to modify a subset of the patient data.

Clause 28. The method of any clause herein, wherein the team member display presents a plurality of permission controls, the plurality of permission controls comprising a set of account permission controls associated with a given account type;

wherein the set of account controls is configured to selectively enable an ability for the selected user account to add or modify another user account having the given account type.

Clause 29. The method of any clause herein, wherein one user account of the plurality of user accounts corresponds to a super-administrator account type, wherein the super-administrator account type has a set of permissions enabling controlling granting or revocation of access to at least a portion of PII with respect to which other entities are granted or denied the access, including the level of the access granted or denied, and to any other conditions, including time, location, identity, or some combination thereof.

Clause 30. The clinician user interface of any clause herein, wherein one user account of the plurality of user accounts corresponds to a super-administrator account type, wherein the super-administrator account type has a set of permissions enabling controlling granting or revocation of access to at least a portion of PII with respect to which other entities are granted or denied the access, including the level of the access granted or denied, and to any other conditions, including time, location, identity, or some combination thereof.

Clause 31. A computer-implemented clinician user interface for physical rehabilitation, comprising:
 a profile display presenting information regarding a treatment history of a patient;
 a protocol management display presenting a treatment plan, with the treatment plan comprising a plurality of treatment protocols;
 a plan modification control configured to modify the plurality of treatment protocols of the treatment plan; and
 a login interface configured to enable a person to access the clinician user interface by providing a credential associated with one of a plurality of user accounts, wherein each of the plurality of user accounts has a corresponding set of permissions controlling access to patient data on the clinician user interface.

Clause 32. The computer-implemented system of any clause herein, further comprising:
 a notification settings display configured to designate one or more trigger conditions as being enabled for a specified user account;
 wherein an alert message is sent to a person having the specified user account in response to occurrence of a given trigger condition for any patients assigned to the person having the specified user account, only if the given trigger condition is designated as being enabled for the specified user account; and
 wherein the alert message is sent to the person having the specified user account using a communication channel outside of the clinician user interface.

Clause 33. The computer-implemented system of any clause herein, further comprising:
 a team management display presenting a list of user accounts associated with a practice; and
 a new user add control configured to add a new user account or to associate an account type with a user account.

Clause 34. The computer-implemented system of any clause herein, further comprising:
 a team member display configured to enable modification of characteristics of a selected user account.

As will readily be appreciated by a person of ordinary skill of the art in light of having read the present disclosure, as used herein, actions described as being performed in real-time include actions performed in near-real-time without departing from the scope and intent of the present disclosure.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A method for displaying a clinician user interface generated by a computer, the method comprising:
 presenting, via a profile display of the clinician user interface, information regarding a treatment history of a patient;
 presenting, via a protocol management display of the clinician user interface, a treatment plan, wherein the treatment plan comprises a plurality of treatment protocols;
 generating a plan modification control of the clinician user interface, wherein the plan modification control comprises:
  a protocol session icon associated with a resistance value that is to be implemented at a treatment apparatus during a treatment session, the resistance value controlling a resistance setting of the treatment apparatus during the treatment session, and
  a session parameter control associated with a duration or direction that is to be implemented at the treatment apparatus during the treatment session, the duration or direction controlling a session time for use of the treatment apparatus during the treatment session;
 generating a login interface of the clinician user interface, wherein the login interface is configured to receive a credential associated with one of a plurality of user accounts, and each of the plurality of user accounts is associated with a corresponding set of permissions that control access to patient data via the clinician user interface;
 setting the credential to authorize receiving, via the clinician user interface, an adjustment to a subset of the plurality of treatment protocols of the treatment plan;
 receiving, via the clinician user interface, the adjustment to the subset of the plurality of treatment protocols of the treatment plan; and
 in response to updating the treatment plan with the adjusted subset of the plurality of treatment protocols, reconfiguring the resistance setting and the session time of the treatment apparatus in accordance with the treatment plan.

2. The method of claim 1, further comprising:
 presenting a notification settings display configured to designate one or more trigger conditions as being enabled for a specified user account, wherein:
  responsive to an occurrence of a given trigger condition, an alert message is sent to the specified user account for any patient assigned to the specified user account, and
  the alert message is sent to the specified user account using a communication channel independent of the clinician user interface.

3. The method of claim 1, further comprising:
 presenting, via a team management display of the clinician user interface, a list of user accounts associated with a practice; and
 presenting a new user add control configured to add a new user account or to associate an account type with a user account.

4. The method of claim 1, further comprising:
 presenting a team member display configured to enable modification of characteristics of a selected user account.

5. The method of claim 4, wherein the team member display presents an account type control input for modifying an account type associated with the selected user account.

6. The method of claim 4, wherein the team member display presents a plurality of permission controls, and each of the permission controls is configured to modify an ability of the selected user account to perform an action or to view or to modify a subset of the patient data.

7. The method of claim 4, wherein the team member display presents a plurality of permission controls, the plurality of permission controls comprising a set of account permission controls associated with a given account type, and the set of account controls is configured to selectively enable an ability for the selected user account to add or modify another user account having the given account type.

8. The method of claim 1, wherein one user account of the plurality of user accounts corresponds to a super-administrator account type, and the super-administrator account type has a set of permissions that enable granting or revoking access to at least a portion of personally identifiable information (PII) with respect to which other entities are granted or denied the access, including a level of the access granted or denied, and to any other conditions, including time, location, identity, or some combination thereof.

9. A clinician user interface generated by a computer, wherein the clinician user interface comprises:
  a profile display presenting information regarding a treatment history of a patient;
  a protocol management display presenting a treatment plan, wherein the treatment plan comprises a plurality of treatment protocols;
  a plan modification control configured to modify the plurality of treatment protocols, the plan modification control comprising:
    a protocol session icon associated with a resistance value that is to be implemented at a treatment apparatus during a treatment session, the resistance value controlling a resistance setting of the treatment apparatus during the treatment session, and
    a session parameter control associated with a duration or direction that is to be implemented at the treatment apparatus during the treatment session, the duration or direction controlling a session time for use of the treatment apparatus during the treatment session; and
  a login interface configured to:
    receive a credential associated with one of a plurality of user accounts, and each of the plurality of user accounts is associated with a corresponding set of permissions that control access to patient data on the clinician user interface, and
    set the credential to authorize receiving an adjustment to a subset of the plurality of treatment protocols of the treatment plan,
  wherein the plan modification control is further configured to:
    receive the adjustment to the subset of the plurality of treatment protocols of the treatment plan, and
    in response to updating the treatment plan with the adjusted subset of the plurality of treatment protocols, reconfigure the resistance setting and the session time of the treatment apparatus in accordance with the treatment plan.

10. The clinician user interface of claim 9, further comprising:
  a notification settings display configured to designate one or more trigger conditions as being enabled for a specified user account
  wherein:
    responsive to an occurrence of a given trigger condition, an alert message is sent to the specified user account for any patient assigned to the specified user account, and
    using a communication channel independent of the clinician user interface, the alert message is sent to the specified user account.

11. The clinician user interface of claim 9, further comprising:
  a team management display presenting a list of user accounts associated with a practice; and
  a new user add control configured to add a new user account or to associate an account type with a user account.

12. The clinician user interface of claim 9, further comprising:
  a team member display configured to enable modification of characteristics of a selected user account.

13. The clinician user interface of claim 12, wherein the team member display presents an account type control input for modifying an account type associated with the selected user account.

14. The clinician user interface of claim 12, wherein the team member display presents a plurality of permission controls, and each of the permission controls is configured to modify an ability of the selected user account to perform an action or to view or to modify a subset of the patient data.

15. The clinician user interface of claim 12, wherein the team member display presents a plurality of permission controls, the plurality of permission controls comprising a set of account permission controls associated with a given account type, and the set of account controls is configured to selectively enable an ability for the selected user account to add or modify another user account having the given account type.

16. The clinician user interface of claim 9, wherein one user account of the plurality of user accounts corresponds to a super-administrator account type, and the super-administrator account type has a set of permissions enabling controlling granting or revocation of access to at least a portion of personally identifiable information (PII) with respect to which other entities are granted or denied the access, including a level of the access granted or denied, and to any other conditions, including time, location, identity, or some combination thereof.

17. A computer-implemented system having a clinician user interface for physical rehabilitation, wherein the clinician user interface comprises:
  a profile display presenting information regarding a treatment history of a patient;
  a protocol management display presenting a treatment plan, wherein the treatment plan comprising a plurality of treatment protocols;
  a plan modification control configured to modify the plurality of treatment protocols, the plan modification control comprising:
    a protocol session icon associated with a resistance value that is to be implemented at a treatment apparatus during a treatment session, the resistance value controlling a resistance setting of the treatment apparatus during the treatment session, and
    a session parameter control associated with a duration or direction that is to be implemented at the treatment apparatus during the treatment session, the duration or direction controlling a session time for use of the treatment apparatus during the treatment session; and
  a login interface configured to:
    receive a credential associated with one of a plurality of user accounts, and each of the plurality of user accounts is associated with a corresponding set of permissions that control access to patient data via the clinician user interface, and set the credential to authorize receiving an adjustment to a subset of the plurality of treatment protocols of the treatment plan, wherein the plan modification control is further configured to:

receive the adjustment to the subset of the plurality of treatment protocols of the treatment plan, and in response to updating the treatment plan with the adjusted subset of the plurality of treatment protocols, reconfigure the resistance setting and the session time of the treatment apparatus in accordance with the treatment plan.

18. The computer-implemented system of claim 17, wherein the clinician user interface further comprises:

a notification settings display configured to designate one or more trigger conditions as being enabled for a specified user account, wherein:

responsive to occurrence of a given trigger condition, an alert message is sent to the specified user account for any patient assigned to the specified user account, and the alert message is sent to the specified user account using a communication channel independent of the clinician user interface.

19. The computer-implemented system of claim 17, wherein the clinician user interface further comprises:

a team management display presenting a list of user accounts associated with a practice, wherein a new user add control configured to add a new user account or to associate an account type with a user account.

20. The computer-implemented system of claim 17, wherein the clinician user interface further comprises:

a team member display configured to enable modification of characteristics of a selected user account.

* * * * *